US 8,283,465 B2

(12) United States Patent
Mitani et al.

(10) Patent No.: US 8,283,465 B2
(45) Date of Patent: Oct. 9, 2012

(54) TRIAZOLOPYRIDINE COMPOUND, AND ACTION THEREOF AS PROLYL HYDROXYLASE INHIBITOR OR ERYTHROPOIETIN PRODUCTION-INDUCING AGENT

(75) Inventors: Ikuo Mitani, Takatsuki (JP); Yosuke Ogoshi, Takatsuki (JP); Takuya Matsui, Takatsuki (JP); Masahiro Yokota, Takatsuki (JP); Masakazu Terashita, Takatsuki (JP); Dai Motoda, Takatsuki (JP); Kazuhito Ueyama, Takatsuki (JP); Hiroyuki Abe, Takatsuki (JP); Takahiro Hotta, Takatsuki (JP); Takashi Ito, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 140 days.

(21) Appl. No.: 12/837,679

(22) Filed: Jul. 16, 2010

(65) Prior Publication Data

US 2011/0077267 A1    Mar. 31, 2011

Related U.S. Application Data

(60) Provisional application No. 61/273,127, filed on Jul. 30, 2009.

(30) Foreign Application Priority Data

Jul. 17, 2009   (JP) .................. 2009-169565

(51) Int. Cl.
*C07D 345/00*    (2006.01)
(52) U.S. Cl. .............. 540/1; 546/120; 514/303
(58) Field of Classification Search .................. 514/303; 546/120
See application file for complete search history.

(56) References Cited

U.S. PATENT DOCUMENTS

| | | | |
|---|---|---|---|
| 6,093,730 | A | 7/2000 | Weidmann et al. |
| 7,608,621 | B2 | 10/2009 | Shaw et al. |
| 2007/0213335 | A1 | 9/2007 | Fitch et al. |
| 2009/0082357 | A1 | 3/2009 | Fitch et al. |
| 2009/0099171 | A1 | 4/2009 | Allen et al. |
| 2009/0156605 | A1 | 6/2009 | Allen et al. |
| 2009/0176825 | A1 | 7/2009 | Fitch et al. |
| 2010/0113444 | A1 | 5/2010 | Duffy et al. |
| 2011/0028463 | A1 | 2/2011 | Nozawa et al. |

FOREIGN PATENT DOCUMENTS

| | | |
|---|---|---|
| WO | WO 2005/014533 | 2/2005 |
| WO | WO 2007/103905 | 9/2007 |
| WO | WO 2007/136990 | 11/2007 |
| WO | WO 2007/150011 | 12/2007 |
| WO | WO 2008/089052 | 7/2008 |
| WO | WO 2008/130600 | 10/2008 |
| WO | WO 2009/005076 | 1/2009 |
| WO | WO 2009/134850 | 11/2009 |
| WO | WO 2010/069322 | 6/2010 |

OTHER PUBLICATIONS

Vippagunta et al. ("Crystalline solids"; 2001; Advanced Drug Delivery Reviews; 48: 3-26).*
Patani et al. ("Bioisosterism: A Rational Approach in Drug Design"; 1996; Chem. Rev.; 96: 3147-3176).*
International Search Report from PCT/JP2010/062037, Sep. 21, 2010.

* cited by examiner

*Primary Examiner* — Brandon Fetterolf
*Assistant Examiner* — Jean Cornet
(74) *Attorney, Agent, or Firm* — Fish & Richardson P.C.

(57) ABSTRACT

The present invention provides a triazolopyridine compound having a prolyl hydroxylase inhibitory action and an erythropoietin production-inducing ability. The present invention relates to a compound represented by the following formula [I]:

[I]

wherein each symbol is as defined in the specification, or a pharmaceutically acceptable salt thereof, or a solvate thereof, as well as a prolyl hydroxylase inhibitor or erythropoietin production-inducing agent containing the compound. The compound of the present invention shows a prolyl hydroxylase inhibitory action and an erythropoietin production-inducing ability and is useful as a prophylactic or therapeutic agent for various diseases and pathologies (disorders) caused by decreased production of erythropoietin.

30 Claims, No Drawings

TRIAZOLOPYRIDINE COMPOUND, AND ACTION THEREOF AS PROLYL HYDROXYLASE INHIBITOR OR ERYTHROPOIETIN PRODUCTION-INDUCING AGENT

CROSS REFERENCE TO RELATED APPLICATIONS

This application claims the benefit of priority of U.S. provisional application Ser. No. 61/273,127, filed Jul. 30, 2009, and Japanese application serial number 2009-169565, filed Jul. 17, 2009. The disclosures of the prior applications are considered part of (and are incorporated by reference in) the disclosure of this application.

TECHNICAL FIELD

The present invention relates to a novel triazolopyridine compound having a prolyl hydroxylase (hereinafter to be also referred to as "PHD") inhibitory action and an erythropoietin (hereinafter also referred to as "EPO") production-inducing ability. The present invention also relates to a prolyl hydroxylase inhibitor (hereinafter to be also referred to as "PHD inhibitor") and an erythropoietin production-inducing agent (hereinafter to be also referred to as "EPO production-inducing agent"), each containing the triazolopyridine compound.

BACKGROUND OF THE INVENTION

EPO is a hormone that promotes growth of red blood cell consisting of 165 amino acids. EPO is mainly produced in the kidney and partly in the liver, and the production thereof increases under low oxygen conditions.

Anemia refers to a condition showing low levels of red blood cell and hemoglobin in the blood. The symptoms thereof are derived from oxygen deficiency due to decreased number of red blood cells, or changes of the circulation dynamics due to increased breathing rate and cardiac rate to compensate for the oxygen deficiency, and include "general sick feeling", "easily-fatigued", "short breath", "palpitation", "heaviness of the head", "dizziness", "bad complexion", "shoulder stiffness", "difficulty in awakening in the morning" and the like.

The cause of anemia is largely divided into low production, promoted destruction and promoted loss of red blood cells, and anemia includes anemia due to hematopoiesis abnormality in the bone marrow, anemia due to shortage of iron, vitamin $B_{12}$ or folic acid, bleeding during accident or operation, anemia associated with chronic inflammation (autoimmune diseases, malignant tumor, chronically-transmitted diseases, plasma cell dyscrasia etc.), anemia associated with endocrine diseases (hypothyroidism, autoimmune polyglandular syndrome, type IA diabetes, dysfunctional uterine bleeding etc.), anemia associated with chronic cardiac failure, anemia associated with ulcer, anemia associated with hepatic diseases, senile anemia, drug-induced anemia, renal anemia (anemia associated with renal failure), anemia associated with chemical therapy, and the like.

In 1989, a gene recombinant human EPO preparation was approved by the U.S. Food and Drug Administration (FDA) for application to renal anemia, anemia associated with AZT treatment of HIV patients, anemia associated with chemical therapy of cancer patients, or for reduction of blood transfusion volume for patients who underwent an operation. Moreover, its application has been spreading to anemia of prematurity and the like.

Renal anemia is treated with an erythropoiesis stimulating agent (ESA). Renal anemia is mainly caused by decreased EPO production in the interstitial cells in the periphery of renal tubule of the kidney. It is an application wherein gene recombinant human erythropoietin is highly often used for supplement of EPO. Gene recombinant human erythropoietin has strikingly reduced the number of patients in need of periodic blood transfusion, improved various symptoms associated with anemia and greatly contributed to the improvement of ADL (Activities of daily living) and QOL (Quality of Life). On the other hand, being a biological preparation, it is expensive and requires high medical expenses. In addition, it has a short half-life in blood and requires 2-3 times of intravenous administration per week from the dialysis circuit in hemodialysis patients. Thus, the injection frequency is desired to be decreased to prevent medical accidents, and also from the aspects of the amount of medical practice and waste. Furthermore, for peritoneal dialysis patients and patients with renal failure in predialysis period, for whom subcutaneous administration affording a longer period of duration has been employed, once per one or two weeks of administration is still necessary. In this case, the patients often need to go to the hospital only for the administration of gene recombinant human erythropoietin, causing burden on the patients.

Moreover, a long-acting EPO medicament having a prolonged half-life in blood by intravenous injection or subcutaneous injection has been developed by modifying EPO by adding a new sugar chain or PEG chain. However, since only injection preparations have been developed, an orally administrable ESA is desired to prevent medical accidents and reduce burden on patients.

Moreover, an orally administrable ESA is expected to be applicable to a wider range of treatments for not only renal anemia but also anemia caused by various causes.

As a representative molecule promoting transcription of EPO, Hypoxia Inducible Factor (hereinafter to be also referred to as "HIF") can be mentioned. HIF is a protein consisting of a heterodimer having an oxygen regulatory α-subunit and a constitutionally-expressed β-subunit, where proline in the α-subunit is hydroxylated by prolyl hydroxylase (PHD) in the presence of oxygen and the resulting α-subunit is bound to von Hippel-Lindau (VHL) protein and ubiquitinated. However, since α-subunit is not subject to hydroxylation by PHD under low oxygen conditions, it is not ubiquitinated but bound to an intranuclear hypoxia response element (HRE) to promote transcription of EPO present at the downstream of HIF. Therefore, inhibition of the activity of PHD results in the prevention of ubiquitination of HIF and stabilization thereof. Consequently, the EPO production is increased.

Examples of the diseases expected to be improved by inhibiting PHD to stabilize HIF include ischemic cardiac diseases (angina pectoris, myocardial infarction etc.), ischemic cerebrovascular disorders (cerebral infarction, cerebral embolism, transient cerebral ischemic attack etc.), chronic renal failures (ischemic nephropathy, renal tubule interstitial disorder etc.), diabetic complications (diabetic wound etc.), cognitive impairments (dementia, Alzheimer's disease, Parkinson's disease, Huntington's disease etc.) and the like.

SUMMARY OF THE INVENTION

Problems to be Solved by the Invention

From the findings obtained from the studies heretofore, it has been clarified that a medicament inhibiting prolyl hydroxylase (PHD) promotes production of erythropoietin (EPO) and is effective for the prophylaxis or treatment of various diseases and pathologies (disorders) caused by decreased production of EPO, particularly for the treatment of anemia.

Accordingly, the present invention aims to provide a medicament having a prolyl hydroxylase (PHD) inhibitory action. In addition, the present invention aims to provide a medicament having EPO production-inducing ability.

Means of Solving the Problems

The present inventors have found a compound having a prolyl hydroxylase (PHD) inhibitory action and EPO production-inducing ability, and completed the present invention.

More particularly, the present invention provides the following.

[1] A compound represented by the following formula [I] (hereinafter to be also referred to as "the compound of the present invention") or a pharmaceutically acceptable salt thereof, or a solvate thereof:

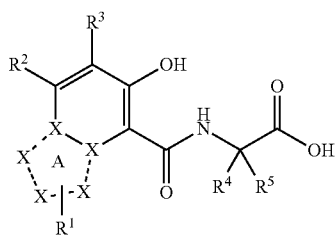

wherein
the partial structural formula:

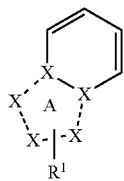

is a group represented by any of the following formulas:

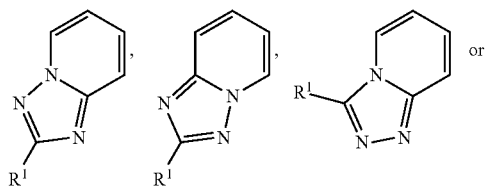

$R^1$ is
(1) a hydrogen atom,
(2) a $C_{1-6}$ alkyl group,
(3) a $C_{6-14}$ aryl group,
(4) a $C_{3-8}$ cycloalkyl group,
(5) a $C_{6-14}$ aryl-$C_{1-6}$ alkyl group, or
(6) a $C_{3-8}$ cycloalkyl-$C_{1-6}$ alkyl group;
$R^2$ is
(1) a hydrogen atom,
(2) a $C_{1-10}$ alkyl group,
(3) a $C_{6-14}$ aryl group optionally substituted by the same or different 1 to 5 substituents selected from the following group B,
(4) a $C_{3-8}$ cycloalkyl group optionally substituted by the same or different 1 to 5 substituents selected from the following group B,
(5) a $C_{3-8}$ cycloalkenyl group optionally substituted by the same or different 1 to 5 substituents selected from the following group B,
(6) a heteroaryl group optionally substituted by the same or different 1 to 5 substituents selected from the following group B (wherein the heteroaryl has, besides carbon atom, 1 to 6 hetero atoms selected from nitrogen atom, oxygen atom and sulfur atom),
(7) a $C_{6-14}$ aryl-$C_{1-6}$ alkyl group (wherein $C_{6-14}$ aryl is optionally substituted by the same or different 1 to 5 substituents selected from the following group B), or
(8) a $C_{3-8}$ cycloalkyl-$C_{1-6}$ alkyl group (wherein $C_{3-8}$ cycloalkyl is optionally substituted by the same or different 1 to 5 substituents selected from the following group B);
$R^3$ is
(1) a hydrogen atom,
(2) a halogen atom,
(3) a $C_{1-6}$ alkyl group,
(4) a $C_{6-14}$ aryl group,
(5) a $C_{3-8}$ cycloalkyl group, or
(6) a $C_{6-14}$ aryl-$C_{1-6}$ alkyl group; and
$R^4$ and $R^5$ are each independently
(1) a hydrogen atom, or
(2) a $C_{1-6}$ alkyl group,
group B:
(a) a halogen atom,
(b) a $C_{1-6}$ alkyl group,
(c) a $C_{3-8}$ cycloalkyl group,
(d) a cyano group, and
(e) a halo-$C_{1-6}$ alkyl group.

[2] The compound described in the above-mentioned [1] wherein the partial structural formula:

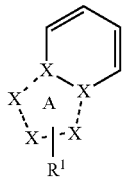

is a group represented by the following formula

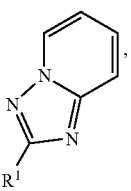

or a pharmaceutically acceptable salt thereof, or a solvate thereof.

[3] The compound described in the above-mentioned [1], wherein the partial structural formula:

$$\begin{array}{c} X{-}X \\ X{\cdot}\overset{A}{\underset{R^1}{|}}{\cdot}X \end{array}$$

is a group represented by the following formula (triazolopyridine structure with R¹)

or a pharmaceutically acceptable salt thereof, or a solvate thereof.

[4] The compound described in the above-mentioned [1], wherein the partial structural formula:

$$\begin{array}{c} X{\cdot}{\cdot}X \\ X{\cdot}\overset{A}{\underset{R^1}{|}}{\cdot}X \end{array}$$

is a group represented by the following formula (triazolopyridine structure with R¹)

or a pharmaceutically acceptable salt thereof, or a solvate thereof.

[5] The compound described in the above-mentioned [1], wherein the partial structural formula:

$$\begin{array}{c} X{\cdot}{\cdot}X \\ X{\cdot}\overset{A}{\underset{R^1}{|}}{\cdot}X \end{array}$$

is a group represented by the following formula (triazolopyridine structure with R¹)

or a pharmaceutically acceptable salt thereof, or a solvate thereof.

[6] The compound described in any of the above-mentioned [1] to [5], wherein both $R^4$ and $R^5$ are hydrogen atoms, or a pharmaceutically acceptable salt thereof, or a solvate thereof.

[7] The compound described in any of the above-mentioned [1] to [5], wherein $R^3$ is a hydrogen atom, or a pharmaceutically to acceptable salt thereof, or a solvate thereof.

[8] The compound described in any of the above-mentioned [1] to [5], wherein $R^1$ is a hydrogen atom, or a pharmaceutically acceptable salt thereof, or a solvate thereof.

[9] The compound described in any of the above-mentioned [1] to [5], wherein $R^2$ is (1) a $C_{1-10}$ alkyl group, (2) a $C_{6-14}$ aryl group optionally substituted by the same or different 1 to 5 substituents selected from the above-mentioned group B, (3) a $C_{6-14}$ aryl-$C_{1-6}$ alkyl group (wherein $C_{6-14}$ aryl is optionally substituted by the same or different 1 to 5 substituents selected from the above-mentioned group B), or (4) a $C_{3-8}$ cycloalkyl-$C_{1-6}$ alkyl group (wherein $C_{3-8}$ cycloalkyl is optionally substituted by the same or different 1 to 5 substituents selected from the above-mentioned group B), or a pharmaceutically acceptable salt thereof, or a solvate thereof.

[10] The compound described in the above-mentioned [2], wherein both $R^4$ and $R^5$ are hydrogen atoms, or a pharmaceutically acceptable salt thereof, or a solvate thereof.

[11] The compound described in the above-mentioned [10], wherein $R^3$ is a hydrogen atom, or a pharmaceutically acceptable salt thereof, or a solvate thereof.

[12] The compound described in the above-mentioned [11], wherein $R^1$ is a hydrogen atom, or a pharmaceutically acceptable salt thereof, or a solvate thereof.

[13] The compound described in the above-mentioned [12], wherein $R^2$ is (1) a $C_{1-10}$ alkyl group, or (2) a $C_{6-14}$ aryl-$C_{1-6}$ alkyl group (wherein $C_{6-14}$ aryl is optionally substituted by the same or different 1 to 5 substituents selected from the above-mentioned group B), or a pharmaceutically acceptable salt thereof, or a solvate thereof.

[14] A compound represented by the following formula [I-1] or a pharmaceutically acceptable salt thereof, or a solvate thereof:

[I-1]

(structure with $R^{31}$, $R^{21}$, OH, $X^1$, $A^1$, $X^1$, $X^1$, $R^{11}$, N-H, O, $R^{41}$, $R^{51}$, OH)

wherein the partial structural formula:

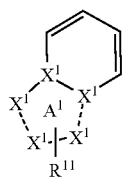

is a group represented by any of the following formulas:

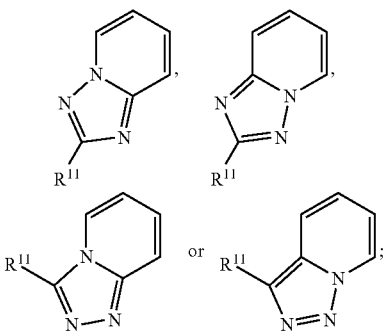

$R^{11}$ is
(1) a hydrogen atom,
(2) a $C_{1-6}$ alkyl group,
(3) a phenyl group,
(4) a $C_{3-8}$ cycloalkyl group,
(5) a phenyl-$C_{1-6}$ alkyl group, or
(6) a $C_{3-8}$ cycloalkyl-$C_{1-6}$ alkyl group;
$R^{21}$ is
(1) a hydrogen atom,
(2) a $C_{1-10}$ alkyl group,
(3) a phenyl group optionally substituted by the same or different 1 to 5 substituents selected from the following group B,
(4) a $C_{3-8}$ cycloalkyl group,
(5) a $C_{3-8}$ cycloalkenyl group,
(6) a thienyl group optionally substituted by the same or different 1 to 5 substituents selected from the following group B,
(7) a phenyl-$C_{1-6}$ alkyl group (wherein phenyl is optionally substituted by the same or different 1 to 5 substituents selected from the following group B), or
(8) a $C_{3-8}$ cycloalkyl-$C_{1-6}$ alkyl group;
$R^{31}$ is
(1) a hydrogen atom,
(2) a halogen atom,
(3) a $C_{1-6}$ alkyl group,
(4) a phenyl group,
(5) a $C_{3-8}$ cycloalkyl group, or
(6) a phenyl-$C_{1-6}$ alkyl group; and
$R^{41}$ and $R^{51}$ are each independently
(1) a hydrogen atom, or
(2) a $C_{1-6}$ alkyl group
group B:
(a) a halogen atom,
(b) a $C_{1-6}$ alkyl group,
(c) a $C_{3-8}$ cycloalkyl group,
(d) a cyano group, and
(e) a halo-$C_{1-6}$ alkyl group.

[15] A compound represented by the following formula:

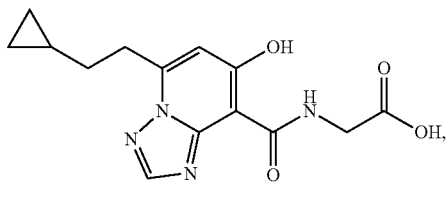

or a pharmaceutically acceptable salt thereof, or a solvate thereof.

[16] a compound represented by the following formula:

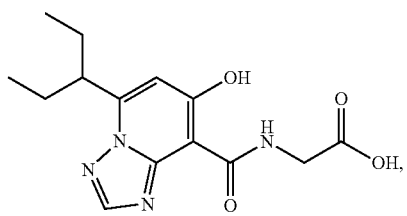

or a pharmaceutically acceptable salt thereof, or a solvate thereof.

[17] A compound represented by the following formula:

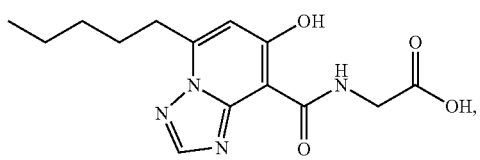

or a pharmaceutically acceptable salt thereof, or a solvate thereof.

[18] A compound represented by the following formula:

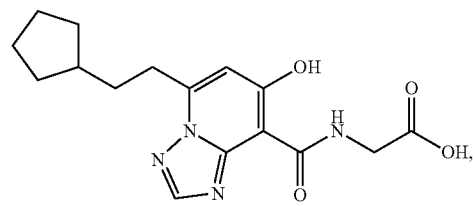

or a pharmaceutically acceptable salt thereof, or a solvate thereof.

[19] A compound represented by the following formula:

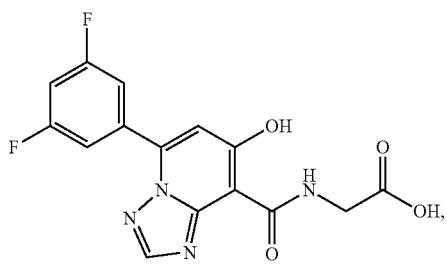

or a pharmaceutically acceptable salt thereof, or a solvate thereof.

[20] A compound represented by the following formula:

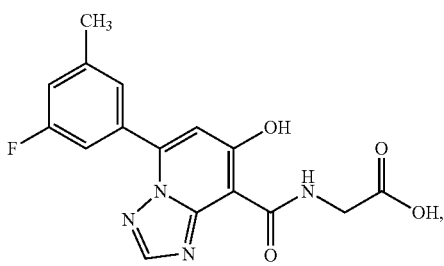

or a pharmaceutically acceptable salt thereof, or a solvate thereof.

[21] A compound represented by the following formula:

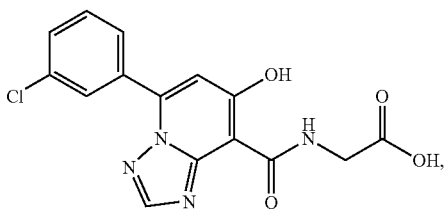

or a pharmaceutically acceptable salt thereof, or a solvate thereof.

[22] A compound represented by the following formula:

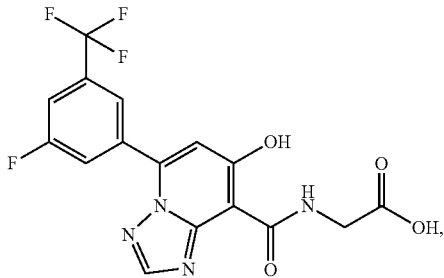

or a pharmaceutically acceptable salt thereof, or a solvate thereof.

[23] A compound represented by the following formula:

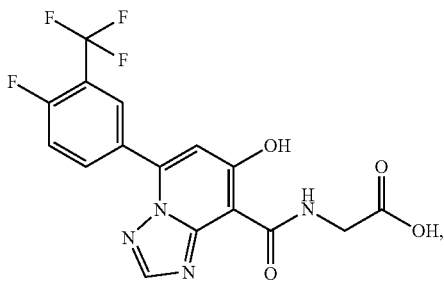

or a pharmaceutically acceptable salt thereof, or a solvate thereof.

[24] A compound represented by the following formula:

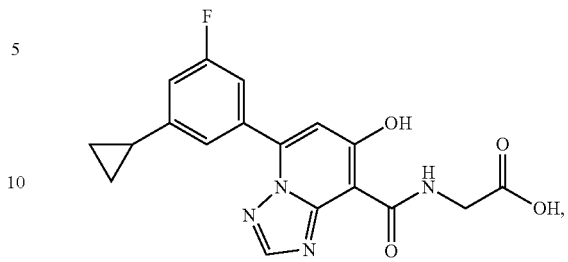

or a pharmaceutically acceptable salt thereof, or a solvate thereof.

[25] A compound represented by the following formula:

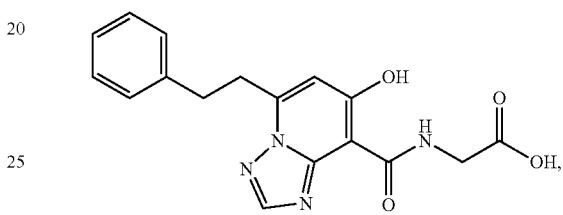

or a pharmaceutically acceptable salt thereof, or a solvate thereof.

[26] A pharmaceutical composition comprising the compound described in any of the above-mentioned [1] to [25], or a pharmaceutically acceptable salt thereof, or a solvate thereof, and a pharmaceutically acceptable carrier (hereinafter to be also referred to as "the pharmaceutical composition of the present invention").

[27] A prolyl hydroxylase inhibitor comprising the compound described in any of the above-mentioned [1] to [25], or a pharmaceutically acceptable salt thereof, or a solvate thereof.

[28] An erythropoietin production-inducing agent comprising the compound described in any of the above-mentioned [1] to [25], or a pharmaceutically acceptable salt thereof, or a solvate thereof.

[29] A therapeutic agent for anemia comprising the compound described in any of the above-mentioned [1] to [25], or a pharmaceutically acceptable salt thereof, or a solvate thereof.

[30] A therapeutic agent for renal anemia comprising the compound described in any of the above-mentioned [1] to [25], or a pharmaceutically acceptable salt thereof, or a solvate thereof.

[31] Use of the compound described in any of the above-mentioned [1] to [25], or a pharmaceutically acceptable salt thereof, or a solvate thereof, for the production of a prolyl hydroxylase inhibitor.

[32] Use of the compound described in any of the above-mentioned [1] to [25], or a pharmaceutically acceptable salt thereof, or a solvate thereof, for the production of an erythropoietin production-inducing agent.

[33] Use of the compound described in any of the above-mentioned [1] to [25], or a pharmaceutically acceptable salt thereof, or a solvate thereof, for the production of a therapeutic agent for anemia.

[34] Use of the compound described in any of the above-mentioned [1] to [25], or a pharmaceutically acceptable salt thereof, or a solvate thereof, for the production of a therapeutic agent for renal anemia.

[35] A method of inhibiting prolyl hydroxylase, comprising administering an effective amount of the compound described in any of the above-mentioned [1] to [25], or a pharmaceutically acceptable salt thereof, or a solvate thereof to a mammal.
[36] A method of inducing erythropoietin production, comprising administering an effective amount of the compound described in any of the above-mentioned [1] to [25], or a pharmaceutically acceptable salt thereof, or a solvate thereof to a mammal.
[37] A method of treating anemia, comprising administering an effective amount of the compound described in any of the above-mentioned [1] to [25], or a pharmaceutically acceptable salt thereof, or a solvate thereof to a mammal.
[38] A method of treating renal anemia, comprising administering an effective amount of the compound described in any of the above-mentioned [1] to [25], or a pharmaceutically acceptable salt thereof, or a solvate thereof to a mammal.
[39] A commercial package comprising the pharmaceutical composition described in the above-mentioned [26] and a written matter associated therewith, the written matter stating that the pharmaceutical composition can or should be used for the treatment or prophylaxis of a disease selected from anemia and renal anemia.
[40] A kit comprising the pharmaceutical composition described in the above-mentioned [26] and a written matter associated therewith, the written matter stating that the pharmaceutical composition can or should be used for the treatment or prophylaxis of a disease selected from anemia and renal anemia.

DETAILED DESCRIPTION OF THE INVENTION

The definition of each substituent or each moiety to be used in the present specification is as follows.

The "halogen atom" is a fluorine atom, a chlorine atom, a bromine atom or an iodine atom.

The "$C_{1-10}$ alkyl group" is a straight chain or branched chain alkyl group having a carbon number of 1 to 10, preferably a straight chain or branched chain alkyl group having a carbon number of 1 to 7. For example, a methyl group, an ethyl group, a propyl group, an isopropyl group, a butyl group, an isobutyl group, a sec-butyl group, a tert-butyl group, a pentyl group, an isopentyl group, a tert-pentyl group, an 1-ethylpropyl group, a neopentyl group, a hexyl group, a 2-ethylbutyl group, a 3,3-dimethylbutyl group, a 3,3-dimethylpentyl group, a heptyl group, an octyl group, a nonyl group, a decyl group and the like can be mentioned.

The "$C_{1-6}$ alkyl group" is a straight chain or branched chain alkyl group having a carbon number of 1 to 6, preferably a straight chain or branched chain alkyl group having a carbon number of 1 to 3. For example, those exemplified as the above-mentioned "$C_{1-10}$ alkyl group" and having a carbon number of 1 to 6 can be mentioned.

The "$C_{1-3}$ alkyl group" is a straight chain or branched chain alkyl group having a carbon number of 1 to 3. For example, those exemplified as the above-mentioned alkyl group and having a carbon number of 1 to 3 can be mentioned.

The "$C_{6-14}$ aryl group" is an aromatic hydrocarbon group having a carbon number of 6 to 14. For example, a phenyl group, a naphthyl group, an anthryl group, an indenyl group, an azulenyl group, a fluorenyl group, a phenanthryl group, a pentalenyl group and the like can be mentioned, with preference given to a phenyl group.

The "$C_{3-8}$ cycloalkyl group" is a saturated cycloalkyl group having a carbon number of 3 to 8, preferably 3 to 5, and, for example, a cyclopropyl group, a cyclobutyl group, a cyclopentyl group, a cyclohexyl group, a cycloheptyl group, a cyclooctyl group and the like can be mentioned.

The "$C_{3-5}$ cycloalkyl group" is a saturated cycloalkyl group having a carbon number of 3 to 5. For example, those exemplified as the above-mentioned "$C_{3-8}$ cycloalkyl group" and having a carbon number of 3 to 5 can be mentioned.

The "$C_{6-14}$ aryl-$C_{1-6}$ alkyl group" is a $C_{6-14}$ aryl-$C_{1-6}$ alkyl group wherein the $C_{6-14}$ aryl moiety thereof is the "$C_{6-14}$ aryl group" defined above and the $C_{1-6}$ alkyl moiety thereof is the "$C_{1-6}$ alkyl group" defined above, with preference given to a $C_{6-14}$ aryl-$C_{1-6}$ alkyl group wherein the $C_{1-6}$ alkyl moiety is a straight chain $C_{1-6}$ alkyl group. Examples of the $C_{6-14}$ aryl-$C_{1-6}$ alkyl group include a phenylmethyl group, a phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group, an anthrylmethyl group, an indenylmethyl group, an azulenylmethyl group, a fluorenylmethyl group, a phenanthrylmethyl group, a pentalenylmethyl group and the like.

The "$C_{3-8}$ cycloalkyl-$C_{1-8}$ alkyl group" is a $C_{3-8}$ cycloalkyl-$C_{1-6}$ alkyl group wherein the $C_{3-8}$ cycloalkyl moiety thereof is the "$C_{3-8}$ cycloalkyl group" defined above and the $C_{1-6}$ alkyl moiety thereof is the "$C_{1-8}$ alkyl group" defined above. Examples thereof include a cyclopropylmethyl group, a cyclopropylethyl group, a cyclopropylpropyl group, a cyclopropylbutyl group, a cyclopropylpentyl group, a cyclopropylhexyl group, a cyclobutylmethyl group, a cyclobutylethyl group, a cyclobutylpropyl group, a cyclobutylbutyl group, a cyclobutylpentyl group, a cyclobutylhexyl group, a cyclopentylmethyl group, a cyclopentylethyl group, a cyclopentylpropyl group, a cyclopentylbutyl group, a cyclopentylpentyl group, a cyclopentylhexyl group, a cyclohexylmethyl group, a cyclohexylethyl group, a cyclohexylpropyl group, a cyclohexylbutyl group, a cyclohexylpentyl group, a cyclohexylhexyl group, a cycloheptylmethyl group, a cycloheptylethyl group, a cycloheptylpropyl group, a cycloheptylbutyl group, a cycloheptylpentyl group, a cycloheptylhexyl group, a cyclooctylmethyl group, a cyclooctylethyl group, a cyclooctylpropyl group, a cyclooctylbutyl group, a cyclooctylpentyl group, a cyclooctylhexyl group and the like.

The "$C_{3-8}$ cycloalkenyl group" is a cycloalkenyl group having a carbon number of 3 to 8 and contains at least one, preferably 1 or 2, double bonds. For example, a cyclopropenyl group, a cyclobutenyl group, a cyclopentenyl group, a cyclopentadienyl group, a cyclohexenyl group, a cyclohexadienyl group (a 2,4-cyclohexadien-1-yl group, a 2,5-cyclohexadien-1-yl group etc.), a cycloheptenyl group, a cyclooctenyl group and the like can be mentioned.

The "heteroaryl group" is an aromatic heterocycle having, as ring-constituting atom besides carbon atom, 1 to 6 hetero atoms selected from nitrogen atom, oxygen atom and sulfur atom, wherein the number of ring-constituting atom is 3 to 14, including monocycle and fused ring.

The "monocyclic heteroaryl group" is a monocyclic heteroaryl group preferably having 1 to 4 hetero atoms and, for example, a thienyl group (e.g., thiophen-2-yl, thiophen-3-yl), a furyl group (e.g., furan-2-yl, furan-3-yl etc.), a pyrrolyl group (e.g., 2-Pyrroline-1-yl group, 3-Pyrroline-3-yl etc.), an oxazolyl group (e.g., oxazol-2-yl, oxazol-4-yl, oxazol-5-yl etc.), an isoxazolyl group (e.g., isoxazol-3-yl, isoxazol-4-yl, isoxazol-5-yl etc.), a thiazolyl group (e.g., thiazol-2-yl, thiazol-4-yl, thiazol-5-yl etc.), an isothiazolyl group (e.g., isothiazol-3-yl, isothiazol-4-yl, isothiazol-5-yl etc.), an imidazolyl group (e.g., imidazol-1-yl, 1H-imidazol-2-yl, 1H-imidazol-4-yl etc.), a pyrazolyl group (e.g., pyrazol-1-yl, 1H-pyrazol-3-yl, 2H-pyrazol-3-yl, 1H-pyrazol-4-yl etc.), an oxadiazolyl group (e.g., 1,3,4-oxadiazol-2-yl, 1,2,3-oxadiazol-4-yl, 1,2,4-oxadiazol-3-yl, 1,2,4-oxadiazol-5-yl, 1,2,5-oxadiazol-3-yl etc.), a thiadiazolyl group (e.g., 1,3,4-thiadiazol-2-yl, 1,2,3-thiadiazol-4-yl, 1,2,3-thiadiazol-5-yl, 1,2,5-thiadiazol-3-yl etc.), a triazolyl group (e.g., 1,2,4-triazol-3-yl, 1,2,4-triazol-1-yl, 1,2,3-triazol-1-yl, 1,2,3-triazol-2-yl, 1,3,4-triazol-1-yl etc.), a tetrazolyl group (e.g., tetrazol-1-yl, tetrazol-2-yl, 1H-tetrazol-5-yl, 2H-tetrazol-5-yl etc.), a pyridyl group (e.g., pyridin-2-yl, pyridin-3-yl, pyridin-4-yl etc.), a pyrimidinyl group (e.g., pyrimidin-2-yl, pyrimidin-4-yl, pyrimidin-5-yl etc.), a pyridazinyl group (e.g., pyridazin-3-yl, pyridazin-4-yl etc.), a pyrazinyl group (e.g., pyrazin-2-yl etc.), a triazinyl group (e.g., 1,3,5-triazin-2-yl etc.) and the like can be mentioned.

Examples of the "fused heteroaryl group" include a quinolyl group, an isoquinolyl group, a quinazolinyl group, a quinoxalyl group, a phthalazinyl group, a cinnolinyl group, a naphthyridinyl group, an indolyl group, a benzimidazolyl group, an indolinyl group, a benzofuranyl group, a benzothienyl group, a benzoxazolyl group, a benzothiazolyl group, a benzodioxinyl group, a benzothiazolyl group, a tetrahydroquinolyl group, a dihydrobenzofuranyl group, a dihydrobenzothienyl group, a dihydrobenzodioxinyl group, an indenothiazolyl group, a tetrahydrobenzothiazolyl group, a 5,7-dihydropyrrolo[3,4-d]pyrimidinyl group, a 6,7-dihydro-5H-cyclopentapyrimidinyl group, an imidazo[2,1-b]thiazolyl group, a pteridinyl group, a purinyl group and the like.

The "halo-$C_{1-6}$ alkyl group" is a "$C_{1-6}$ alkyl group" defined above, which is substituted by the same or different 1 to 5 halogen atoms, and, for example, chloromethyl, fluoromethyl, difluoromethyl, trifluoromethyl, bromomethyl, chloroethyl, fluoroethyl, bromoethyl, chloropropyl, fluoropropyl, bromopropyl and the like can be mentioned.

The "group B" includes the following substituent groups (a) to (e).
(a) the "halogen atom" defined above,
(b) the "$C_{1-6}$ alkyl group" defined above,
(c) the "$C_{3-8}$ cycloalkyl group" defined above,
(d) a cyano group, and
(e) the "halo-$C_{1-6}$ alkyl group" defined above.

The "$C_{6-14}$ aryl group optionally substituted by the same or different 1 to 5 substituents selected from group B" is the "$C_{6-14}$ aryl group" defined above, which is optionally substituted by the same or different 1 to 5 substituents, and includes unsubstituted $C_{8-14}$ aryl group. The substituents are the same or different and selected from the "group B" defined above.

The "$C_{3-8}$ cycloalkyl group optionally substituted by the same or different 1 to 5 substituents selected from group B" is the "$C_{3-8}$ cycloalkyl group" defined above which is optionally substituted by the same or different 1 to 5 substituents, and includes unsubstituted $C_{3-8}$ cycloalkyl group. The substituents are the same or different and selected from the "group B" defined above.

The "$C_{3-8}$ cycloalkenyl group optionally substituted by the same or different 1 to 5 substituents selected from group B" is the "$C_{3-8}$ cycloalkenyl group" defined above which is optionally substituted by the same or different 1 to 5 substituents, and includes unsubstituted $C_{3-8}$ cycloalkenyl group. The substituents are the same or different and selected from the "group B" defined above.

The "heteroaryl group optionally substituted by the same or different 1 to 5 substituents selected from group B" is the "heteroaryl group" defined above which is optionally substituted by the same or different 1 to 5 substituents, and includes unsubstituted heteroaryl group. The substituents are the same or different and selected from the "group B" defined above.

In the above-mentioned formula [I], preferable groups are as described below.
The partial structural formula:

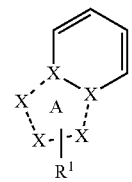

is a group represented by any of the following formulas:

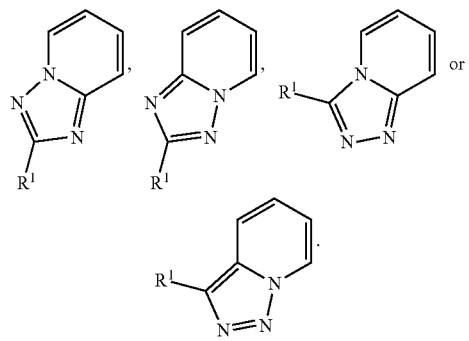

As the partial structural formula, preferred are groups represented by

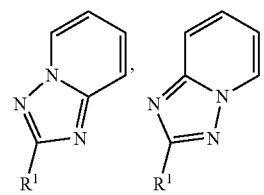

and the like.

As the partial structural formula, more preferred is a group represented by

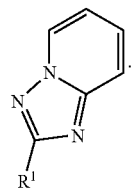

$R^1$ is
(1) a hydrogen atom,
(2) a $C_{1-6}$ alkyl group,
(3) a $C_{6-14}$ aryl group,
(4) a $C_{3-8}$ cycloalkyl group,
(5) a $C_{6-14}$ aryl-$C_{1-6}$ alkyl group, or
(6) a $C_{3-8}$ cycloalkyl-$C_{1-6}$ alkyl group.
$R^1$ is preferably
(1) a hydrogen atom,
(2) a $C_{1-3}$ alkyl group (e.g., methyl),
(3) a $C_{6-14}$ aryl group (e.g., phenyl), (4) a $C_{3-6}$ cycloalkyl group (e.g., cyclopropyl),
(5) a $C_{6-44}$ aryl (e.g., phenyl)-$C_{1-3}$ alkyl (preferably straight chain $C_{1-3}$ alkyl, e.g., ethyl) group,
(6) a $C_{3-8}$ cycloalkyl (e.g., cyclohexyl)-$C_{1-3}$ alkyl (e.g., ethyl) group, or the like.

$R^1$ is more preferably a hydrogen atom.

$R^2$ is
(1) a hydrogen atom,
(2) a $C_{1-10}$ alkyl group,
(3) a $C_{6-14}$ aryl group optionally substituted by the same or different 1 to 5 substituents selected from the above-mentioned group B,
(4) a $C_{3-8}$ cycloalkyl group optionally substituted by the same or different 1 to 5 substituents selected from the above-mentioned group B,
(5) a $C_{3-6}$ cycloalkenyl group optionally substituted by the same or different 1 to 5 substituents selected from the above-mentioned group B,
(6) a heteroaryl group optionally substituted by the same or different 1 to 5 substituents selected from the above-mentioned group B (wherein the heteroaryl has, besides carbon atom, 1 to 6 hetero atoms selected from nitrogen atom, oxygen atom and sulfur atom),
(7) a $C_{6-14}$ aryl-$C_{1-6}$ alkyl group (wherein $C_{6-14}$ aryl is optionally substituted by the same or different 1 to 5 substituents selected from the above-mentioned group B), or
(8) a $C_{3-8}$ cycloalkyl-$C_{1-6}$ alkyl group (wherein $C_{3-8}$ cycloalkyl is optionally substituted by the same or different 1 to 5 substituents selected from the above-mentioned group B).

$R^2$ is preferably
(1) a hydrogen atom,
(2) a $C_{1-10}$ alkyl group,
(3) a $C_{6-14}$ aryl group optionally substituted by the same or different 1 to 5 substituents selected from the above-mentioned group B,
(4) a $C_{3-8}$ cycloalkyl group (e.g., cyclopentyl, cyclohexyl, cycloheptyl),
(5) a $C_{3-8}$ cycloalkenyl group (e.g., cyclohexenyl),
(6) a heteroaryl group (preferably monocyclic heteroaryl group, e.g., thienyl) optionally substituted by the same or different 1 to 5 (e.g., 1) substituents selected from the above-mentioned group B
(e.g., (a) a halogen atom (e.g., chlorine atom), and
  (b) a $C_{1-6}$ alkyl group (e.g., methyl))
(wherein the heteroaryl has, besides carbon atom, 1 to 6 (e.g., 1 to 4) hetero atoms selected from nitrogen atom, oxygen atom and sulfur atom (e.g., a sulfur atom)),
(7) a $C_{6-14}$ aryl-$C_{1-6}$ alkyl group (wherein $C_{6-14}$ aryl is optionally substituted by the same or different 1 to 5 substituents selected from the above-mentioned group B), or
(8) a $C_{3-8}$ cycloalkyl-$C_{1-3}$ alkyl group (wherein $C_{3-8}$ cycloalkyl is optionally substituted by the same or different 1 to 5 substituents selected from the above-mentioned group B).

$R^2$ is more preferably
(1) a $C_{1-10}$ alkyl group (e.g., ethyl, propyl, isopropyl, butyl, isobutyl, pentyl, isopentyl, tert-pentyl, hexyl, 1-ethylpropyl, 2-ethylbutyl, 3,3-dimethylbutyl, 3,3-dimethylpentyl),
(2) a $C_{6-44}$ aryl group (e.g., phenyl) optionally substituted by the same or different 1 to 5 (e.g., 1 to 3) substituents selected from the above-mentioned group B
(e.g., (a) a halogen atom (e.g., chlorine atom, fluorine atom),
  (b) a $C_{1-3}$ alkyl group (e.g., methyl),
  (c) a $C_{3-5}$ cycloalkyl group (e.g., cyclopropyl),
  (d) a cyano group, and
  (e) a halo-$C_{1-3}$ alkyl group (e.g., trifluoromethyl)),
(3) a $C_{6-14}$ aryl (e.g., phenyl)-$C_{1-6}$ alkyl (preferably straight chain $C_{1-6}$ alkyl, e.g., methyl, ethyl, propyl) group
(the $C_{6-14}$ aryl is optionally substituted by the same or different 1 to 5 (e.g., 1 to 3) substituents selected from the above-mentioned group B
(e.g., (a) a halogen atom (e.g., chlorine atom, fluorine atom),
  (b) a $C_{3-8}$ cycloalkyl group (e.g., cyclopropyl), and
  (c) a halo-$C_{1-3}$ alkyl group (e.g., trifluoromethyl))), or
(4) a $C_{3-8}$ cycloalkyl (e.g., cyclopropyl, cyclobutyl, cyclopentyl, cyclohexyl)-$C_{1-3}$ alkyl (e.g., methyl, ethyl) group
(the $C_{3-8}$ cycloalkyl is optionally substituted by the same or different 1 to 5 substituents selected from the above-mentioned group B).

$R^2$ is still more preferably
(1) a $C_{1-6}$ alkyl group (e.g., butyl, pentyl, 1-ethylpropyl),
(2) phenyl optionally substituted the same or different 1 to 3 substituents selected from
  (a) a halogen atom (e.g., chlorine atom, fluorine atom),
  (b) a $C_{1-3}$ alkyl group (e.g., methyl),
  (c) a $C_{3-5}$ cycloalkyl group (e.g., cyclopropyl), and
  (d) a halo-$C_{1-3}$ alkyl group (e.g., trifluoromethyl),
(3) phenylethyl, or
(4) cyclopentylethyl.

$R^2$ is particularly preferably butyl, phenylethyl or 4-fluoro-3-trifluoromethylphenyl.

In another embodiment of the present invention, $R^2$ is preferably
(1) a $C_{1-10}$ alkyl group, or
(2) a $C_{6-14}$ aryl-$C_{1-6}$ alkyl group (wherein $C_{6-14}$ aryl is optionally substituted by the same or different 1 to 5 substituents selected from the above-mentioned group B).

$R^3$ is
(1) a hydrogen atom,
(2) a halogen atom,
(3) a $C_{1-8}$ alkyl group,
(4) a $C_{8-14}$ aryl group,
(5) a $C_{3-8}$ cycloalkyl group, or
(6) a $C_{8-14}$ aryl-$C_{1-6}$ alkyl group.

$R^3$ is preferably
(1) a hydrogen atom,
(2) a halogen atom (e.g., chlorine atom),
(3) a $C_{1-8}$ alkyl group (e.g., ethyl, pentyl),
(4) a $C_{8-14}$ aryl group (e.g., phenyl), or
(5) a $C_{8-14}$ aryl (e.g., phenyl)-$C_{1-6}$ alkyl (preferably straight chain $C_{1-8}$ alkyl, e.g., ethyl) group.

$R^3$ is more preferably a hydrogen atom.

$R^4$ and $R^5$ are each independently
(1) a hydrogen atom, or
(2) a $C_{1-8}$ alkyl group.

$R^4$ and $R^5$ are preferably each independently
(1) a hydrogen atom, or
(2) a $C_{1-3}$ alkyl group (e.g., methyl).

$R^4$ and $R^5$ are more preferably both hydrogen atoms.

In the formula [I], a compound represented by the following formula [Ia]

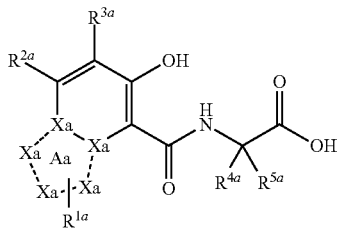

wherein
the partial structural formula:

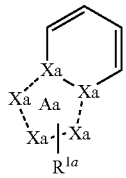

is a group represented by

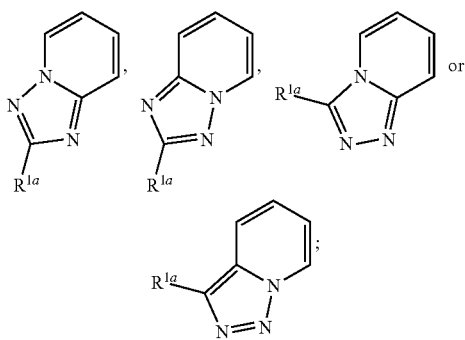

$R^{1a}$ is
(1) a hydrogen atom,
(2) a $C_{1-3}$ alkyl group (e.g., methyl),
(3) a $C_{6-14}$ aryl group (e.g., phenyl),
(4) a $C_{3-5}$ cycloalkyl group (e.g., cyclopropyl),
(5) a $C_{5-14}$ aryl (e.g., phenyl)-$C_{1-3}$ alkyl (preferably straight chain $C_{1-3}$ alkyl, e.g., ethyl) group, or
(6) a $C_{3-8}$ cycloalkyl (e.g., cyclohexyl)-$C_{1-3}$ alkyl (e.g., ethyl) group;
$R^{2a}$ is
(1) a hydrogen atom,
(2) a $C_{1-10}$ alkyl group,
(3) a $C_{6-14}$ aryl group optionally substituted by the same or different 1 to 5 substituents selected from the above-mentioned group B,
(4) a $C_{3-8}$ cycloalkyl group (e.g., cyclopentyl, cyclohexyl, cycloheptyl),
(5) a $C_{3-8}$ cycloalkenyl group (e.g., cyclohexenyl),
(6) a heteroaryl group (preferably monocyclic heteroaryl group, e.g., thienyl) optionally substituted by the same or different 1 to 5 (e.g., 1) substituents selected from the above-mentioned group B
(e.g., (a) a halogen atom (e.g., chlorine atom), and
(b) a $C_{1-6}$ alkyl group (e.g., methyl))
(wherein the heteroaryl has, besides carbon atom, 1 to 6 (e.g., 1 to 4) hetero atoms selected from nitrogen atom, oxygen atom and sulfur atom (e.g., a sulfur atom)),
(7) a $C_{6-14}$ aryl-$C_{1-6}$ alkyl group (wherein $C_{6-14}$ aryl is optionally substituted by the same or different 1 to 5 substituents selected from the above-mentioned group B), or
(8) a $C_{3-8}$ cycloalkyl-$C_{1-3}$ alkyl group (wherein $C_{3-8}$ cycloalkyl is optionally substituted by the same or different 1 to 5 substituents selected from the above-mentioned group B);
$R^{3a}$ is
(1) a hydrogen atom,
(2) a halogen atom (e.g., chlorine atom),
(3) a $C_{1-6}$ alkyl group (e.g., ethyl, pentyl),
(4) a $C_{6-14}$ aryl group (e.g., phenyl), or
(5) a $C_{6-14}$ aryl (e.g., phenyl)-$C_{1-6}$ alkyl (preferably straight chain $C_{1-6}$ alkyl, e.g., ethyl) group; and
$R^{4a}$ and $R^{5a}$ are each independently
(1) a hydrogen atom, or
(2) a $C_{1-3}$ alkyl group (e.g., methyl)]
is more preferable.

As the compound of the present invention, a compound represented by the above-mentioned formula [Ia], wherein
$R^{1a}$ is a hydrogen atom;
$R^{2a}$
(1) a $C_{1-10}$ alkyl group (e.g., ethyl, propyl, isopropyl, butyl, isobutyl, pentyl, isopentyl, tert-pentyl, hexyl, 1-ethylpropyl, 2-ethylbutyl, 3,3-dimethylbutyl, 3,3-dimethylpentyl),
(2) a $C_{6-14}$ aryl group (e.g., phenyl) optionally substituted by the same or different 1 to 5 (e.g., 1 to 3) substituents selected from the above-mentioned group B
(e.g., (a) a halogen atom (e.g., chlorine atom, fluorine atom),
(b) a $C_{1-3}$ alkyl group (e.g., methyl),
(c) a $C_{3-6}$ cycloalkyl group (e.g., cyclopropyl),
(d) a cyano group, and
(e) a halo-$C_{1-3}$ alkyl group (e.g., trifluoromethyl)),
(3) a $C_{6-14}$ aryl (e.g., phenyl)-$C_{1-6}$ alkyl (preferably straight chain $C_{1-6}$ alkyl, e.g., methyl, ethyl, propyl) group
(the $C_{6-14}$ aryl is optionally substituted by the same or different 1 to 5 (e.g., 1 to 3) substituents selected from the above-mentioned group B
(e.g., (a) a halogen atom (e.g., chlorine atom, fluorine atom),
(b) a $C_{3-8}$ cycloalkyl group (e.g., cyclopropyl), and
(c) a halo-$C_{1-6}$ alkyl group (e.g., trifluoromethyl))), or
(4) a $C_{3-8}$ cycloalkyl (e.g., cyclopropyl, cyclobutyl, cyclopentyl, cyclohexyl)-$C_{1-3}$ alkyl (e.g., methyl, ethyl) group
(the $C_{3-8}$ cycloalkyl is optionally substituted by the same or different 1 to 5 substituents selected from the above-mentioned group B);
$R^{3a}$ is a hydrogen atom; and
$R^{4a}$ and $R^{5a}$ are both hydrogen atoms;
is more preferable.

In another embodiment of the present invention, from compounds represented by the formula [I], a compound represented by the following formula [I-1]:

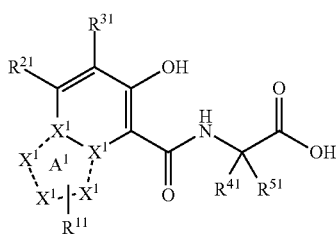

wherein
the partial structural formula:

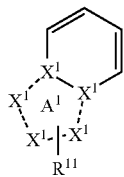

is a group represented by any of the following formulas:

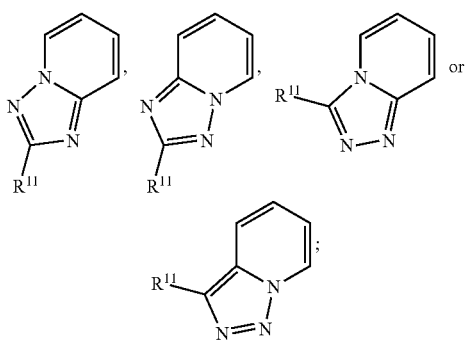

$R^{11}$ is
(1) a hydrogen atom,
(2) a $C_{1-8}$ alkyl group (e.g., methyl),
(3) a phenyl group,
(4) a $C_{3-8}$ cycloalkyl group (e.g., cyclopropyl),
(5) a phenyl-$C_{1-6}$ alkyl group, or
(6) a $C_{3-8}$ cycloalkyl-$C_{1-6}$ alkyl group;
$R^{21}$ is
(1) a hydrogen atom,
(2) a $C_{1-10}$ alkyl group (e.g., ethyl, n-propyl, isopropyl, n-butyl, isobutyl, n-pentyl, n-hexyl, 1-ethylpropyl, 3-methylbutyl, 2,2-dimethylpropyl, 3,3-dimethylbutyl, 2-ethylbutyl, 3,3-dimethylpentyl),
(3) a phenyl group optionally substituted by the same or different 1 to 5 substituents (e.g., fluorine atom, chlorine atom, methyl, cyano, cyclopropyl, trifluoromethyl) selected from the above-mentioned group B,
(4) a $C_{3-8}$ cycloalkyl group (e.g., cyclopentyl, cyclohexyl, cycloheptyl),
(5) a $C_{3-8}$ cycloalkenyl group (e.g., cyclohexenyl),
(6) a thienyl group optionally substituted by the same or different 1 to 5 substituents (e.g., chlorine atom, methyl) selected from the above-mentioned group B,
(7) a phenyl-$C_{1-6}$ alkyl group (e.g., phenylmethyl, phenylethyl, phenylpropyl) (wherein phenyl is optionally substituted by the same or different 1 to 5 substituents (e.g., fluorine atom, chlorine atom, cyclopropyl, trifluoromethyl) selected from the above-mentioned group B), or
(8) a $C_{3-8}$ cycloalkyl-$C_{1-6}$ alkyl group (e.g., cyclobutylmethyl, cyclopentylmethyl, cyclohexylmethyl, cyclopropylethyl, cyclobutylethyl, cyclopentylethyl, cyclohexylethyl);
$R^{31}$ is
(1) a hydrogen atom,
(2) a halogen atom (e.g., chlorine atom),
(3) a $C_{1-8}$ alkyl group (e.g., ethyl, n-pentyl),
(4) a phenyl group,
(5) a $C_{3-8}$ cycloalkyl group, or
(6) a phenyl-$C_{1-6}$ alkyl group (e.g., phenylethyl); and
$R^{41}$ and $R^{51}$ are each independently
(1) a hydrogen atom, or
(2) a $C_{1-6}$ alkyl group (e.g., methyl)
is preferable.

Of compounds represented by the formula [I-1], a compound wherein
$R^{11}$ is
(1) a hydrogen atom,
(2) a $C_{1-6}$ alkyl group (e.g., methyl),
(3) a phenyl group, or
(4) a $C_{3-8}$ cycloalkyl group (e.g., cyclopropyl);
$R_{21}$ is
(1) a hydrogen atom,
(2) a $C_{1-10}$ alkyl group (e.g., ethyl, n-propyl, isopropyl, n-butyl, isobutyl, n-pentyl, n-hexyl, 1-ethylpropyl, 3-methylbutyl, 2,2-dimethylpropyl, 3,3-dimethylbutyl, 2-ethylbutyl, 3,3-dimethylpentyl),
(3) a phenyl group optionally substituted by the same or different 1 to 5 substituents (e.g., fluorine atom, chlorine atom, methyl, cyano, cyclopropyl, trifluoromethyl) selected from the above-mentioned group B,
(4) a $C_{3-8}$ cycloalkyl group (e.g., cyclopentyl, cyclohexyl, cycloheptyl),
(5) a $C_{3-8}$ cycloalkenyl group (e.g., cyclohexenyl),
(6) a thienyl group optionally substituted by the same or different 1 to 5 substituents (e.g., chlorine atom, methyl) selected from the above-mentioned group B,
(7) a phenyl-$C_{1-6}$ alkyl group (e.g., phenylmethyl, phenylethyl, phenylpropyl) (wherein phenyl is optionally substituted by the same or different 1 to 5 substituents (e.g., fluorine atom, chlorine atom, cyclopropyl, trifluoromethyl) selected from the above-mentioned group B), or
(8) a $C_{3-6}$ cycloalkyl-$C_{1-5}$ alkyl group (e.g., cyclobutylmethyl, cyclopentylmethyl, cyclohexylmethyl, cyclopropylethyl, cyclobutylethyl, cyclopentylethyl, cyclohexylethyl);
$R^{31}$ is
(1) a hydrogen atom,
(2) a halogen atom (e.g., chlorine atom),
(3) a $C_{1-6}$ alkyl group (e.g., ethyl, n-pentyl),
(4) a phenyl group, or
(6) a phenyl-$C_{1-6}$ alkyl group (e.g., phenylethyl);
$R^{41}$ and $R^{51}$ are each independently
(1) a hydrogen atom, or
(2) a $C_{1-6}$ alkyl group (e.g., methyl),
is preferable,
$R^{11}$ is a hydrogen atom, methyl, phenyl, or cyclopropyl;
$R^{21}$ is a hydrogen atom; ethyl, n-propyl, isopropyl, n-butyl, isobutyl, n-pentyl, n-hexyl, 1-ethylpropyl, 3-methylbutyl, 2,2-dimethylpropyl, 3,3-dimethylbutyl, 2-ethylbutyl, 3,3-dimethylpentyl; phenyl optionally substituted by the same or different 1 to 5 substituents selected from fluorine atom, chlorine atom, methyl, cyano, cyclopropyl and trifluoromethyl; cyclopentyl, cyclohexyl, cycloheptyl; cyclohexenyl; thienyl optionally substituted by the same or different 1 to 5 substituents selected from chlorine atom and methyl; phenylmethyl, phenylethyl, phenylpropyl (the phenyl is optionally substituted by the same or different 1 to 5 substituents selected from fluorine atom, chlorine atom, cyclopropyl and trifluoromethyl); cyclobutylmethyl, cyclopentylmethyl, cyclohexylmethyl, cyclopropylethyl, cyclobutylethyl, cyclopentylethyl, or cyclohexylethyl;
$R^{31}$ is a hydrogen atom, a chlorine atom, ethyl, n-pentyl, phenyl, or phenylethyl; and
$R^{41}$ and $R^{51}$ is are each independently a hydrogen atom or methyl,
is more preferable.

As the compound of the present invention or a pharmaceutically acceptable salt thereof, or a solvate thereof, the compounds described in Examples 1-122 are preferable, the compounds described in Examples 1, 2, 21, 31, 40, 44, 47, 52, 60, 74, 79, 116, 118, 119, 120, 121 and 122 are particularly preferable.

A pharmaceutically acceptable salt of the compound represented by the formula [I] may be any salt as long as it forms a nontoxic salt with the compound of the present invention. Examples thereof include salts with inorganic acids, salts with organic acids, salts with inorganic bases, salts with organic bases, salts with amino acids and the like.

Examples of the salt with inorganic acid include a salt with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with inorganic base include sodium salt, potassium salt, calcium salt, magnesium salt, ammonium salt and the like.

Examples of the salt with organic base include methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with amino acid include salts with lysine, arginine, aspartic acid, glutamic acid and the like.

Each salt can be obtained by reacting a compound represented by the formula [I] with an inorganic base, organic base, inorganic acid, organic acid or amino acid according to a known method.

The "solvate" is a compound represented by the formula [I] or a pharmaceutically acceptable salt thereof wherein a molecule of the solvent is coordinated, and also includes hydrates. As the solvate, a pharmaceutically acceptable solvate is preferable and includes, for example, hydrate, ethanolate, dimethylsulfoxidate and the like of the compound represented by the formula [I] or a pharmaceutically acceptable salt thereof. Specific examples thereof include hemihydrate, monohydrate, dihydrate and monoethanolate of the compound represented by the formula [I], monohydrate of sodium salt, 2/3 ethanolate of dihydrochloride, and the like of the compound represented by the formula [I].

The solvate of the compound of the present invention or a pharmaceutically acceptable salt thereof can be obtained according to a method known per se.

In addition, the compound represented by the formula [1] or a pharmaceutically acceptable salt thereof, or a solvate thereof has various isomers. For example, E form and Z form are present as geometric isomers, when an asymmetric carbon atom is present, enantiomer and diastereomer are present as stereoisomers based thereon, and when axial chirality is present, stereoisomers based thereon are present. Moreover, tautomers can also be present. Accordingly, the present invention encompasses all these isomers and mixtures thereof.

In addition, the compound of the present invention or a pharmaceutically acceptable salt thereof, or a solvate thereof may be labeled with an isotope (e.g., $^3$H, $^{14}$C, $^{35}$S etc.).

As the compound represented by the formula [I] or a pharmaceutically acceptable salt thereof or a solvate thereof, a compound represented by the formula [I] or a pharmaceutically acceptable salt thereof or a solvate thereof, each of which is substantially purified, is preferable. More preferred is a compound represented by the formula [I] or a pharmaceutically acceptable salt thereof or a solvate thereof, each of which is purified to have a purity usable as a pharmaceutical product.

In the present invention, a prodrug of the compound represented by the formula [I] can also be a useful medicament. The "prodrug" is a derivative of the compound of the present invention having a chemically or metabolically degradable group which, after administration to the body, restores to the original compound by, for example, hydrolysis, solvolysis or decomposition under physiological conditions, and shows inherent efficacy. It includes a noncovalent complex, and a salt. Prodrug is utilized for, for example, improvement of absorption on oral administration, or targeting to a target moiety.

Examples of the modified moiety include, in the compound of the present invention, a highly reactive functional group such as a hydroxyl group, a carboxyl group, an amino group and the like.

Specific examples of the hydroxyl-modifying group include an acetyl group, a propionyl group, an isobutyryl group, a pivaloyl group, a palmitoyl group, a benzoyl group, a 4-methylbenzoyl group, a dimethylcarbamoyl group, a dimethylaminomethylcarbonyl group, a sulfo group, an alanyl group, a fumaryl group and the like. In addition, sodium salt of 3-carboxybenzoyl group, 2-carboxyethylcarbonyl group and the like can be mentioned.

Specific examples of the carboxyl-modifying group include a methyl group, an ethyl group, a propyl group, an isopropyl group, a butyl group, an isobutyl group, a tert-butyl group, a pivaloyloxymethyl group, a carboxymethyl group, a dimethylaminomethyl group, a 1-(acetyloxy)ethyl group, a 1-(ethoxycarbonyloxy)ethyl group, a 1-(isopropyloxycarbonyloxy)ethyl group, a 1-(cyclohexyloxycarbonyloxy)ethyl group, a (5-methyl-2-oxo-1,3-dioxol-4-yl)methyl group, a benzyl group, a phenyl group, an o-tolyl group, a morpholinoethyl group, an N,N-diethylcarbamoylmethyl group, a phthalidyl group and the like.

Specific examples of the amino-modifying group include a tert-butyl group, a docosanoyl group, a pivaloyloxymethyl group, an alanyl group, a hexylcarbamoyl group, a pentylcarbamoyl group, a 3-methylthio-1-(acetylamino)propylcarbonyl group, a 1-sulfo-1-(3-ethoxy-4-hydroxyphenyl)methyl group, a (5-methyl-2-oxo-1,3-dioxol-4-yl)methyl group, a (5-methyl-2-oxo-1,3-dioxol-4-yl)methoxycarbonyl group, a tetrahydrofuranyl group, a pyrrolidylmethyl group and the like.

Examples of the "pharmaceutical composition" include oral preparations such as tablet, capsule, granule, powder, troche, syrup, emulsion, suspension and the like, and parenteral agents such as external preparation, suppository, injection, eye drop, nasal preparation, pulmonary preparation and the like.

The pharmaceutical composition of the present invention is produced according to a method known in the art of pharmaceutical preparations, by mixing a compound represented by the formula [I] or a pharmaceutically acceptable salt thereof or a solvate thereof with a suitable amount of at least one kind of pharmaceutically acceptable carrier and the like as appropriate. While the content of the compound represented by the formula [I] or a pharmaceutically acceptable salt thereof, or a solvate thereof in the pharmaceutical composition varies depending on the dosage form, dose and the like, it is, for example, 0.1 to 100 wt % of the whole composition.

Examples of the "pharmaceutically acceptable carrier" include various organic or inorganic carrier substances conventionally used as preparation materials, for example, excipient, disintegrant, binder, glidant, lubricant and the like for solid preparations, and solvent, solubilizing agent, suspending agent, isotonicity agent, buffering agent, soothing agent and the like for liquid preparations. Where necessary, moreover, additives such as preservative, antioxidant, colorant, sweetening agent and the like are used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "glidant" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agents" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color Yellow No. 4 or 5 etc.), β-carotene and the like.

Examples of the "sweetening agent" include saccharin sodium, dipotassium glycyrrhizinate, aspartame and the like.

The compound of the present invention or a pharmaceutically acceptable salt thereof, or a solvate thereof has an EPO production-inducing activity due to a prolyl hydroxylase (PHD) inhibitory action, and can be used for the prophylaxis or treatment of various diseases and pathologies (disorders) caused by decreased production of EPO.

As the various diseases and pathologies (disorders) caused by decreased production of EPO, anemia and the like can be mentioned.

In general, anemia includes anemia due to hematopoiesis abnormality in the bone marrow, anemia due to shortage of iron, vitamin $B_{12}$ or folic acid, bleeding during accident or operation, anemia associated with chronic inflammation (autoimmune diseases, malignant tumor, chronically-transmitted diseases, plasma cell dyscrasia etc.), anemia associated with endocrine diseases (hypothyroidism, autoimmune polyglandular syndrome, type IA diabetes, dysfunctional uterine bleeding etc.), anemia associated with chronic cardiac failure, anemia associated with ulcer, anemia associated with hepatic diseases, senile anemia, drug-induced anemia, renal anemia (anemia associated with renal failure), anemia associated with chemical therapy, and the like.

Examples of the diseases expected to be improved by inhibiting PHD to stabilize HIF include ischemic cardiac diseases (angina pectoris, myocardial infarction etc.), ischemic cerebrovascular disorders (cerebral infarction, cerebral embolism, transient cerebral ischemic attack etc.), chronic renal failures (ischemic nephropathy, renal tubule interstitial disorder etc.), diabetic complications (diabetic wound etc.), cognitive impairments (dementia, Alzheimer's disease, Parkinson's disease, Huntington's disease etc.) and the like.

The prolyl hydroxylase (PHD) inhibitor and EPO production-inducing agent of the present invention is preferably used as a therapeutic agent for anemia, more preferably a therapeutic agent for renal anemia.

The pharmaceutical composition of the present invention can be administered orally or parenterally (e.g., topical, rectal, intravenous administration etc.) to human as well as mammals other than human (e.g., mouse, rat, hamster, guinea pig, rabbit, cat, dog, swine, bovine, horse, sheep, monkey etc.). The dose varies depending on the subject of administration, disease, symptom, dosage form, administration route and the like. For example, the daily dose for oral administration to an adult patient (body weight: about 60 kg) is generally within the range of about 1 mg to 1 g, based on the compound of the present invention as the active ingredient. This amount can be administered in one to several portions.

Since the compound of the present invention or a pharmaceutically acceptable salt thereof, or a solvate thereof inhibits PHD and induces production of EPO, it can be used as an active ingredient of a therapeutic agent or prophylactic agent for anemia.

To "inhibit PHD" means to specifically inhibit the function of prolyl hydroxylase and eliminate or attenuate the activity. For example, it means to specifically inhibit the function as prolyl hydroxylase based on the conditions in the below-mentioned Experimental Example 1. To "inhibit PHD" preferably means to inhibit human PHD. As a "PHD inhibitor", preferred is a "human PHD inhibitor".

To "induce production of EPO" means that the production of erythropoietin in the kidney etc. is promoted. For example, it means that the production of erythropoietin is induced based on the conditions of the below-mentioned Experimental Example 2. To "induce production of EPO" preferably means to "induce production of human EPO". An "EPO production-inducing agent" is preferably a "human EPO production-inducing agent".

The above-mentioned compound represented by the formula [I] or a pharmaceutically acceptable salt thereof, or a solvate thereof can be used in combination with one or a plurality of other medicaments (hereinafter to be also referred to as a concomitant drug) according to a method generally employed in the medical field (hereinafter to be referred to as combined use).

The administration period of the above-mentioned compound represented by the formula [I] or a pharmaceutically acceptable salt thereof, or a solvate thereof, and a concomitant drug is not limited, and they may be administered to an administration subject as combination preparation, or the both preparations may be administered simultaneously or at given intervals. In addition, the pharmaceutical composition of the present invention and a concomitant drug may be used as a medicament in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it only needs to be combined with the compound of the present invention or a pharmaceutically acceptable salt thereof, or a solvate thereof.

Examples of the concomitant drug include an agent for the treatment and/or prophylaxis of anemia and the like, and the compound of the present invention can be used in combination.

Examples of the "therapeutic agent and/or prophylaxis agent of anemia" include ferrous citrate, iron sulfate and the like.

As PHD, PHD2 and PHD3 can be mentioned.

Next, the production methods of the compound of the present invention or a pharmaceutically acceptable salt thereof, or a solvate thereof are specifically explained. However, it is needless to say that the present invention is not limited to such production methods. For production of the compound of the present invention or a pharmaceutically acceptable salt thereof, or a solvate thereof, the order of reactions can be appropriately changed. The reaction can be started from the step or substitution moiety that seems to be reasonable.

In addition, an appropriate substituent conversion (conversion or further modification of substituent) step may be inserted between respective steps. When a reactive functional group is present, protection and deprotection can be appropriately performed. To promote progress of the reaction, moreover, a reagent other than the exemplified reagent can be used as appropriate. Furthermore, a starting compound whose production method is not described is either commercially available or can be prepared easily by a combination of known synthetic reactions.

The compound obtained in each step can be purified by a conventional method such as distillation, recrystallization, column chromatography and the like. In some cases, the compound can be applied to the next step without isolation and purification.

In the following production method, the "room temperature" means 1-40° C.

Production Method I-1

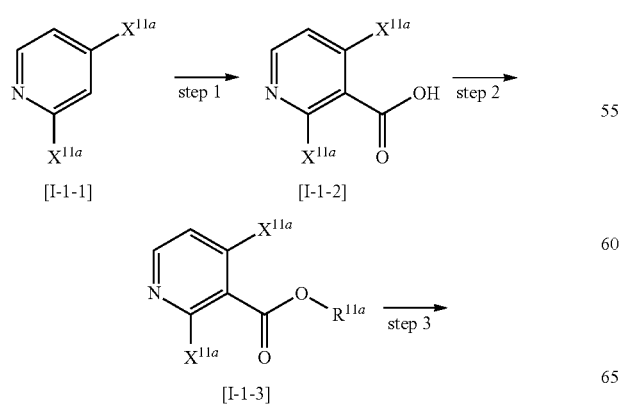

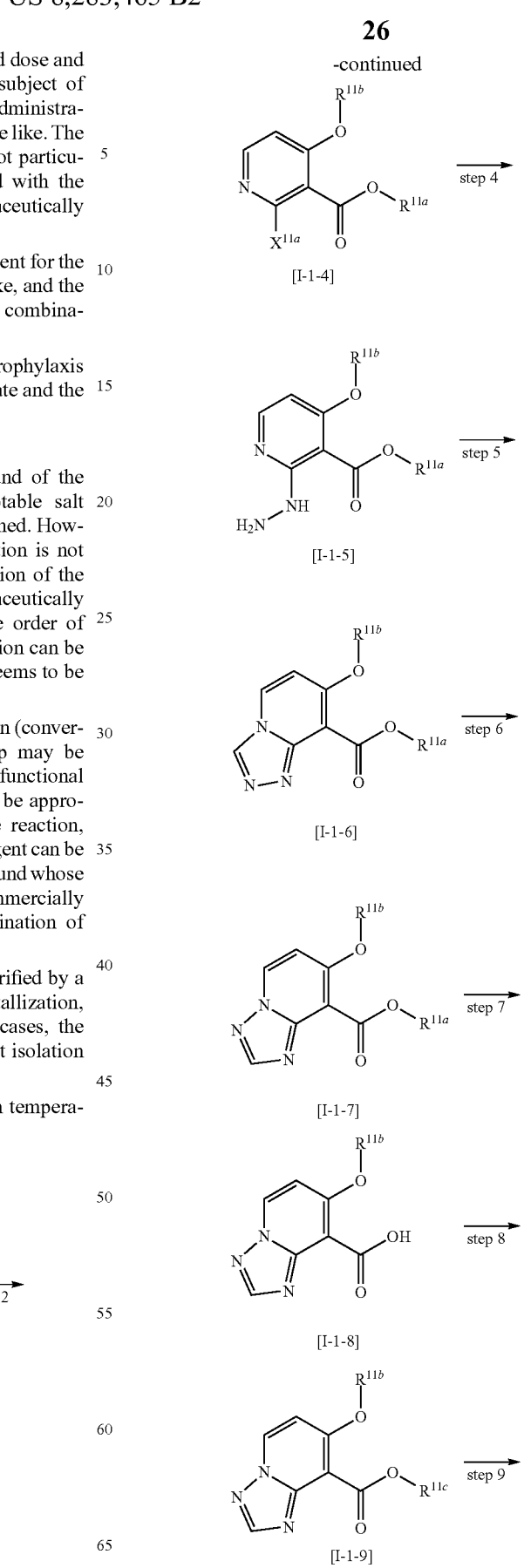

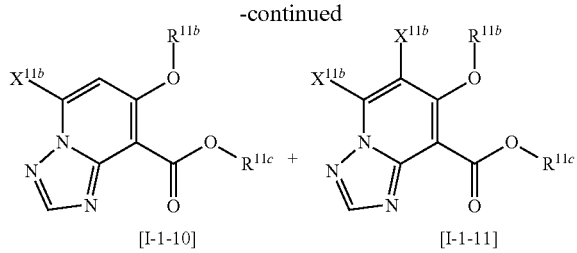

[I-1-10]       [I-1-11]

wherein $R^{11a}$ and $R^{11c}$ are each a carboxyl-protecting group such as a methyl group, an ethyl group, a benzyl group, a tert-butyl group and the like, $R^{11b}$ is a hydroxyl-protecting group such as an acetyl group, a benzyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $X^{11a}$ and $X^{11b}$ are each a halogen atom such as a chlorine atom, a bromine atom, an iodine atom, a fluorine atom and the like, a leaving group such as a p-toluenesulfonyloxy group, a methanesulfonyloxy group, a trifluoromethanesulfonyloxy group and the like.

Step 1

Compound [I-1-2] can be obtained by subjecting compound [I-1-1] to metalation according to a conventional method, and introducing a carboxyl group using carbon dioxide. Metalation is performed by reaction with an organic metal reagent such as n-butyllithium, sec-butyllithium, lithium diisopropylamide, lithium bis(trimethylsilyl)amide, sodium bis(trimethylsilyl)amide, potassium bis(trimethylsilyl)amide, lithium amide, sodium amide and the like under low temperature conditions in hexane, benzene, toluene, tetrahydrofuran, diethyl ether, 1,4-dioxane and the like alone or a mixed solvent thereof, which is followed by reaction with carbon dioxide to give compound [I-1-2].

Step 2

Compound [I-1-3] can be obtained by introducing a protecting group into the carboxyl group of compound [I-1-2] according to a conventional method. For example, when the protecting group is a tert-butyl group, compound [I-1-3] can be obtained by reaction with tert-butyl 2,2,2-trichloroacetimidate under low temperature to heating conditions in the presence of an acid such as p-toluenesulfonic acid, methanesulfonic acid, boron trifluoride, boron trichloride, boron tribromide, aluminum trichloride, hydrogen chloride, hydrogen bromide, phosphoric acid, sulfuric acid, acetic acid, trifluoroacetic acid and the like in hexane, chloroform, methylene chloride, ethyl acetate, toluene, 1,4-dioxane, tetrahydrofuran, 1,2-dimethoxyethane, dimethyl sulfoxide, N,N-dimethylformamide, acetonitrile and the like alone or a mixed solvent thereof.

Step 3

Compound [I-1-4] can be obtained by introducing a hydroxyl group protected by a protecting group represented by $R^{11b}$ into compound [I-1-3] according to a conventional method. For example, when a hydroxyl group protected by a benzyl group is introduced, compound [I-1-3] is reacted with benzyl alcohol under low temperature to heating conditions in the presence of a base such as triethylamine, potassium tert-butoxide, potassium carbonate, sodium hydride, n-butyllithium, lithium diisopropylamide and the like in hexane, dimethyl sulfoxide, N,N-dimethylformamide, acetonitrile, tetrahydrofuran, 1,4-dioxane, 1,2-dimethoxyethane, toluene and the like alone or a mixed solvent thereof, whereby compound [I-1-4] can be obtained.

Step 4

Compound [I-1-5] can be obtained by reacting compound [I-1-4] with hydrazine monohydrate under low temperature to heating conditions in chloroform, toluene, 1,4-dioxane, tetrahydrofuran, 1,2-dimethoxyethane, methanol, ethanol, 2-propanol, dimethyl sulfoxide, N,N-dimethylformamide, acetonitrile, water and the like alone or a mixed solvent thereof.

Step 5

Compound [I-1-6] can be obtained by reacting compound [I-1-5] with an orthoester compound such as trimethyl orthoformate, triethyl orthoformate and the like or formic acid under low temperature to heating conditions in the presence of an acid such as p-toluenesulfonic acid, methanesulfonic acid, boron trifluoride, boron trichloride, boron tribromide, hydrogen chloride, hydrogen bromide, phosphoric acid, sulfuric acid and the like in hexane, chloroform, methylene chloride, ethyl acetate, toluene, 1,4-dioxane, tetrahydrofuran, 1,2-dimethoxyethane, methanol, ethanol, 2-propanol, dimethyl sulfoxide, N,N-dimethylformamide, acetonitrile and the like alone or a mixed solvent or without solvent.

Step 6

Compound [I-1-7] can be obtained by performing an endocyclic rearrangement reaction of compound [I-1-6] at room temperature to under heating conditions in the presence of a base such as sodium hydroxide, morpholine, piperidine, pyrrolidine and the like in hexane, chloroform, methylene chloride, ethyl acetate, toluene, 1,2-dimethoxyethane, 1,4-dioxane, tetrahydrofuran, 1,2-dimethoxyethane, methanol, ethanol, 2-propanol, dimethyl sulfoxide, N,N-dimethylformamide, N,N-dimethylacetamide, acetonitrile and the like alone or a mixed solvent thereof.

Step 7

Compound [I-1-8] can be obtained by removing the carboxyl-protecting group of compound [I-1-7] according to a conventional method. For example, when $R^{11a}$ is a tert-butyl group, compound [I-1-8] can be obtained by reaction with an acid such as p-toluenesulfonic acid, methanesulfonic acid, boron trifluoride, boron trichloride, boron tribromide, aluminum trichloride, hydrogen chloride, hydrogen bromide, phosphoric acid, sulfuric acid, acetic acid, trifluoroacetic acid and the like under low temperature to heating conditions in hexane, chloroform, methylene chloride, ethyl acetate, toluene, 1,2-dimethoxyethane, 1,4-dioxane, tetrahydrofuran, methanol, ethanol, 2-propanol, dimethyl sulfoxide, N,N-dimethylformamide, N,N-dimethylacetamide, acetonitrile, water and the like alone or a mixed solvent thereof. When $R^{11a}$ is a methyl group, ethyl group or tert-butyl group, compound [I-1-8] can be obtained by hydrolyzing compound [I-1-7] under low temperature to heating conditions in the presence of a base such as sodium hydroxide, potassium hydroxide, potassium carbonate, sodium carbonate, lithium hydroxide and the like in a mixed solvent of water and a solvent such as methanol, ethanol, 2-propanol, tetrahydrofuran, 1,4-dioxane, 1,2-dimethoxyethane, N,N-dimethylformamide, acetonitrile and the like.

Step 8

Compound [I-1-9] can be obtained by introducing a protecting group into the carboxyl group of compound [I-1-8] according to a conventional method. For example, when the protecting group is an ethyl group, compound [I-1-9] can be obtained by reacting compound [I-1-8] with N,N-dimethylformamide diethyl acetal under low temperature to heating conditions in chloroform, methylene chloride, ethyl acetate, toluene, 1,4-dioxane, tetrahydrofuran, 1,2-dimethoxyethane, methanol, ethanol, 2-propanol, dimethyl sulfoxide, N,N-dimethylformamide, acetonitrile and the like alone or a mixed solvent thereof.

Step 7 and step 8 may be omitted. In this case, $R^{11a}=R^{11c}$.

Step 9

Compound [I-1-10] can be obtained by introducing a leaving group onto the pyridine ring of compound [I-1-9] according to a conventional method. Disubstituted compound [I-1-11] may be obtained. When the leaving group is an iodine atom, compound [I-1-10] and compound [I-1-11] can be obtained by reaction with an organic metal reagent such as n-butyllithium, sec-butyllithium, lithium diisopropylamide, lithium bis(trimethylsilyl)amide, sodium bis(trimethylsilyl)amide, potassium bis(trimethylsilyl)amide, lithium amide, sodium amide and the like under low temperature conditions in hexane, toluene, 1,2-dimethoxyethane, diethyl ether, 1,4-dioxane, tetrahydrofuran and the like alone or a mixed solvent thereof to perform metalation, followed by reaction with iodine.

Production Method I-2

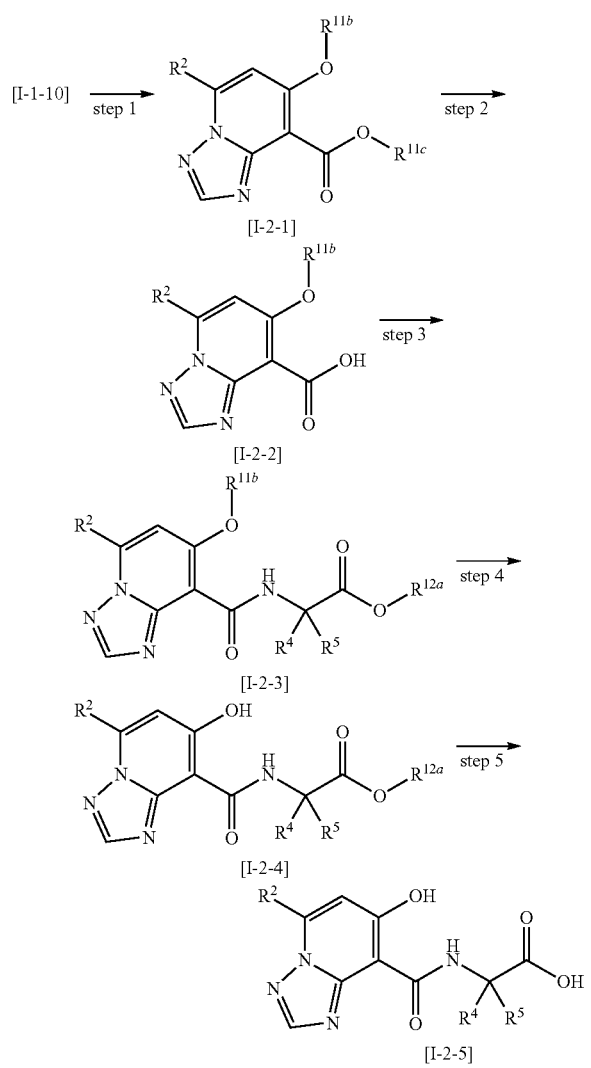

wherein $R^{12a}$ is a carboxyl-protecting group such as a methyl group, an ethyl group, a benzyl group, a tert-butyl group and the like, and other symbols are as defined above. Even when $R^2$ of [1-2-1] to [1-2-4] is other than the defined substituents, it can be used as long as the defined substituent can be finally obtained by appropriate substituent conversion.

Step 1

Compound [I-2-1] can be obtained by introducing substituent $R^2$ or a precursor thereof into compound [I-1-10] according to a conventional method. For example, when $R^2$ is a butyl group, compound [I-2-1] can be obtained by reacting compound [I-1-10] with butylboronic acid at room temperature to under heating conditions in the presence of a palladium catalyst such as [1,1-bis(diphenylphosphino)ferrocene]palladium(II) dichloride, tetrakis(triphenylphosphine)palladium, bis(triphenylphosphine)palladium(II) dichloride, palladium acetate-triphenylphosphine and the like and a base such as potassium acetate, potassium carbonate, potassium hydrogen carbonate, sodium hydrogen carbonate, potassium phosphate, triethylamine, diisopropylethylamine, sodium hydrogenphosphate, cesium carbonate and the like, by adding a silver salt as necessary such as silver carbonate, silver nitrate, silver(I) oxide and the like in hexane, N,N-dimethylformamide, N,N-dimethylacetamide, acetonitrile, 1,2-dimethoxyethane, tetrahydrofuran, 1,4-dioxane, toluene, water and the like alone or a mixed solvent thereof.

Step 2

Compound [I-2-2] can be obtained by removing the carboxyl-protecting group of compound [I-2-1] in the same manner as in production method I-1, step 7.

Step 3

Compound [I-2-3] can be obtained by condensing compound [I-2-2] with a glycine derivative represented by $H_2NC(R^4)(R^5)COOR^{12a}$ according to a conventional method. For example, compound [I-2-3] can be obtained by condensing compound [I-2-2] with a glycine derivative represented by $H_2NC(R^4)(R^5)COOR^{12a}$ under low temperature to heating conditions in the presence of a condensing agent such as dicyclohexylcarbodiimide, 1,1'-carbonyldiimidazole, 1-ethyl-3-(3-dimethylaminopropyl)carbodiimide or a salt thereof, diphenylphosphoryl azide and the like and, as necessary, N-hydroxysuccinimide, 1-hydroxybenzotriazole, dimethylaminopyridine and the like and, as necessary, adding a base such as potassium carbonate, sodium hydrogen carbonate, cesium carbonate, triethylamine, diisopropylethylamine, morpholine, pyridine and the like in a solvent such as N,N-dimethylformamide, acetonitrile, tetrahydrofuran, chloroform, ethyl acetate, methylene chloride, toluene and the like.

Step 4

Compound [I-2-4] can be obtained by removing hydroxyl-protecting group $R^{11b}$ of compound [I-2-3] according to a conventional method. For example, when $R^{11b}$ is a benzyl group, compound [I-2-4] can be obtained by hydrogenation under room temperature to heating conditions under a hydrogen atmosphere at normal pressure to under pressurization conditions in the presence of a catalyst such as palladium carbon, palladium hydroxide, platinum oxide, platinum carbon, Raney-nickel and the like in hexane, methanol, ethanol, 2-propanol, tetrahydrofuran, N,N-dimethylformamide, N,N-dimethylacetamide, ethyl acetate, acetic acid, water and the like alone or a mixed solvent thereof.

Step 5

Compound [I-2-5] can be obtained in the same manner as in production method I-1, step 7, by removing the carboxyl-protecting group of compound [I-2-4].

Production Method I-3

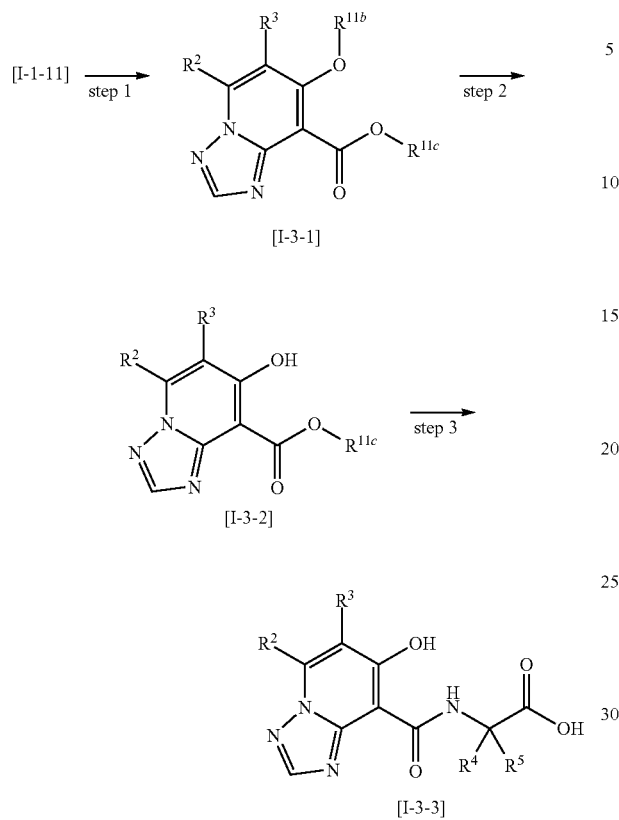

Production Method I-4

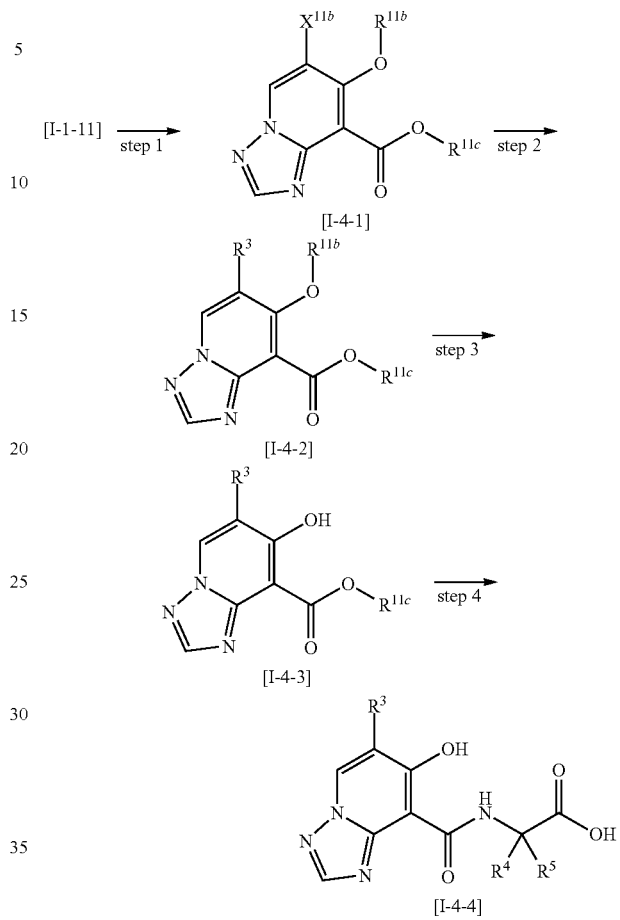

wherein even when $R^2$ and $R^3$ of [I-3-1] and [I-3-2] are other than the defined substituents, they can be used as long as the defined substituents can be finally obtained by appropriate substituent conversion, and other symbols are as defined above.

Step 1

Compound [I-3-1] can be obtained by introducing substituents $R^2$ and $R^3$ or a precursor thereof into compound [I-1-11] in the same manner as in production method I-2, step 1. For example, when an alkenyl group is introduced as a precursor of $R^2$ and $R^3$, compound [I-3-1] can be obtained by reacting compound [I-1-11] with alkenylboronic acid in the same manner as in production method I-2, step 1.

Step 2

Compound [I-3-2] can be obtained by deprotection of $R^{11b}$ of compound [I-3-1] in the same manner as in production method I-2, step 4.

Step 3

Compound [I-3-3] can be obtained by reacting compound [I-3-2] with a glycine derivative represented by $H_2NC(R^4)(R^5)COOH$. For example, compound [I-3-3] can be obtained by reacting compound [I-3-2] with a sodium salt of glycine derivative at room temperature to under heating conditions in hexane, chloroform, methylene chloride, toluene, 1,4-dioxane, tetrahydrofuran, 1,2-dimethoxyethane, methanol, ethanol, 2-propanol, 2-methoxyethanol, dimethyl sulfoxide, N,N-dimethylformamide, acetonitrile, water and the like alone or a mixed solvent thereof.

wherein even when $R^3$ of [I-4-2] and [I-4-3] is other than the defined substituents, it can be used as long as the defined substituents can be finally obtained by appropriate substituent conversion, and other symbols are as defined above.

Step 1

Compound [I-4-1] can be obtained by stirring compound [I-1-11] under low temperature to heating conditions in the presence of a palladium catalyst such as [1,1-bis(diphenylphosphino)ferrocene]palladium(II) dichloride, tetrakis(triphenylphosphine)palladium, bis(triphenylphosphine)palladium(II) dichloride, palladium acetate-triphenylphosphine and the like and a reducing agent such as tri-n-butyltin hydride and the like in hexane, chloroform, methylene chloride, ethyl acetate, benzene, toluene, 1,2-dimethoxyethane, 1,4-dioxane, tetrahydrofuran, diethyl ether, acetonitrile, water and the like alone or a mixed solvent thereof.

Step 2

Compound [I-4-2] can be obtained by substitution of $X^{11b}$ of compound [I-4-1] by $R^3$ or a precursor thereof in the same manner as in production method I-2, step 1.

Step 3

Compound [I-4-3] can be obtained by deprotection of $R^{11b}$ of compound [I-4-2] in the same manner as in production method I-2, step 4.

Step 4

Compound [I-4-4] can be obtained by reacting compound [I-4-3] with a glycine derivative represented by $H_2NC(R^4)$ ($R^5$)COOH or a salt with a metal species thereof in the same manner as in production method I-3, step 3.

Production Method I-5

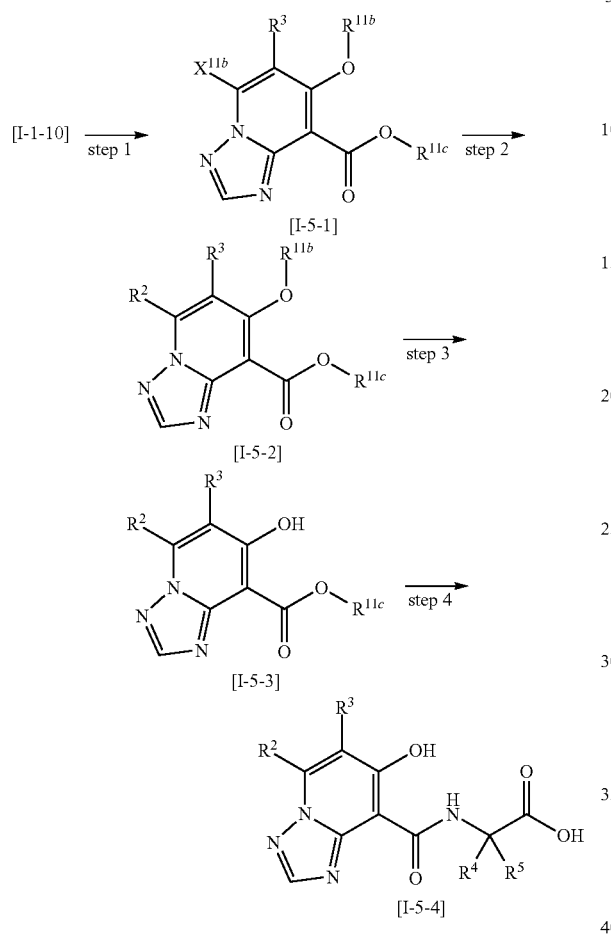

wherein each symbol is as defined above.

Step 1

Compound [I-5-1] can be obtained by introducing substituent $R^3$ into compound [I-1-10] according to a conventional method. For example, when $R^3$ is a chloro group, compound [I-5-1] can be obtained by reacting compound [I-1-10] with a chlorinating agent such as hexachloroethane and the like under low temperature conditions in the presence of an organic metal reagent such as n-butyllithium, lithium hexamethyl disilazide, sodium bis(trimethylsilyl)amide, potassium hexamethyl disilazide, lithium diisopropylamide, tert-butoxide and the like in hexane, benzene, toluene, tetrahydrofuran, diethyl ether, 1,4-dioxane and the like alone or a mixed solvent thereof.

Step 2

Compound [I-5-2] can be obtained by substituting substituent $X^{11b}$ of compound [I-5-1] by substituent $R^2$ or a precursor thereof in the same manner as in production method I-2, step 1.

Step 3

Compound [I-5-3] can be obtained by deprotection of $R^{11b}$ of compound [I-5-2] in the same manner as in production method I-2, step 4.

Step 4

Compound [I-5-4] can be obtained by reacting compound [I-5-3] with a glycine derivative represented by $H_2NC(R^4)$ ($R^5$)COOH or a salt with a metal species thereof in the same manner as in production method I-3, step 3.

Production Method I-6

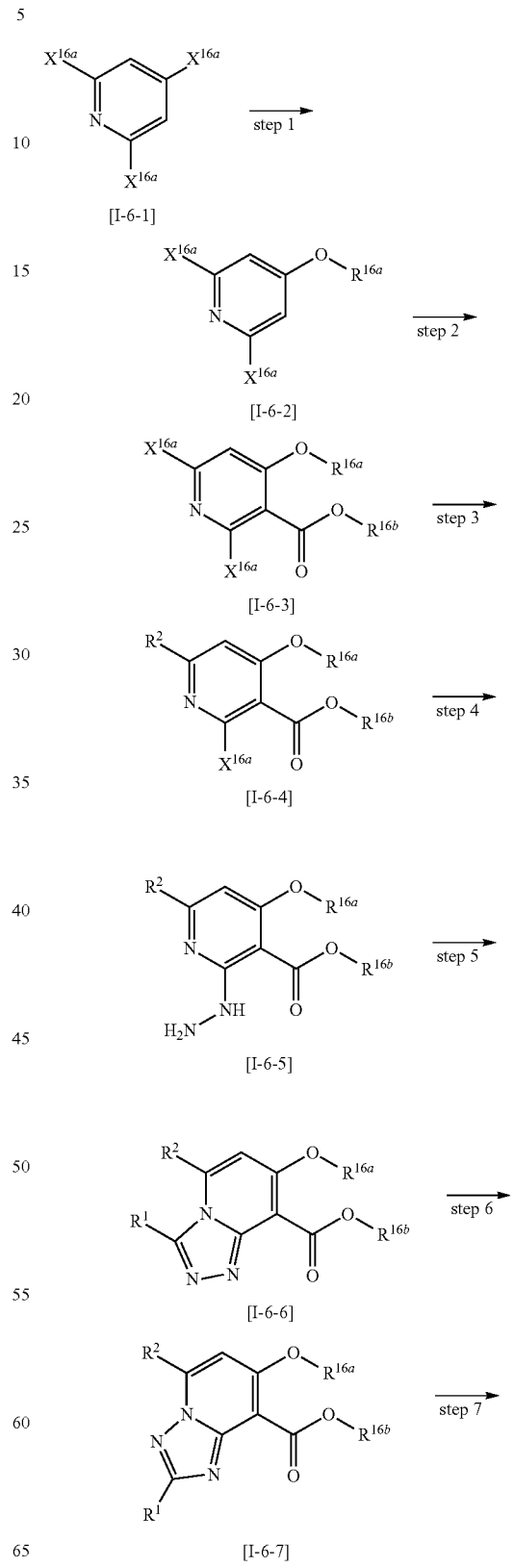

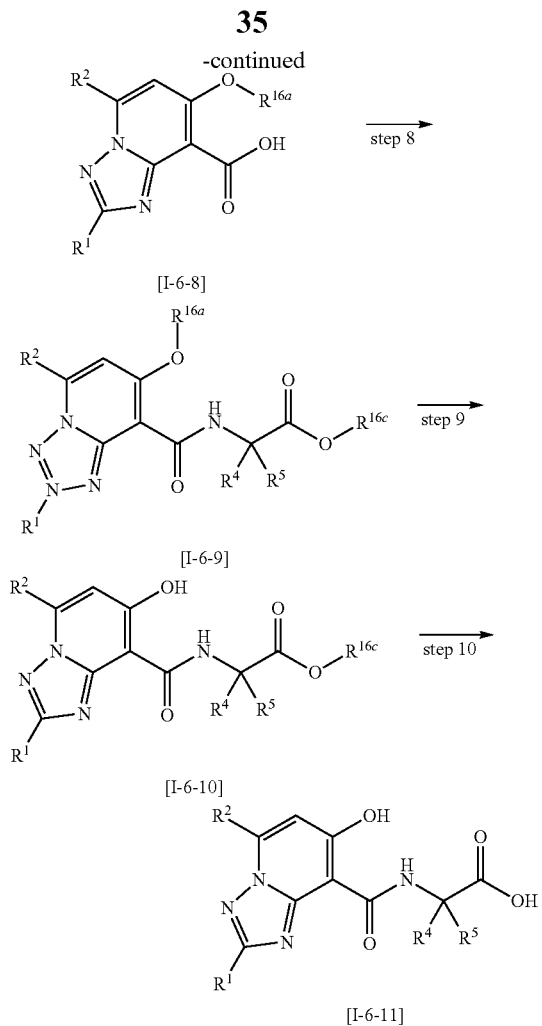

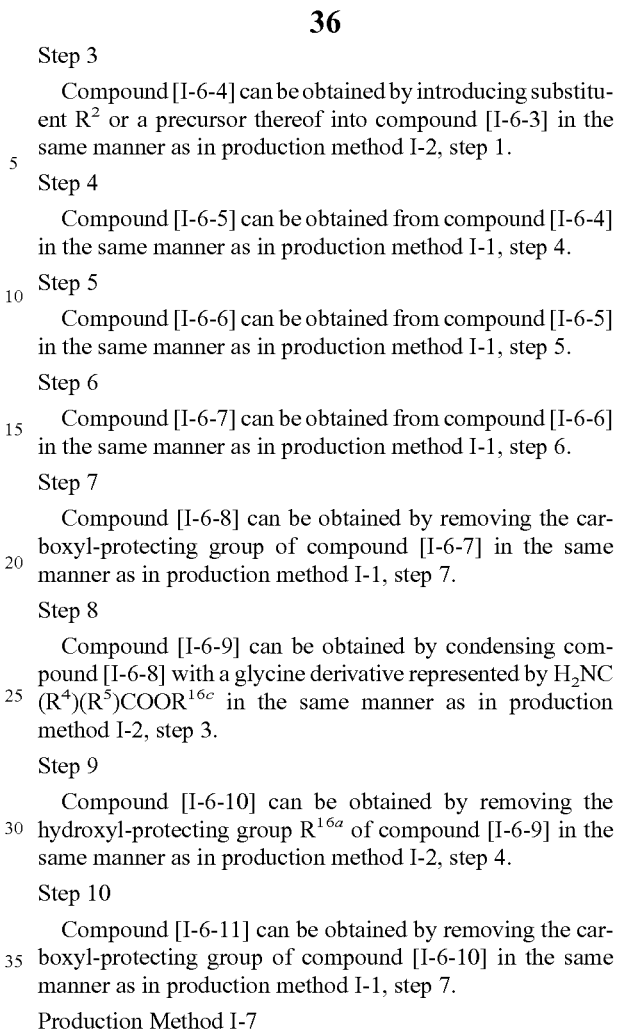

Step 3

Compound [I-6-4] can be obtained by introducing substituent $R^2$ or a precursor thereof into compound [I-6-3] in the same manner as in production method I-2, step 1.

Step 4

Compound [I-6-5] can be obtained from compound [I-6-4] in the same manner as in production method I-1, step 4.

Step 5

Compound [I-6-6] can be obtained from compound [I-6-5] in the same manner as in production method I-1, step 5.

Step 6

Compound [I-6-7] can be obtained from compound [I-6-6] in the same manner as in production method I-1, step 6.

Step 7

Compound [I-6-8] can be obtained by removing the carboxyl-protecting group of compound [I-6-7] in the same manner as in production method I-1, step 7.

Step 8

Compound [I-6-9] can be obtained by condensing compound [I-6-8] with a glycine derivative represented by $H_2NC(R^4)(R^5)COOR^{16c}$ in the same manner as in production method I-2, step 3.

Step 9

Compound [I-6-10] can be obtained by removing the hydroxyl-protecting group $R^{16a}$ of compound [I-6-9] in the same manner as in production method I-2, step 4.

Step 10

Compound [I-6-11] can be obtained by removing the carboxyl-protecting group of compound [I-6-10] in the same manner as in production method I-1, step 7.

Production Method I-7

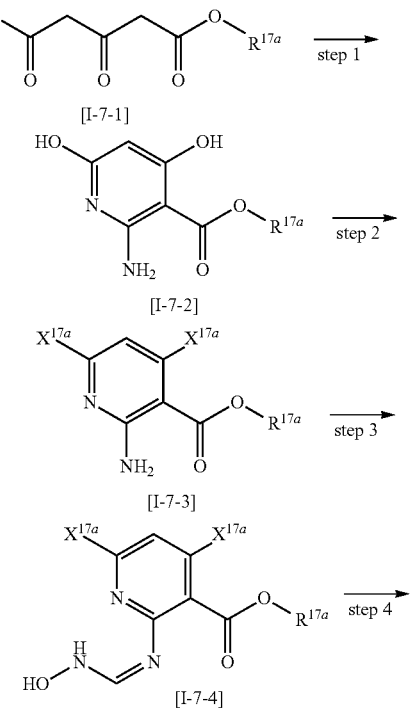

wherein $R^{16a}$ is a hydroxyl-protecting group such as an acetyl group, a benzyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $R^{16b}$ and $R^{16c}$ are each a carboxyl-protecting group such as a methyl group, an ethyl group, a benzyl group, a tert-butyl group and the like, $X^{16a}$ is a halogen atom such as a fluorine atom, a chlorine atom, a bromine atom, an iodine atom and the like, or a leaving group such as a p-toluenesulfonyloxy group, a methanesulfonyloxy group, a trifluoromethanesulfonyloxy group and the like, and other symbols are as defined above. Even when $R^2$ of [I-6-4] to [I-6-10] are other than the defined substituents, they can be used as long as the defined substituents can be finally obtained by appropriate substituent conversion.

Step 1

Compound [I-6-2] can be obtained by introducing a hydroxyl group protected by a protecting group $R^{16a}$ into compound [I-6-1] in the same manner as in production method I-1, step 3.

Step 2

Compound [I-6-3] can be obtained by introducing a carboxyl group protected by a protecting group $R^{16b}$ into compound [I-6-2] in the same manner as in production method I-1, step 1.

-continued

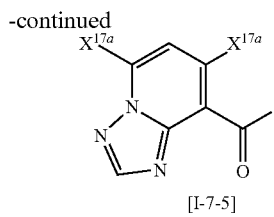

[I-7-5]

wherein $R^{17a}$ is a carboxyl-protecting group such as a methyl group, an ethyl group, a benzyl group, a tert-butyl group and the like, $X^{17a}$ is a halogen atom such as a fluorine atom, a chlorine atom, a bromine atom, an iodine atom and the like, or a leaving group such as a p-toluenesulfonyloxy group, a methanesulfonyloxy group, a trifluoromethanesulfonyloxy group and the like.

Step 1

Compound [I-7-2] can be obtained by reacting compound [I-7-1] with cyanamide in the presence of an organic metal reagent such as nickel(II) acetylacetonate and the like under low temperature to heating conditions in hexane, ethyl acetate, chloroform, methylene chloride, toluene, 1,4-dioxane, tetrahydrofuran, 1,2-dimethoxyethane, methanol, ethanol, 2-propanol, dimethyl sulfoxide, N,N-dimethylformamide, N-methyl-2-pyrrolidone, acetonitrile, water and the like alone or a mixed solvent thereof.

Step 2

Compound [I-7-3] can be obtained by converting the hydroxyl group of compound [I-7-2] to a leaving group according to a conventional method. For example, when the leaving group $X^{17a}$ is a chlorine atom, compound [I-7-3] can be obtained by chlorinating compound [I-7-2] with thionyl chloride, oxalyl chloride, triphosgene, phosphorus pentachloride, phosphorus oxychloride and the like under low temperature to heating conditions in hexane, ethyl acetate, acetone, chloroform, methylene chloride, toluene, 1,4-dioxane, tetrahydrofuran, 1,2-dimethoxyethane, methanol, ethanol, 2-propanol, dimethyl sulfoxide, N,N-dimethylformamide, 2-pyrrolidone, acetonitrile and the like alone or a mixed solvent thereof or without solvent in the presence of, where necessary, a base such as triethylamine, pyridine, 4-(dimethylamino)pyridine, N-methylmorpholine, diisopropylethylamine, tetramethylethylenediamine and the like and, where necessary, N,N-dimethylformamide.

Step 3

Compound [I-7-4] can be obtained by reacting compound [I-7-3] with N,N-dimethylformamide dialkyl acetal under low temperature to heating conditions in ethyl acetate, chloroform, toluene, 1,4-dioxane, tetrahydrofuran, 1,2-dimethoxyethane, methanol, ethanol, 2-propanol, dimethyl sulfoxide, N,N-dimethylformamide, acetonitrile and the like alone or a mixed solvent thereof, and then with hydroxylamine or a hydrochloride thereof.

Step 4

Compound [I-7-5] can be obtained by subjecting compound [I-7-4] to a dehydrating reaction using polyphosphoric acid, thionyl chloride, phosphorus oxychloride, p-toluenesulfonyl chloride, acetic anhydride, acetyl chloride, trifluoroacetic anhydride and the like under low temperature to high temperature conditions in hexane, ethyl acetate, acetone, chloroform, toluene, 1,4-dioxane, tetrahydrofuran, 1,2-dimethoxyethane, dimethyl sulfoxide, N,N-dimethylformamide, acetonitrile and the like alone or a mixed solvent thereof.

Production Method I-8

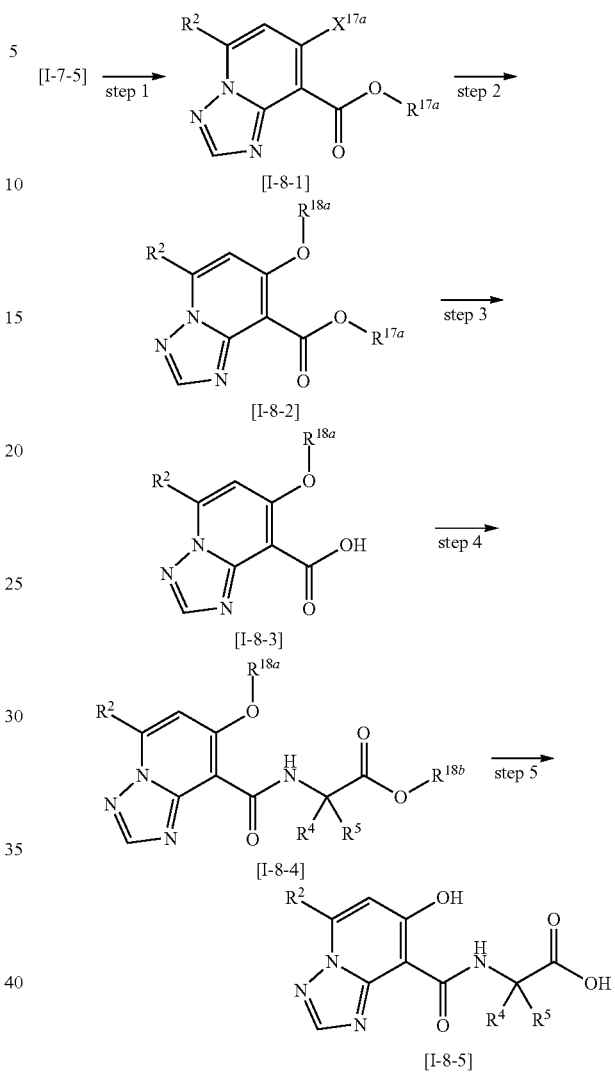

wherein $R^{18a}$ is a hydroxyl-protecting group such as an acetyl group, a benzyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $R^{18b}$ is a carboxyl-protecting group such as methyl group, an ethyl group, a benzyl group, a tert-butyl group and the like, and other symbols are as defined above.

Step 1

Compound [I-8-1] can be obtained by introducing substituent $R^2$ or a precursor thereof into compound [I-7-5] according to a conventional method in the same manner as in production method I-2, step 1.

Step 2

Compound [I-8-2] can be obtained by introducing a hydroxyl group protected by a protecting group represented by $R^{18a}$ into compound [I-8-1]. For example, when a hydroxyl group protected by a methyl group is introduced, compound [I-8-2] can be obtained by reacting compound [I-8-1] with sodium methoxide under low temperature to heating conditions in hexane, dimethyl sulfoxide, N,N-dimethylformamide, acetonitrile, tetrahydrofuran, 1,4-dioxane, 1,2-dimethoxyethane, toluene, methanol, water and the like alone or a mixed solvent thereof, or with a base such as triethylamine, potassium tert-butoxide, sodium methoxide, potassium carbonate, sodium hydride, n-butyllithium, lithium diisopropylamide and the like under low temperature to heating conditions in methanol alone or a mixed solvent with hexane, dimethyl sulfoxide, N,N-dimethylformamide, acetonitrile, tetrahydrofuran, 1,4-dioxane, 1,2-dimethoxyethane, toluene and the like.

Step 3

Compound [I-8-3] can be obtained by removing the carboxyl-protecting group of compound [I-8-2] in the same manner as in production method I-1, step 7.

Step 4

Compound [I-8-4] can be obtained by condensing compound [I-8-3] with a glycine derivative represented by H$_2$NC(R$^4$)(R$^5$) COOR$^{18b}$ in the same manner as in production method I-2, step 3.

Step 5

Compound [I-8-5] can be obtained by removing the hydroxyl-protecting group R$^{18a}$ and the carboxyl-protecting group R$^{18b}$ of compound [I-8-4] according to a conventional method. For example, when R$^{18a}$ is a methyl group and R$^{18b}$ is a tert-butyl group, compound [I-8-5] can be obtained by stirring compound [I-8-4] at room temperature to under heating conditions in the presence of an acid such as p-toluenesulfonic acid, methanesulfonic acid, boron trifluoride, boron trifluoride-diethyl ether complex, boron trichloride, boron tribromide, hydrogen chloride, hydrogen bromide, phosphoric acid, sulfuric acid, acetic acid, trifluoroacetic acid and the like in hexane, ethyl acetate, acetone, chloroform, methylene chloride, ethyl acetate, toluene, 1,2-dimethoxyethane, 1,4-dioxane, tetrahydrofuran, 1,2-dimethoxyethane, methanol, ethanol, isopropanol, dimethyl sulfoxide, N,N-dimethylformamide, N,N-dimethylacetamide, acetonitrile, acetic acid, water and the like alone or a mixed solvent thereof.

Production Method I-9

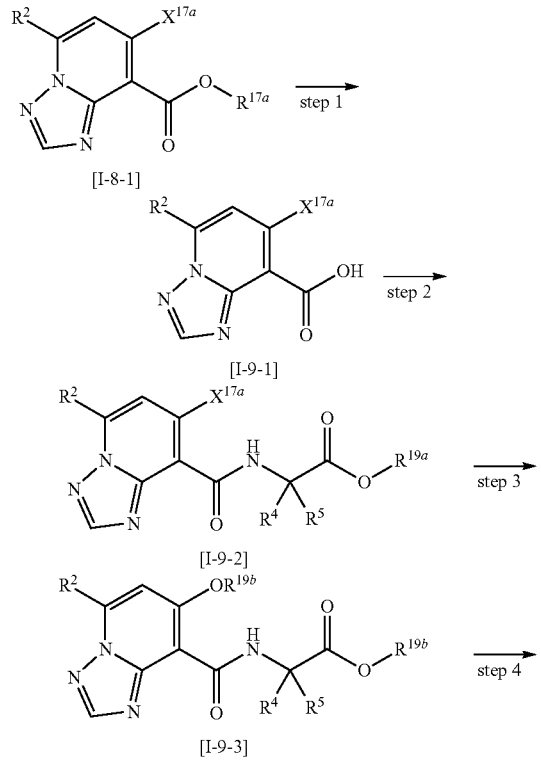

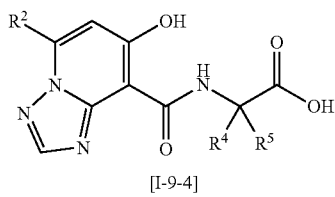

wherein R$^{19a}$ is a carboxyl-protecting group such as a methyl group, an ethyl group, a benzyl group, a tert-butyl group and the like, R$^{19b}$ is a metal species forming a salt with carboxylic acid or phenol, such as lithium, sodium, calcium etc., and other symbols are as defined above.

Step 1

Compound [I-9-1] can be obtained by removing the carboxyl-protecting group of compound [I-8-1] in the same manner as in production method I-1, step 7.

Step 2

Compound [I-9-2] can be obtained by condensing compound [I-9-1] with a glycine derivative represented by H$_2$NC(R$^4$)(R$^5$)COOR$^{19a}$ in the same manner as in production method I-2, step 3.

Step 3

Compound [I-9-3] can be obtained by reacting compound [I-9-2] with a base. For example, when R$^{19b}$ is sodium, compound [I-9-3] can be obtained by reacting compound [I-9-2] with sodium hydroxide at room temperature to under heating conditions in dimethyl sulfoxide, N,N-dimethylformamide, dimethylacetamide, acetonitrile, tetrahydrofuran, 1,4-dioxane, 1,2-dimethoxyethane, toluene, methanol, ethanol, 2-methoxyethanol, 2-ethoxyethanol, water and the like alone or a mixed solvent thereof.

Step 4

Compound [I-9-4] can be obtained by reacting compound [I-9-3] with an acid such as acetic acid, p-toluenesulfonic acid, methanesulfonic acid, trifluoroacetic acid, hydrogen chloride, hydrogen bromide, phosphoric acid, sulfuric acid and the like under low temperature to heating conditions in dimethyl sulfoxide, N,N-dimethylformamide, acetone, acetonitrile, tetrahydrofuran, 1,4-dioxane, 1,2-dimethoxyethane, toluene, methanol, ethanol, 2-methoxyethanol, 2-ethoxyethanol, water and the like alone or a mixed solvent thereof.

Production Method II-1

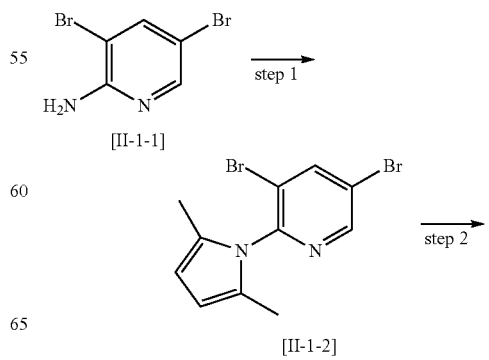

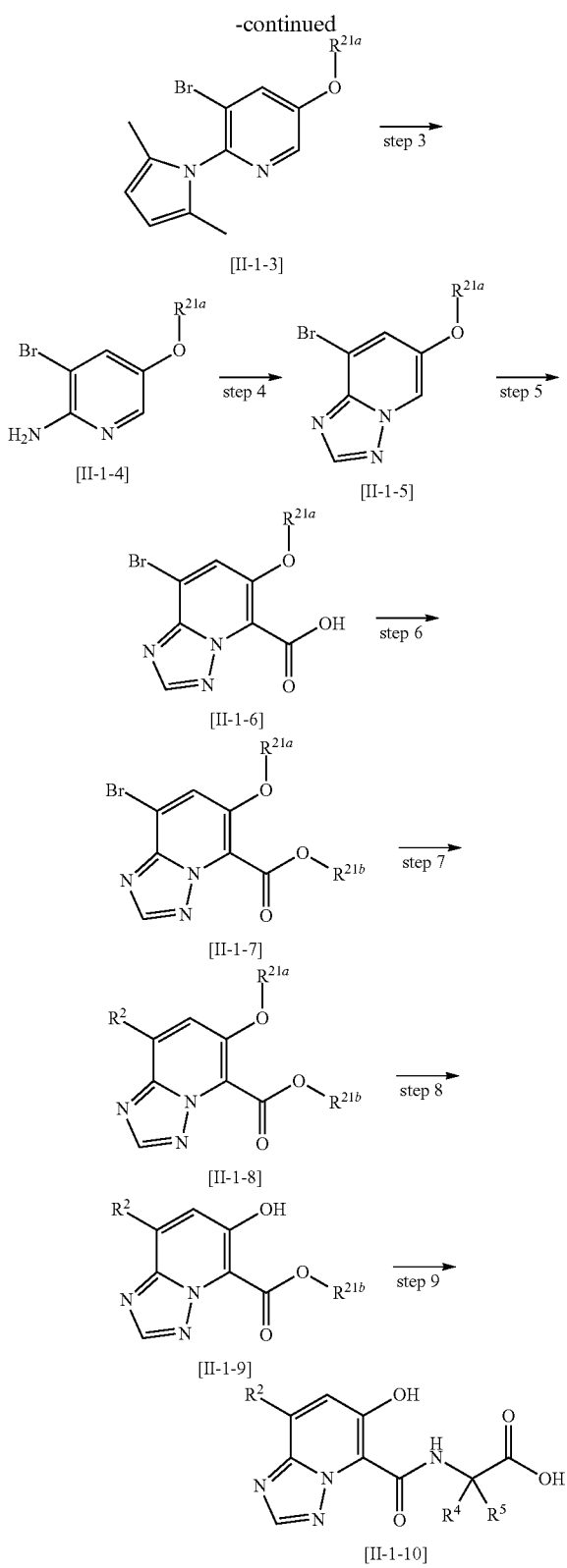

wherein $R^{21a}$ is a hydroxyl-protecting group such as a benzyl group, an acetyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $R^{21b}$ is a carboxyl-protecting group such as methyl group, an ethyl group, a benzyl group, a tert-butyl group and the like, and other symbols are as defined above. Even when $R^2$ of [II-1-8] to [II-1-9] are other than the defined substituents, they can be used as long as the defined substituents can be finally obtained by appropriate substituent conversion.

Step 1

Compound [II-1-2] can be, obtained by reacting compound [II-1-1] with 2,5-hexanedione under low temperature to heating conditions in the presence of an acid such as p-toluenesulfonic acid, methanesulfonic acid, boron trifluoride, boron trichloride, boron tribromide, aluminum trichloride, hydrogen chloride, hydrogen bromide, phosphoric acid, sulfuric acid, sulfamic acid, acetic acid, trifluoroacetic acid and the like in hexane, chloroform, methylene chloride, ethyl acetate, methanol, ethanol, 2-propanol, toluene, 1,4-dioxane, tetrahydrofuran, 1,2-dimethoxyethane, dimethyl sulfoxide, N,N-dimethylformamide, acetonitrile, water and the like alone or a mixed solvent thereof.

Step 2

Compound [II-1-3] can be obtained by introducing a hydroxyl group protected by a protecting group represented by $R^{21a}$ into compound [II-1-2] in the same manner as in production method I-1, step 3.

Step 3

Compound [II-1-4] can be obtained by stirring compound [II-1-3] under low temperature to heating conditions in the presence of a base such as triethylamine, potassium tert-butoxide, potassium carbonate, sodium hydride, lithium diisopropylamide and the like and hydroxylammonium chloride in methanol, ethanol, 2-propanol, dimethyl sulfoxide, N,N-dimethylformamide, acetonitrile, water and the like alone or a mixed solvent thereof.

Step 4

Compound [II-1-4] is reacted with N,N-dimethylformamide dimethyl acetal at room temperature to under heating conditions in ethyl acetate, chloroform, toluene, 1,4-dioxane, tetrahydrofuran, 1,2-dimethoxyethane, methanol, ethanol, 2-propanol, dimethyl sulfoxide, N,N-dimethylformamide, acetonitrile and the like alone or a mixed solvent thereof to give a compound, which is reacted with hydroxylamine or a salt thereof in the presence of a base such as triethylamine, diisopropylethylamine, morpholine, pyridine and the like under low temperature to high temperature conditions in hexane, ethyl acetate, acetone, chloroform, toluene, 1,4-dioxane, tetrahydrofuran, 1,2-dimethoxyethane, methanol, ethanol, 2-propanol, dimethyl sulfoxide, N,N-dimethylformamide, acetonitrile and the like alone or a mixed solvent thereof, and reacted with polyphosphoric acid or hydroxylamine-O-sulfonic acid, whereby compound [II-1-5] can be obtained.

Step 5

Compound [II-1-6] can be obtained by introducing a carboxyl group into compound [II-1-5] in the same manner as in production method I-1, step 1.

Step 6

Compound [II-1-7] can be obtained by introducing a protecting group $R^{21b}$ into the carboxyl group of compound [II-1-6] according to a conventional method. For example, when $R^{21b}$ is an ethyl group, compound [II-1-7] can be obtained by reacting compound [II-1-6] with N,N-dimethylformamide diethyl acetal at room temperature to under heating conditions in hexane, chloroform, methylene chloride, ethyl acetate, toluene, 1,4-dioxane, tetrahydrofuran, 1,2-dimethoxyethane, dimethyl sulfoxide, N,N-dimethylformamide, acetonitrile and the like alone or a mixed solvent thereof.

Step 7

Compound [II-1-8] can be obtained by introducing a substituent $R^2$ or a precursor thereof into compound [II-1-7] according to a conventional method. For example, when a tert-butylacetylene group is introduced, compound [II-1-8] can be obtained by reacting compound [II-1-7] with tert-butylacetylene at room temperature to under heating conditions in the presence of a palladium catalyst such as [1,1-bis(diphenylphosphino)ferrocene]palladium(II) dichloride, tetrakis(triphenylphosphine)palladium, bis(triphenylphosphine)palladium(II) dichloride, palladium acetate-triphenylphosphine and the like, a base such as potassium acetate, potassium carbonate, potassium hydrogen carbonate, sodium hydrogen carbonate, potassium phosphate, triethylamine, diisopropylethylamine, sodium hydrogenphosphate, cesium carbonate and the like and copper iodide in hexane, N,N-dimethylformamide, N,N-dimethylacetamide, acetonitrile, 1,2-dimethoxyethane, tetrahydrofuran, 1,4-dioxane, toluene, water and the like alone or a mixed solvent thereof.

Step 8

Compound [II-1-9] can be obtained by deprotection of the hydroxyl-protecting group $R^{21a}$ of compound [II-1-8] in the same manner as in production method I-2, step 4.

Step 9

Compound [II-1-10] can be obtained from compound [II-1-9] in the same manner as in production method I-3, step 3.

In this production method, a production method when $R^1$ is a hydrogen atom has been described. When $R^1$ is the aforementioned substituent and other than a hydrogen atom, N,N-dimethylformamide dimethyl acetal substituted by a desired substituent may be used instead of N,N-dimethylformamide dimethyl acetal in step 4, and step 5 and the following can be performed by a method similar to the method described in this production method.

Production Method III-1

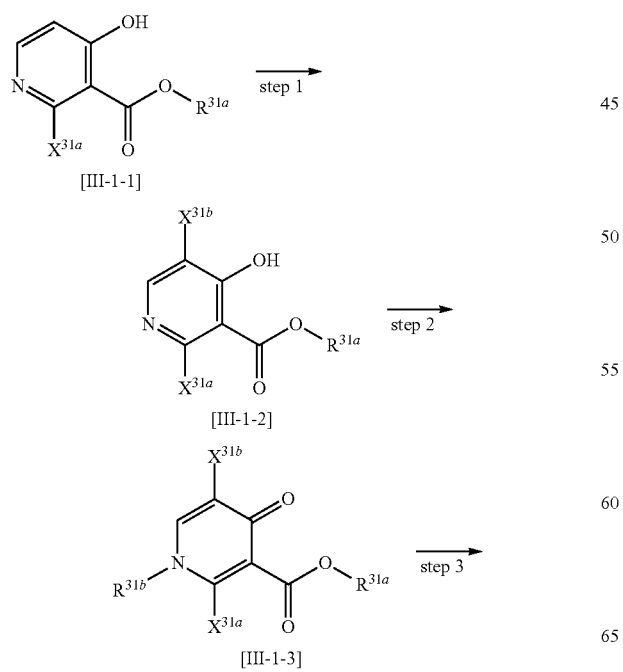

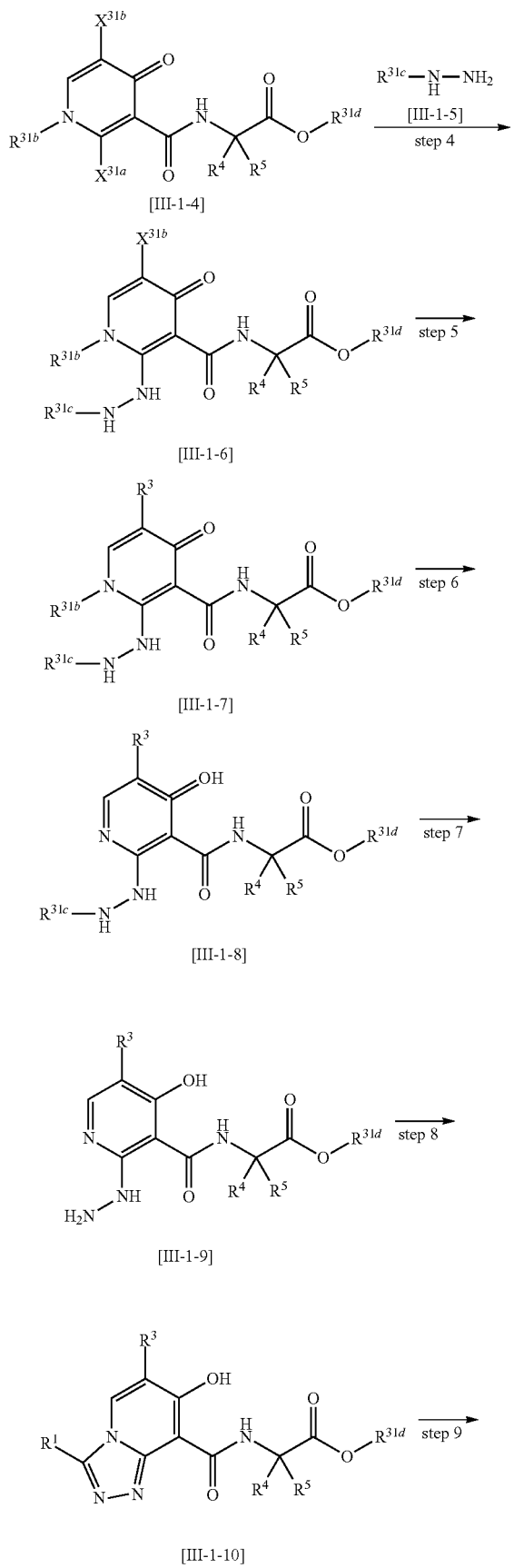

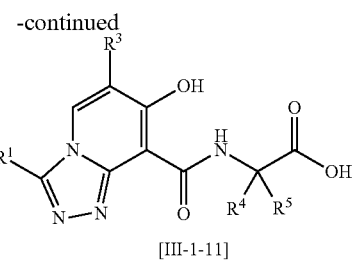

[III-1-11]

wherein $R^{31a}$ and $R^{31d}$ are each a carboxyl-protecting group such as a methyl group, an ethyl group, a benzyl group, a tert-butyl group and the like, $R^{31b}$ and $R^{31c}$ are each an amino-protecting group such as a benzyloxycarbonyl group, a tert-butoxycarbonyl group, a benzyl group and the like, $X^{31a}$ and $X^{31b}$ are each a halogen atom such as a fluorine atom, a chlorine atom, a bromine atom, an iodine atom and the like, a leaving group such as a p-toluenesulfonyloxy group, a methanesulfonyloxy group, a trifluoromethanesulfonyloxy group and the like, and other symbols are as described above.

Step 1

Compound [III-1-2] can be obtained by introducing a leaving group $X^{31b}$ according to a conventional method into compound [III-1-1] obtained by deprotecting $R^{11b}$ of compound [I-1-4] in the same manner as in production method I-2, step 4. For example, when $X^{31b}$ is a bromine atom, compound [III-1-2] can be obtained by reacting compound [III-1-1] with bromine or N-bromosuccinimide under low temperature to heating conditions in hexane, chloroform, methylene chloride, ethyl acetate, toluene, tetrahydrofuran, 1,4-dioxane, acetonitrile, water and the like alone or a mixed solvent thereof.

Step 2

Compound [III-1-3] can be obtained by introducing $R^{31b}$ into compound [III-1-2] according to a conventional method. For example, when $R^{31b}$ is a benzyl group, compound [III-1-3] can be obtained by reacting compound [III-1-2] with benzyl chloride or benzyl bromide in the presence of a base such as potassium carbonate, potassium tert-butoxide, sodium hydride, cesium carbonate and the like in ethyl acetate, chloroform, toluene, 1,4-dioxane, tetrahydrofuran, 1,2-dimethoxyethane, dimethyl sulfoxide, N,N-dimethylformamide, acetonitrile, water and the like alone or a mixed solvent thereof.

Step 3 and Step 4

[III-1-6] can be obtained by deprotecting $R^{31a}$ of compound [III-1-3] in the same manner as in production method I-1, step 7, converting the compound to acid chloride according to a conventional method, reacting the acid chloride with a glycine derivative represented by $H_2NC(R^4)(R^5)COOR^{31d}$ in the presence of a base such as triethylamine, diisopropylethylamine, pyridine and the like under low temperature to heating conditions in hexane, chloroform, methylene chloride, ethyl acetate, toluene, tetrahydrofuran and the like alone or a mixed solvent thereof to give compound [III-1-4], and reacting the compound with compound [III-1-5] under low temperature to heating conditions in the presence of a base such as triethylamine, diisopropylethylamine, pyridine and the like in hexane, chloroform, methylene chloride, ethyl acetate, toluene, tetrahydrofuran, 1,4-dioxane and the like alone or a mixed solvent thereof.

Step 5

Compound [III-1-7] can be obtained from compound [III-1-6] in the same manner as in production method I-2, step 1.

Step 6

Compound [III-1-8] can be obtained by deprotection of $R^{31b}$ of compound [III-1-7] in the same manner as in production method I-2, step 4.

Step 7

Compound [III-1-9] can be obtained by removing the amino-protecting group $R^{31c}$ of compound [III-1-8] according to a conventional method. For example, when $R^{31c}$ is a tert-butoxycarbonyl group, compound [III-1-9] can be obtained by stirring under low temperature to room temperature conditions in the presence of an acid such as hydrogen chloride, sulfuric acid, hydrogen bromide, phosphoric acid, acetic acid, trifluoroacetic acid and the like in hexane, chloroform, methylene chloride, ethyl acetate, toluene, methanol, ethanol, 2-propanol, tetrahydrofuran, 1,4-dioxane, acetonitrile, water and the like alone or a mixed solvent thereof.

Step 8

Compound [III-1-10] can be obtained from compound [III-1-9] in the same manner as in production method I-1, step 5.

Step 9

Compound [III-1-11] can be obtained by removing the carboxyl-protecting group of compound [III-1-10] in the same manner as in production method I-1, step 7.

Production Method III-2

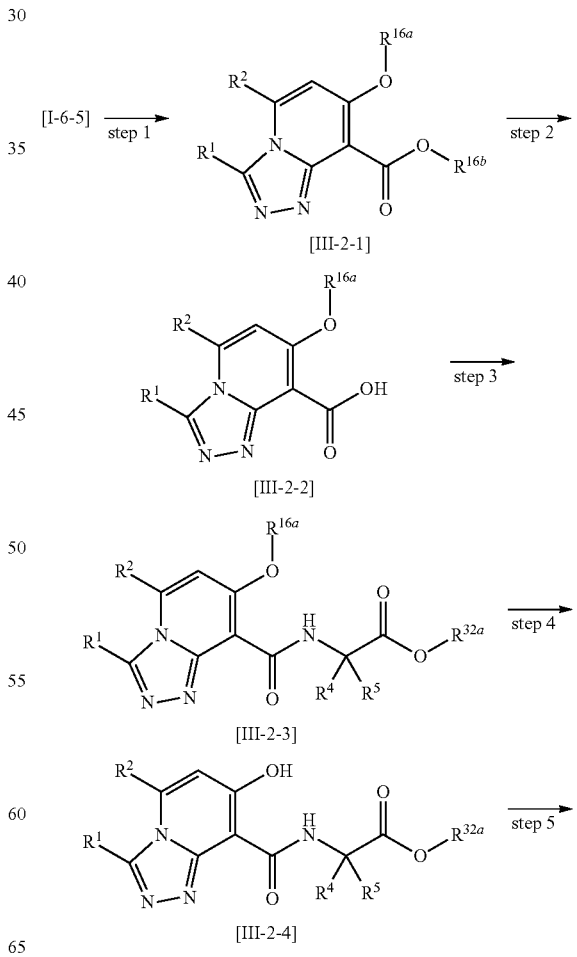

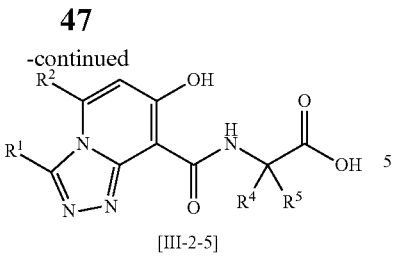

[III-2-5]

wherein $R^{32a}$ is a carboxyl-protecting group such as a methyl group, an ethyl group, a benzyl group, a tert-butyl group and the like, and other symbols are as defined above.

Step 1

Compound [III-2-1] can be obtained from compound [I-6-5] in the same manner as in production method I-1, step 5.

Step 2

Compound [III-2-2] can be obtained by removing the carboxyl-protecting group of compound [III-2-1] in the same manner as in production method I-1, step 7.

Step 3

Compound [III-2-3] can be obtained by condensing compound [III-2-2] with a glycine derivative represented by $H_2NC(R^4)(R^5)COOR^{32a}$ in the same manner as in production method I-2, step 3.

Step 4

Compound [III-2-4] can be obtained by deprotection of $R^{16a}$ of compound [III-2-3] in the same manner as in production method I-2, step 4.

Step 5

Compound [III-2-5] can be obtained by removing the carboxyl-protecting group of compound [III-2-4] in the same manner as in production method I-1, step 7.

Production Method IV-1

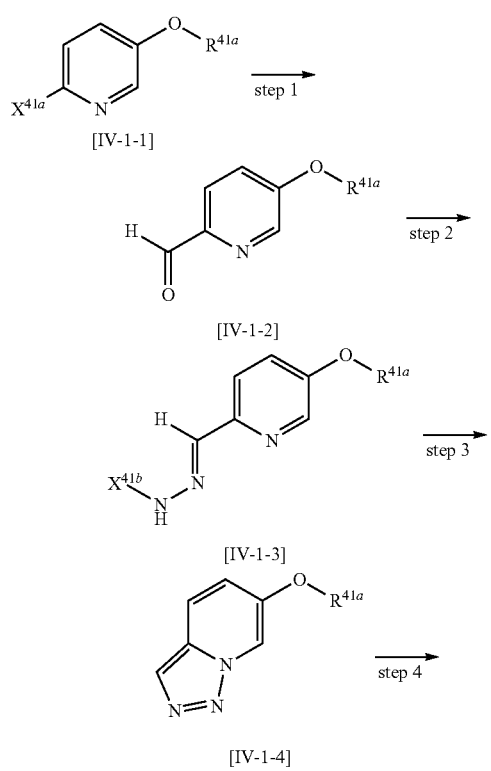

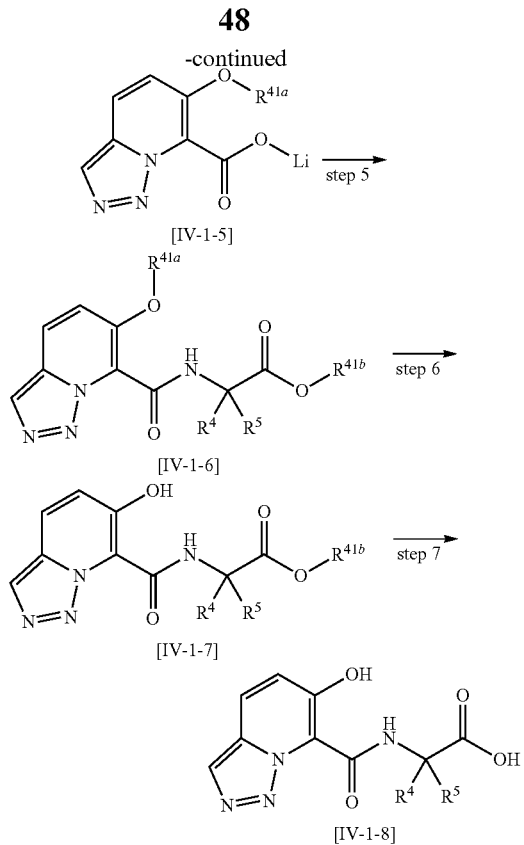

wherein $R^{41a}$ is a hydroxyl-protecting group such as an acetyl group, a benzyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $R^{41b}$ is a carboxyl-protecting group such as a methyl group, an ethyl group, a benzyl group, a tert-butyl group and the like, $X^{41a}$ and $X^{41b}$ are each a halogen atom such as a chlorine atom, a bromine atom, an iodine atom and the like, a leaving group such as a p-toluenesulfonyloxy group, a methanesulfonyloxy group, a trifluoromethanesulfonyloxy group, a p-toluenesulfonyl group, a methanesulfonyl group and the like, and other symbols are as defined above.

Step 1

Compound [IV-1-2] can be obtained by converting the leaving group $X^{41a}$ of compound [IV-1-1] to a formyl group according to a conventional method. Compound [IV-1-2] can be obtained by reacting compound [IV-1-1] with an organic metal reagent such as n-butyllithium, sec-butyllithium, lithium diisopropylamide, lithium bis(trimethylsilyl)amide, sodium bis(trimethylsilyl)amide, potassium bis(trimethylsilyl)amide, lithium amide, sodium amide and the like under low temperature conditions in hexane, benzene, toluene, tetrahydrofuran, diethyl ether, 1,4-dioxane and the like alone or a mixed solvent thereof, and then with N,N-dimethylformamide.

Step 2 and Step 3

Compound [IV-1-4] can be obtained by reacting compound [IV-1-2] with hydrazine having a leaving group $X^{41b}$ under room temperature to under heating conditions in ethyl acetate, chloroform, toluene, 1,4-dioxane, tetrahydrofuran, 1,2-dimethoxyethane, methanol, ethanol, isopropanol, dimethyl sulfoxide, N,N-dimethylformamide, acetonitrile and the like alone or a mixed solvent thereof, then adding a base such as morpholine, piperidine, pyrrolidine and the like, and stirring the mixture.

Step 4
Compound [IV-1-5] can be obtained from compound [IV-1-4] in the same manner as in production method I-1, step 1.

Step 5
Compound [IV-1-6] can be obtained by condensing compound [IV-1-5] with a glycine derivative in the same manner as in production method I-2, step 3.

Step 6
Compound [IV-1-7] can be obtained by deprotection of $R^{41a}$ of compound [IV-1-6] in the same manner as in production method I-2, step 4.

Step 7
Compound [IV-1-8] can be obtained by removing the carboxyl-protecting group of compound [IV-1-7] in the same manner as in production method I-1, step 7.

In this production method, a production method when $R^1$ is a hydrogen atom has been described. When $R^1$ is the aforementioned substituent and other than a hydrogen atom, N,N-dimethylformamide substituted by a desired substituent may be used instead of N,N-dimethylformamide in step 1, and step 2 and the following can be performed by a method similar to the method described in this production method.

EXAMPLES

Now the production method of the compound of the present invention or a pharmaceutically acceptable salt thereof, or a solvate thereof is specifically explained by way of Examples. However, the present invention is not limited by the Examples.

Example 1

Production of {[5-(4-fluoro-3-trifluoromethylphenyl)-7-hydroxy[1,2,4]triazolo[1,5-a]pyridine-8-carbonyl]amino}acetic acid hydrochloride Step 1-1

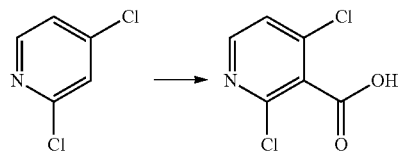

Under a nitrogen stream, diisopropylamine (198 ml) and tetrahydrofuran (1000 ml) were mixed, and n-butyllithium (2.76M, 500 ml) was added dropwise under cooling in dry ice/hexane bath. After stirring in the dry ice/hexane bath for 1 hr, 2,4-dichloropyridine was added dropwise. After stirring under cooling in the dry ice/hexane bath for 1 hr, carbon dioxide was blown until the temperature rise ceased while preventing a temperature of not less than −60° C. Carbon dioxide was further blown for 30 min under cooling in the dry ice/hexane bath, and 4N hydrochloric acid (1000 ml) was added dropwise. The aqueous layer was extracted twice with ethyl acetate (each 1000 ml, 500 ml). The organic layers were combined, dried over sodium sulfate, filtered, and concentrated under reduced pressure. The obtained solid was slurried in hexane to give the compound described in the above-mentioned scheme (243 g, 96%).

$^1$H-NMR (DMSO-D$_6$) δ: 7.74 (1H, d, J=5.6 Hz), 8.47 (1H, d, J=5.6 Hz), 14.53 (1H, br s).

Step 1-2

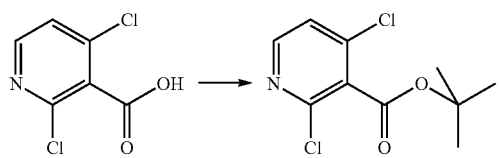

The compound (234 g) obtained in step 1-1 and tetrahydrofuran (1200 ml) were mixed, and boron trifluoride-diethyl ether complex (8 ml) was added. Then, tert-butyl 2,2,2-trichloroacetimidate (361 ml) was added dropwise under ice-cooling. To this reaction mixture were added saturated aqueous sodium hydrogen carbonate solution (1200 ml) and water (1200 ml), and the aqueous layer was extracted with ethyl acetate (1200 ml). The organic layer was washed with saturated brine, dried over sodium sulfate, filtered, and concentrated under reduced pressure. Hexane (1800 ml) was added to the obtained residue. Insoluble material was filtered off, and the filtrate was concentrated under reduced pressure to give the compound described in the above-mentioned scheme (326 g) as a crude product.

$^1$H-NMR (CDCl$_3$) δ: 1.63 (9H, s), 7.31 (1H, d, J=5.2 Hz), 8.31 (1H, d, J=5.2 Hz).

Step 1-3

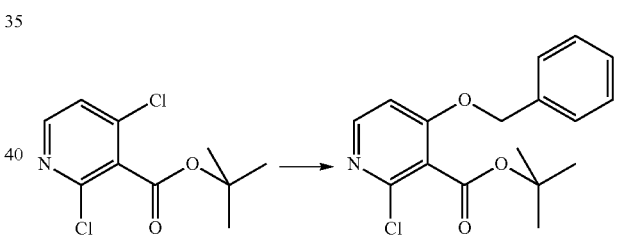

Under a nitrogen stream, sodium hydride (60% oil suspension) (58 g) and N,N-dimethylformamide (1000 ml) were mixed under ice-cooling. The compound (326 g) obtained in step 1-2 was dissolved in N,N-dimethylformamide (300 ml) and added thereto. To this mixture was added a mixture of benzyl alcohol (136 ml) and N,N-dimethylformamide (200 ml). After stirring under ice-cooling for 15 min, sodium hydride (60% oil suspension) (5.2 g) was added. After stirring under ice-cooling for 20 min more, water (3000 ml) was added and the precipitated solid was filtered, and the filtrate was dried under reduced pressure at 50° C. overnight. The solid was purified by column chromatography (eluent: hexane/ethyl acetate=10/1–ethyl acetate alone). The obtained solid was further slurried in hexane to give the object product. The filtrate at this time was concentrated, purified by column chromatography, and slurried in hexane to give the object product. They were combined to give the compound described in the above-mentioned scheme (334 g, 83% yield).

$^1$H-NMR (CDCl$_3$) δ: 1.55 (9H, s), 5.17 (2H, s), 6.83 (1H, d, J=6.0 Hz), 7.32-7.42 (5H, m), 8.24 (1H, d, J=6.0 Hz).

Step 1-4

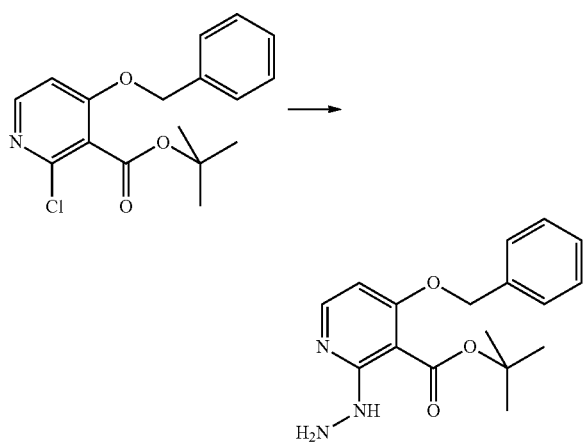

The compound (167 g) obtained in step 1-3, hydrazine monohydrate (127 ml) and 1,4-dioxane (1200 ml) were mixed, and the reaction mixture was stirred at 94° C. for 17 hr. After cooling to room temperature, ethyl acetate (1700 ml) was added, and the mixture was washed successively with saturated aqueous sodium hydrogen carbonate solution (500 ml)/water (500 ml), saturated aqueous sodium hydrogen carbonate solution (250 ml)/water (250 ml), and saturated aqueous sodium hydrogen carbonate solution (200 ml)/water (200 ml). The organic layer was dried over sodium sulfate, filtered, and concentrated under reduced pressure. By performing the operation twice, the compound described in the above-mentioned scheme (266 g) was obtained as a crude product.

$^1$H-NMR (CDCl$_3$) δ: 1.42 (9H, s), 3.98 (2H, br s), 5.09 (2H, s), 6.32 (1H, d, J=5.6 Hz), 7.28-7.45 (5H, m), 7.96 (1H, br s), 8.08 (1H, d, J=5.6 Hz).

Step 1-5

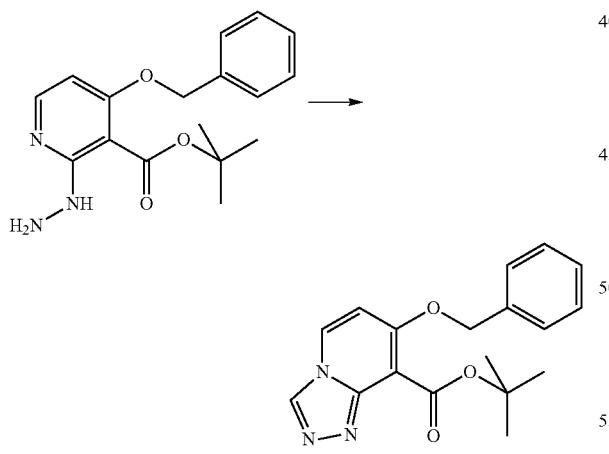

The compound (266 g) obtained in the same manner as in step 1-4 and trimethyl orthoformate (1000 ml) were mixed, p-toluenesulfonic acid monohydrate (80 g) was added, and the mixture was stirred at 56° C. for 1 hr. The reaction mixture was concentrated under reduced pressure, and the obtained residue was slurried in hexane/ethyl acetate=2/1. Furthermore, the residue was slurried in saturated aqueous sodium hydrogen carbonate solution/water=1/1 to give the compound described in the above-mentioned scheme (209 g, 76%).

$^1$H-NMR (DMSO-D$_6$) δ: 1.49 (9H, s), 5.36 (2H, s), 7.22 (1H, d, J=7.6 Hz), 7.32-7.50 (5H, m), 8.62 (1H, d, J=7.6 Hz), 9.13 (1H, s).

Step 1-6

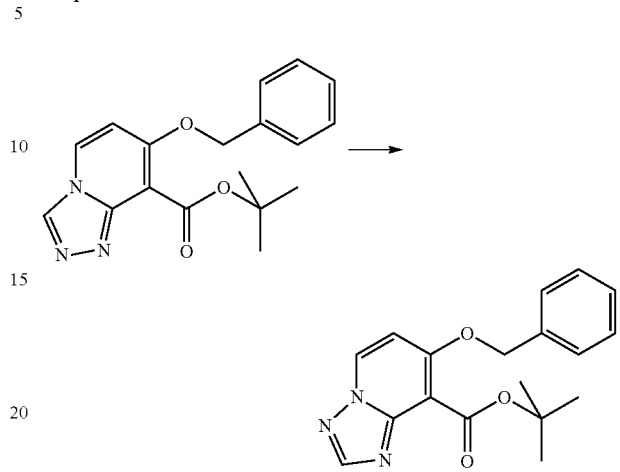

The compound (200 g) obtained in step 1-5 and ethyl acetate (600 ml) were mixed, morpholine (160 ml) was added and the mixture was stirred at 74° C. for 3 hr. The mixture was allowed to cool to room temperature, and water (600 ml) was added. The aqueous layer was extracted with ethyl acetate (400 ml), the organic layers were combined and washed successively with 5% aqueous potassium hydrogensulfate solution (600 ml) and saturated brine. The organic layer was dried over sodium sulfate, filtered, and concentrated under reduced pressure to give the compound described in the above-mentioned scheme (194 g, 97%).

$^1$H-NMR (CDCl$_3$) δ: 1.59 (9H, s), 5.28 (2H, s), 6.85 (1H, d, J=7.6 Hz), 7.33-7.46 (5H, m), 8.29 (1H, s), 8.50 (1H, d, J=7.6 Hz).

Step 1-7

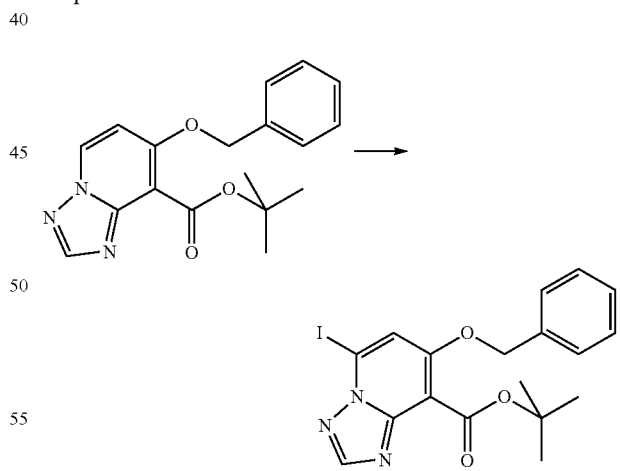

Under a nitrogen stream, the compound (194 g) obtained in step 1-6 and tetrahydrofuran (600 ml) were mixed under cooling in a dry ice/hexane bath, and a solution of iodine (151 g) in tetrahydrofuran (500 ml) was added dropwise. To this mixture was added dropwise 1.6M lithium bis(trimethylsilyl) amide (788 ml) while preventing a temperature of not less than −60° C. After stirring under cooling in a dry ice/hexane bath for 2 hr, 4N hydrochloric acid-ethyl acetate (315 ml) was added dropwise while preventing a temperature of not less than −60° C. To this reaction mixture were added sodium sulfite (76 g), saturated aqueous ammonium chloride solution (1000 ml), water (800 ml) and hexane/ethyl acetate=1/1 (1000 ml). The organic layer was washed successively with saturated aqueous sodium hydrogen carbonate solution (500 ml) and saturated brine (800 ml), dried over sodium sulfate, filtered, and concentrated under reduced pressure to give a crude product. The crude product was slurried in hexane to give the compound described in the above-mentioned scheme (188 g, 70%).

$^1$H-NMR (DMSO-D$_6$) δ: 1.46 (9H, s), 5.39 (2H, s), 7.33-7.51 (5H, m), 7.87 (1H, s), 8.43 (1H, s).

Step 1-8

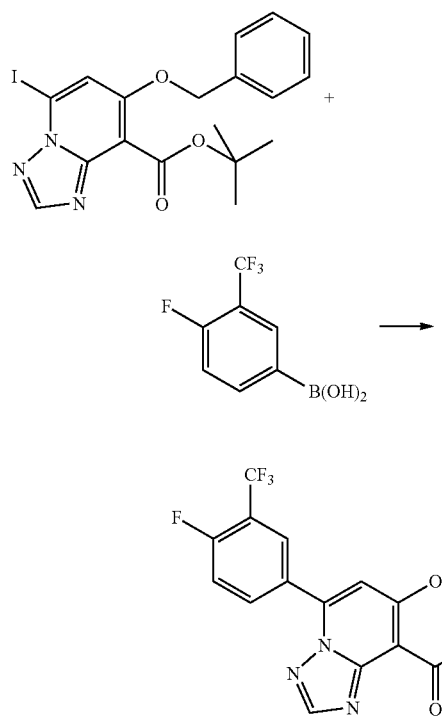

The compound (60 g) obtained in step 1-7, 4-fluoro-3-(trifluoromethyl)phenylboronic acid (29 g), [1,1'-bis(diphenylphosphino)ferrocene]palladium(II) dichloride dichloromethane complex (1:1) (5.4 g), potassium phosphate (113 g) and 1,2-dimethoxyethane (600 ml) were mixed, and the mixture was stirred at 80° C. for 1 hr. Water was added to the reaction mixture, and the mixture was extracted with ethyl acetate. The organic layer was washed with saturated brine, dried over anhydrous magnesium sulfate, filtered and concentrated under reduced pressure. The obtained solid was purified by column chromatography (eluent: chloroform/ethyl acetate=10/1) to give a crude product of the compound described in the above-mentioned scheme. This was slurried in diisopropyl ether/hexane=1/1 (500 ml) to give the compound described in the above-mentioned scheme (45 g, 70%).

$^1$H-NMR (CDCl$_3$) δ: 1.61 (9H, s), 5.33 (2H, s), 6.88 (1H, s), 7.35-7.48 (6H, m), 8.04 (1H, dd, J=6.7, 2.1 Hz), 8.11-8.15 (1H, m), 8.31 (1H, s).

Step 1-9

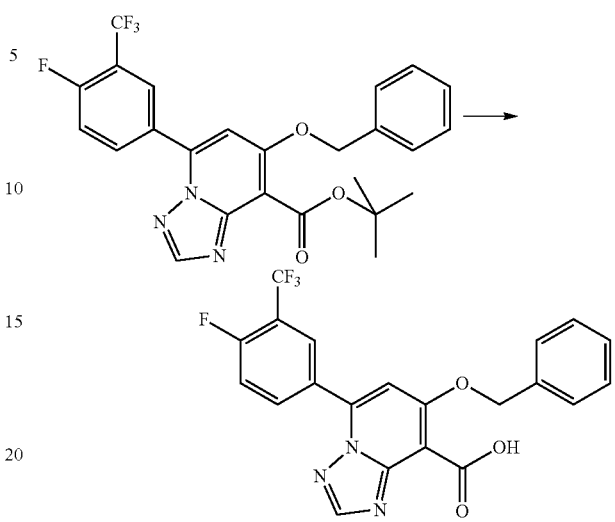

The compound (45 g) obtained in step 1-8 and 1,4-dioxane (450 ml) were mixed, and 4N aqueous sodium hydroxide solution (116 ml) was added at room temperature. After stirring at 100° C. for 17 hr, the reaction mixture was concentrated under reduced pressure. Water (450 ml) was added thereto, and the mixture was neutralized with 6N hydrochloric acid (77 ml) under ice-cooling, and the precipitated solid was collected by filtration to give the compound described in the above-mentioned scheme (43 g).

$^1$H-NMR (DMSO-D$_6$) δ: 5.51 (2H, s), 7.34-7.38 (1H, m), 7.41-7.45 (2H, m), 7.50-7.52 (2H, m), 7.63 (1H, s), 7.80 (1H, dd, J=10.5, 8.9 Hz), 8.40-8.48 (2H, m), 8.48 (1H, s).

Step 1-10

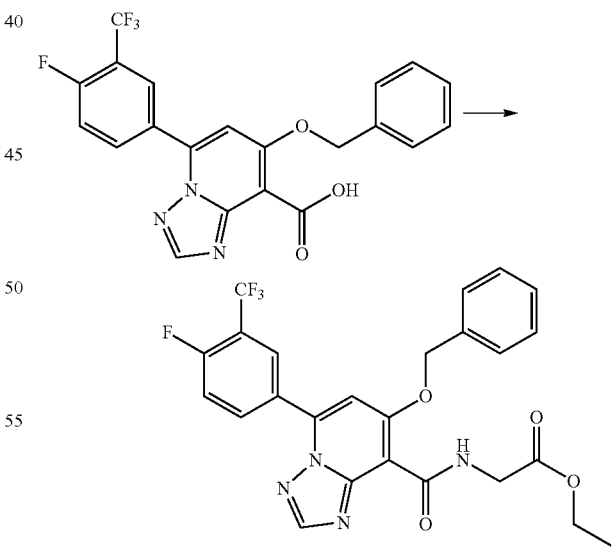

The compound (43 g) obtained in step 1-9, glycine ethylester hydrochloride (15 g), 1-hydroxybenzotriazole hydrate (17 g) and N,N-dimethylformamide (430 ml) were mixed, and triethylamine (15 ml) and 1-ethyl-3-(3-dimethylaminopropyl)carbodiimide hydrochloride (21 g) were added at room temperature. After stirring at room temperature for 1 hr, water (860 ml) and saturated aqueous sodium hydrogen carbonate solution (215 ml) were added, and the precipitated solid was collected by filtration to give the compound described in the above-mentioned scheme (43 g, 84%).

¹H-NMR (CDCl₃) δ: 1.33 (3H, t, J=7.1 Hz), 4.28 (2H, q, J=7.1 Hz), 4.35 (2H, d, J=4.8 Hz), 5.47 (2H, s), 6.95 (1H, s), 7.32-7.43 (4H, m), 7.54 (2H, d, J=7.3 Hz), 8.01 (1H, dd, J=6.4, 2.0 Hz), 8.10-8.14 (1H, m), 8.31 (1H, s), 9.72 (1H, t, J=4.8 Hz).

Step 1-11

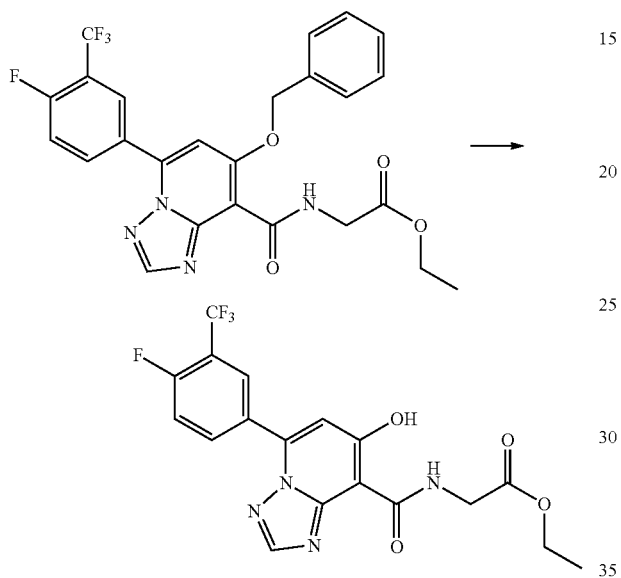

The compound (43 g) obtained in step 1-10 and trifluoroacetic acid (430 ml) were mixed and, after stirring at 80° C. for 6 hr, the reaction mixture was concentrated under reduced pressure. Methanol (86 ml) and water (430 ml) were added to the residue, and the mixture was stirred at room temperature for 30 min, and the precipitated solid was collected by filtration. This was purified by column chromatography (eluent: chloroform/ethyl acetate=10/1) to give the compound described in the above-mentioned scheme (28 g, 79%).

¹H-NMR (CDCl₃) δ: 1.34 (3H, t, J=7.3 Hz), 4.30 (2H, q, J=7.3 Hz), 4.33 (2H, d, J=5.2 Hz), 6.87 (1H, s), 7.41 (1H, dd, J=9.7, 8.9 Hz), 8.16-8.20 (1H, m), 8.24 (1H, dd, J=6.9, 2.4 Hz), 8.26 (1H, s), 10.15 (1H, t, J=5.2 Hz), 14.13 (1H, s).

Step 1-12

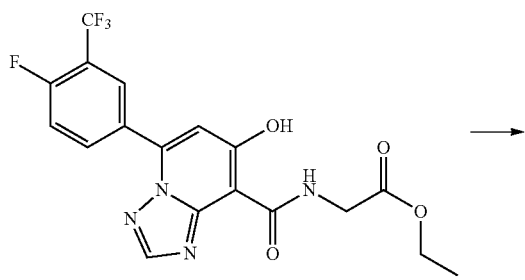

The compound (27 g) obtained in step 1-11 and 2-propanol (540 ml) were mixed, and 4N aqueous lithium hydroxide solution (64 ml) was added at room temperature. After stirring at 70° C. for 1 hr, 6N hydrochloric acid (43 ml) was added. This was allowed to gradually cool with stirring and crystals were precipitated at 37° C. Water (270 ml) was added and the crystals were collected by filtration to give the compound described in the above-mentioned scheme (22 g, 87%).

¹H-NMR (DMSO-D₆) δ: 4.24 (2H, d, J=5.6 Hz), 7.30 (1H, s), 7.77 (1H, dd, J=10.5, 9.3 Hz), 8.36-8.40 (1H, m), 8.47 (1H, d, J=6.9 Hz), 8.60 (1H, s), 9.97 (1H, br s), 14.38 (1H, br s).

The obtained compound was converted to hydrochloride according to a conventional method to give the compound of Example 1.

¹H-NMR (DMSO-D₆) δ: 4.25 (d, 2H, J=5.6 Hz), 7.31 (s, 1H), 7.73-7.82 (m, 1H), 8.34-8.43 (m, 1H), 8.43-8.51 (m, 1H), 8.61 (s, 1H), 9.99 (t, 1H, J=5.6 Hz).

Example 2

Production of [(7-hydroxy-5-phenethyl[1,2,4]triazolo[1,5-a]pyridine-8-carbonyl)amino]acetic acid hydrochloride Step 2-1

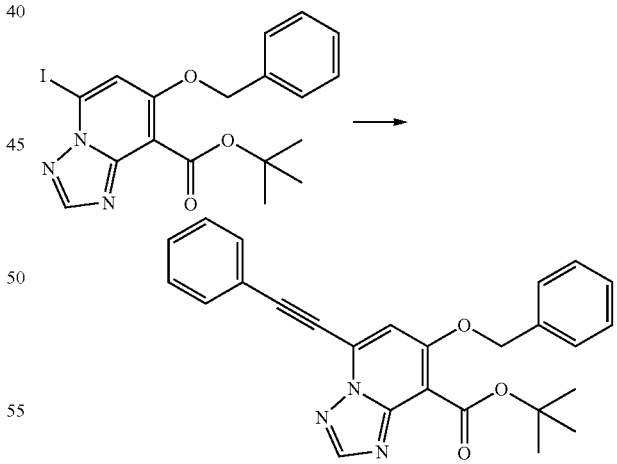

The compound (5.00 g) obtained in step 1-7, toluene (35 ml) and phenylacetylene (1.34 ml) were mixed, and bis(triphenylphosphine)palladium dichloride (0.233 g), copper iodide (0.063 g) and triethylamine (1.85 ml) were successively added under ice-cooling. After stirring at room temperature for 2 hr, 5% aqueous ammonia (35 ml) was added to the reaction mixture. The organic layer was further washed successively with 5% aqueous ammonia, saturated aqueous ammonium chloride solution and saturated brine, and dried over anhydrous magnesium sulfate. After filtration, the filtrate was concentrated under reduced pressure, and the obtained residue was purified by column chromatography (eluent: hexane/ethyl acetate=3/1-1/1). The obtained compound was slurried in hexane to give the compound described in the above-mentioned scheme (3.84 g, 82%).

¹H-NMR (DMSO-D₆) δ: 1.48 (9H, s), 5.42 (2H, s), 7.36 (1H, tt, J=7.1, 1.8 Hz), 7.40-7.45 (2H, m), 7.48 (2H, dt, J=7.0, 1.9 Hz), 7.51-7.58 (3H, m), 7.72 (2H, dd, J=7.7, 1.6 Hz), 7.78 (1H, s), 8.49 (1H, s).

Step 2-2

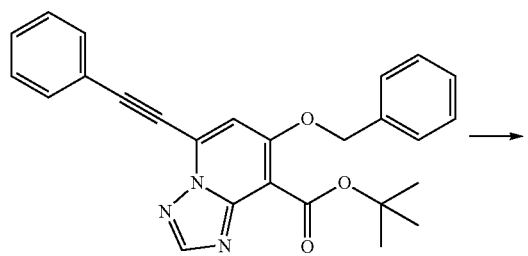

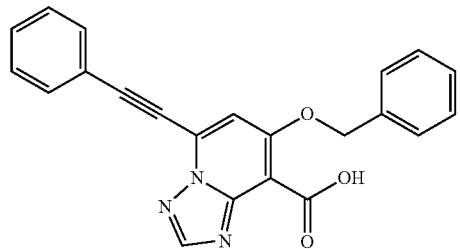

The compound (4.94 g) obtained in step 2-2 and N,N-dimethylformamide (30 ml) were mixed at room temperature, and water (50 ml) was added dropwise at 0° C. over 10 min. The precipitated solid was collected by filtration to give the compound described in the above-mentioned scheme (3.20 g, 98%).

¹H-NMR (DMSO-D₆) δ: 5.45 (2H, s), 7.36 (1H, tt, J=7.4, 2.1 Hz), 7.43 (2H, t, J=7.3 Hz), 7.49 (2H, d, J=7.5 Hz), 7.52-7.60% (3H, m), 7.72 (2H, dd, J=6.7, 1.9 Hz), 7.78 (1H, s), 8.51 (1H, s), 13.59 (1H, s).

Step 2-4

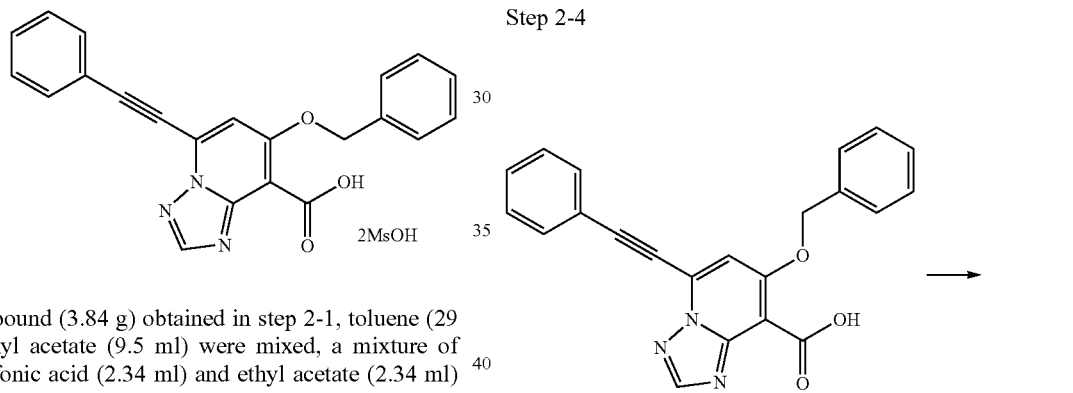

The compound (3.84 g) obtained in step 2-1, toluene (29 ml) and ethyl acetate (9.5 ml) were mixed, a mixture of methanesulfonic acid (2.34 ml) and ethyl acetate (2.34 ml) was added dropwise over 10 min at room temperature with stirring. After stirring at room temperature for 3 hr, ethyl acetate (9.5 ml) was added to the reaction mixture, and the solid was collected by filtration to give the compound described in the above-mentioned scheme (4.94 g, 98%).

¹H-NMR (DMSO-D₆) δ: 2.38 (6H, s), 5.48 (2H, s), 7.37 (1H, tt, J=7.2, 1.7 Hz), 7.41-7.45 (2H, m), 7.48-7.52 (2H, m), 7.53-7.62 (3H, m), 7.71-7.75 (2H, m), 7.86 (1H, s), 8.67 (1H, s).

Step 2-3

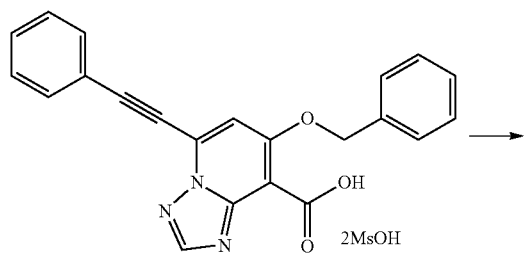

The compound (3.20 g) obtained in step 2-3 was reacted with glycine ethyl ester hydrochloride (1.33 g) by a method similar to Example 1, step 1-10, to give the compound described in the above-mentioned scheme (3.38 g, 81%).

¹H-NMR (DMSO-D₆) δ: 1.21 (3H, t, J=7.1 Hz), 4.10 (2H, d, J=5.7 Hz), 4.13 (2H, q, J=7.5 Hz), 5.44 (2H, s), 7.34 (1H, tt, J=7.2, 1.7 Hz), 7.38-7.43 (2H, m), 7.52-7.58 (5H, m), 7.71-7.74 (2H, m), 7.75 (1H, s), 8.52 (1H, s), 9.18 (1H, t, J=5.8 Hz).

Step 2-5

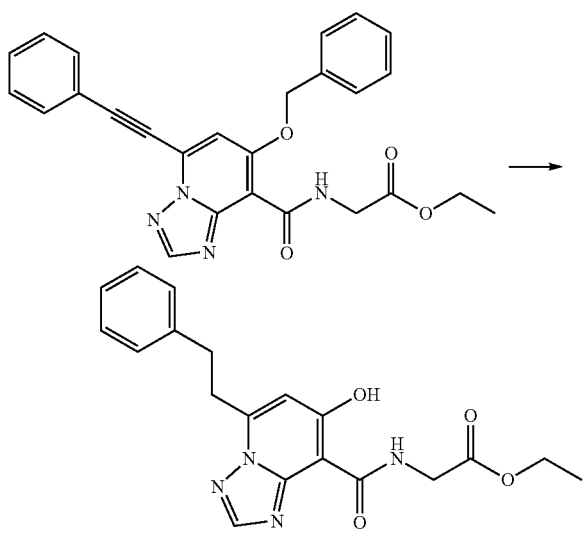

To a solution of the compound (3.38 g) obtained in step 2-4 in tetrahydrofuran (34 ml) and methanol (17 ml) was added 5% palladium carbon (0.34 g), and the mixture was stirred under a hydrogen atmosphere and normal pressure for 4 hr. The reaction mixture was filtered through celite, and concentrated under reduced pressure. The obtained residue was purified by column chromatography (eluent: chloroform/methanol=20/0-20/1) and slurried in hexane/diisopropyl ether=1/1 to give the compound described in the above-mentioned scheme (2.29 g, 83%).

$^1$H-NMR (DMSO-D$_6$) δ: 1.23 (3H, t, J=7.2 Hz), 3.12 (2H, t, J=7.8 Hz), 3.41 (2H, t, J=7.9 Hz), 4.17 (2H, q, J=7.1 Hz), 4.29 (2H, d, J=5.7 Hz), 6.82 (1H, s), 7.18-7.32 (5H, m), 8.58 (1H, s), 9.87 (1H, t, J=5.6 Hz), 14.12 (1H, s).

Step 2-6

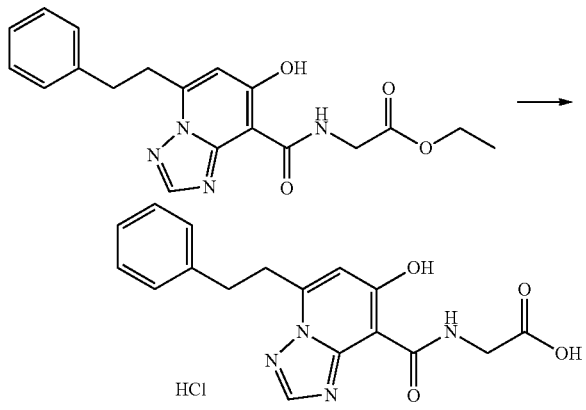

The compound (2.28 g) obtained in step 2-5 was hydrolyzed by a method similar to step 1-12, and the obtained compound was converted to hydrochloride according to a conventional method to give the title compound (2.16 g).

$^1$H-NMR (DMSO-D6) δ: 3.12 (t, 2H, J=7.8 Hz), 3.41 (t, 2H, J=7.8 Hz), 4.21 (d, 2H, J=5.6 Hz), 6.81 (s, 1H), 7.14-7.33 (m, 5H), 8.60 (s, 1H), 9.85 (t, 1H, J=5.6 Hz).

Example 3

Production of [(5-butyl-7-hydroxy[1,2,4]triazolo[1,5-a]pyridine-8-carbonyl)amino]acetic acid hydrochloride Step 3-1

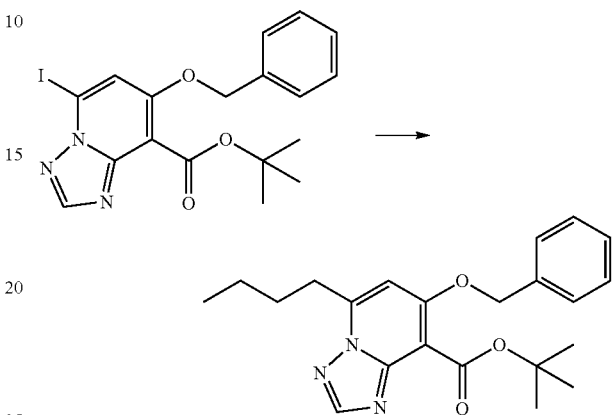

The compound (0.2 g) obtained in step 1-7, [1,1'-bis(diphenylphosphino)ferrocene]palladium(II) dichloride dichloromethane complex (1:1) (0.011 g), butylboronic acid (0.050 g), silver(I) oxide (0.12 g), potassium carbonate (0.15 g) and tetrahydrofuran (1.6 ml) were mixed, and the mixture was stirred at 80° C. for 40 hr. Insoluble material was filtered off, and the filtrate was concentrated under reduced pressure. The residue was purified by column chromatography (eluent: hexane/ethyl acetate=8/2-6/4) to give the compound described in the above-mentioned scheme (0.13 g, 77%).

$^1$H-NMR (DMSO-D$_6$) δ: 0.91 (t, 3H, J=7.7 Hz), 1.28-1.39 (m, 2H), 1.48 (s, 9H), 1.71-1.81 (m, 2H), 3.11 (t, 2H, J=7.7 Hz), 5.38 (s, 2H), 7.23 (s, 1H), 7.32-7.51 (m, 5H), 8.39 (s, 1H).

Step 3-2

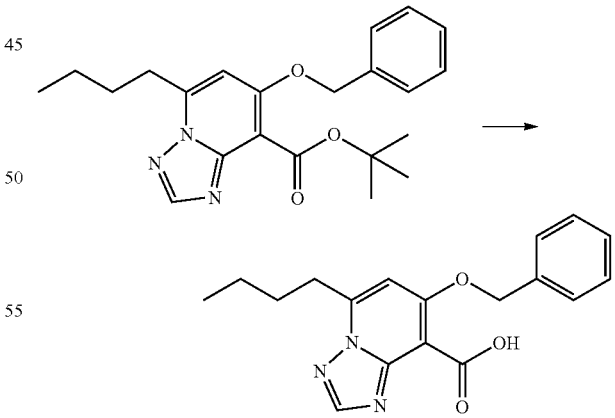

The carboxyl-protecting group of the compound (53.7 g) obtained in step 3-1 was removed in the same manner as in step 2-2 to give a carboxylic acid form as a mixture (69.8 g, 80%) with methanesulfonic acid (290 mol %). The mixture was treated in the same manner as in step 2-3 to give the compound described in the above-mentioned scheme as a mixture (42.8 g, 99%) with methanesulfonic acid (50 mol %).

¹H-NMR (DMSO-D₆) δ: 0.91 (t, 3H, J=7.7 Hz), 1.29-1.40 (m, 2H), 1.71-1.80 (m, 2H), 2.34 (s, 1.5H), 3.14 (t, 2H, J=7.7 Hz), 5.47 (s, 2H), 7.32-7.45 (m, 4H), 7.48-7.53 (m, 2H), 8.73 (s, 1H).

Step 3-3

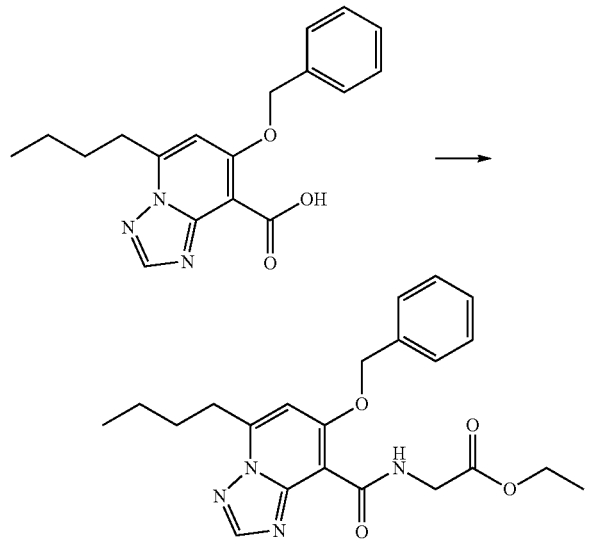

By a method similar to step 1-10, the compound (42.8 g) obtained in step 3-2 was reacted with glycine ethyl ester hydrochloride (19.3 g) to give the compound described in the above-mentioned scheme (43.5 g, 92%).

¹H-NMR (CDCl₃) δ: 0.94 (t, 3H, J=7.5 Hz), 1.31 (t, 3H, J=7.1 Hz), 1.34-1.43 (m, 2H), 1.70-1.79 (m, 2H), 3.11 (t, 2H, J=7.5 Hz), 4.26 (q, 2H, J=7.1 Hz), 4.33 (d, 2H, J=5.2 Hz), 5.41 (s, 2H), 6.69 (s, 1H), 7.29-7.55 (m, 5H), 8.28 (s, 1H), 9.77 (t, 1H, J=5.2 Hz).

Step 3-4

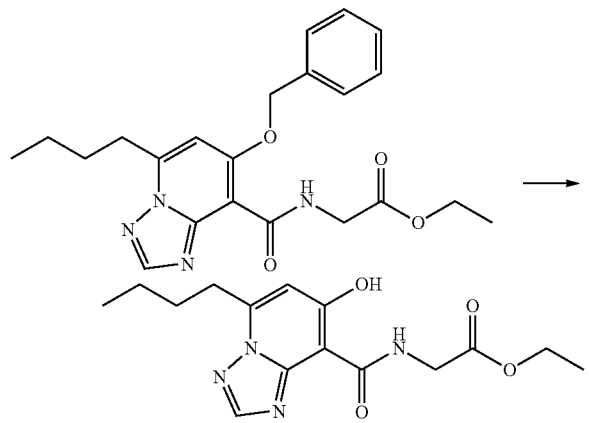

In the same manner as in step 2-5, the compound described in the above-mentioned scheme (5.0 g, 90%) was obtained from the compound (7.2 g) obtained in step 3-3.

¹H-NMR (DMSO-D₆) δ: 0.93° (t, 3H, J=7.5 Hz), 1.22 (t, 3H, J=7.3% Hz), 1.33-1.44 (m, 2H), 1.71-1.81 (m, 2H), 3.09 (t, 2H, J=7.5 Hz), 4.16 (q, 2H, J=7.3 Hz), 4.29 (d, 2H, J=5.6 Hz), 6.85 (s, 1H), 8.54 (s, 1H), 9.88 (br s, 1H), 14.14 (s, 1H).

Step 3-5

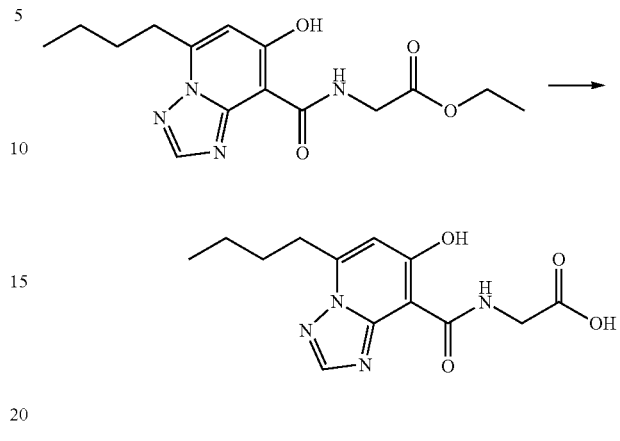

In the same manner as in step 1-12, the compound described in the above-mentioned scheme (4.56 g) was obtained from the compound (4.94 g) obtained in step 3-4.

¹H-NMR (DMSO-D₆) δ: 0.93 (t, 3H, J=7.5 Hz), 1.33-1.44 (m, 2H), 1.71-1.80 (m, 2H), 3.10 (t, 2H, J=7.5 Hz), 4.20 (d, 2H, J=5.2 Hz), 6.85 (s, 1H), 8.55 (s, 1H), 9.84 (br s, 1H), 14.26 (br s, 1H).

Step 3-6

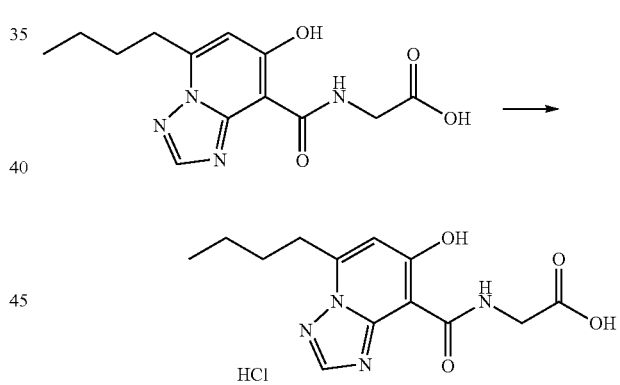

The compound (4.56 g) obtained in step 3-5 and 4N hydrochloric acid/ethyl acetate solution (91 ml) were mixed, and the mixture was stirred at room temperature for 1.5 hr. The reaction suspension was concentrated under reduced pressure, hexane (100 ml) was added to the residue and the mixture was concentrated twice under reduced pressure. To the residue was added a mixed solution (100 ml) of diethyl ether/hexane=1/2 and the mixture was stirred for 30 min. The solid was collected by filtration to give the title compound (4.88 g, 96%).

¹H-NMR (DMSO-D₆) δ: 0.93 (t, 3H, J=7.5 Hz), 1.34-1.44 (m, 2H), 1.71-1.80 (m, 2H), 3.10 (t, 2H, J=7.5 Hz), 4.21 (d, 2H, J=5.6 Hz), 6.86 (s, 1H), 8.57 (s, 1H), 9.83 (t, 1H, J=5.6 Hz).

Example 4

Production of [(5,6-diethyl-7-hydroxy[1,2,4]triazolo[1,5-a]pyridine-8-carbonyl)amino]acetic acid hydrochloride Step 4-1

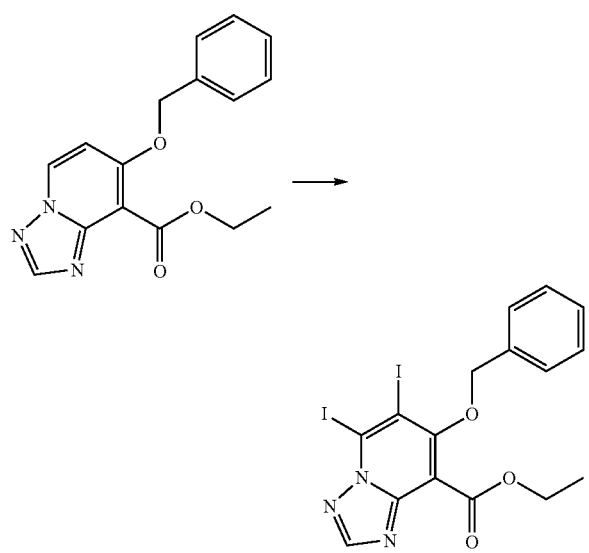

Under a nitrogen stream, the compound (3.98 g) obtained in the same manner as in step 1-6 and tetrahydrofuran (40 ml) were mixed, and a solution of iodine (3.4 g) in tetrahydrofuran (16 ml) was added dropwise under cooling with dry ice/denatured ethanol. To this mixture was added dropwise 1M lithium bis(trimethylsilyl)amide (26.8 ml) over 10 min. After stirring as is for 2.5 hr, the reaction mixture was poured into a mixture of saturated aqueous ammonium chloride solution (40 ml) and water (40 ml) under ice-cooling. To this mixture was added sodium sulfite (1.7 g), and the organic layer was separated from the mixture. The organic layer was concentrated under reduced pressure, the obtained residue was combined with the aqueous layer, and the mixture was extracted twice with ethyl acetate. The organic layer was washed with saturated brine (70 ml), dried over sodium sulfate, sodium sulfate was filtered off, and the filtrate was concentrated under reduced pressure. The obtained residue was purified by column chromatography. The obtained purification product was recrystallized from heptane/chloroform to give the compound described in the above-mentioned scheme (0.295 g, 4%).

$^1$H-NMR (CDCl$_3$) δ: 1.38 (t, 3H, J=7.1 Hz), 4.50 (q, 2H, J=7.1 Hz), 5.22 (s, 2H), 7.36-7.56 (m, 5H), 8.33 (s, 1H).

Step 4-2

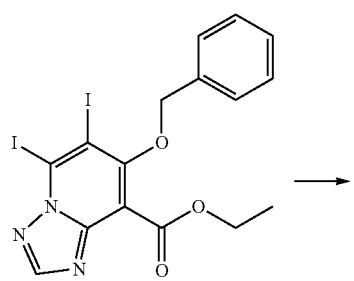

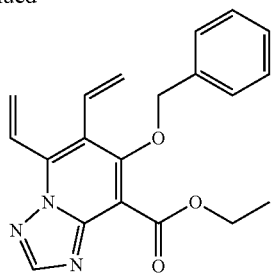

In the same manner as in Example 1, step 1-8, the compound described in the above-mentioned scheme (0.019 g, 30%) was obtained from the compound (0.1 g) obtained in step 4-1.

$^1$H-NMR (CDCl$_3$) δ: 1.38 (t, 3H, J=7.1 Hz), 4.50 (q, 2H, J=7.1 Hz), 5.09 (s, 2H), 5.73 (dd, 1H, J=17.7, 1.4 Hz), 5.76 (dd, 1H, J=11.5, 1.4 Hz), 6.05 (dd, 1H, J=11.5, 1.4 Hz), 6.77 (dd, 1H, J=17.7, 11.7 Hz), 6.87 (dd, 1H, J=17.7, 1.2 Hz), 7.14 (dd, 1H, J=17.7, 11.5 Hz), 7.35-7.44 (m, 5H), 8.37 (s, 1H).

Step 4-3

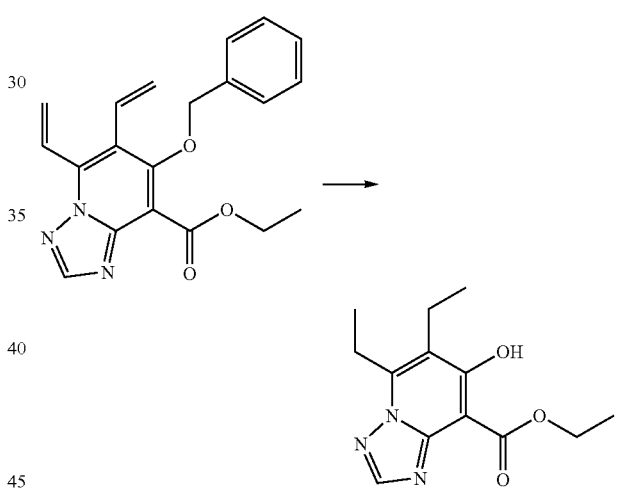

In the same manner as in Example 2, step 2-5, the compound described in the above-mentioned scheme (0.020 g, 75%) was obtained from the compound (0.036 g) obtained in step 4-2.

$^1$H-NMR (CDCl$_3$) δ: 1.23 (t, 3H, J=7.5 Hz), 1.36 (t, 3H, J=7.5% Hz), 1.52 (t, 3H, J=7.3 Hz), 2.78 (q, 2H, J=7.5 Hz), 3.25 (q, 2H, J=7.5 Hz), 4.64 (q, 2H, J=7.3 Hz), 8.26 (s, 1H), 13.10 (s, 1H).

Step 4-4

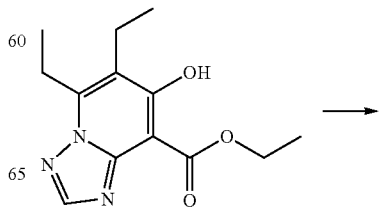

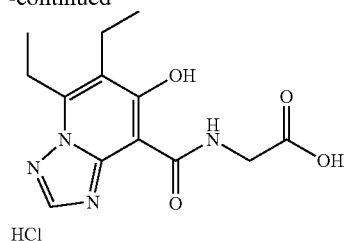

The compound (0.020 g) obtained in step 4-3 and 2-methoxyethanol (2 ml) were mixed, and glycine sodium salt (0.030 g) was added. After stirring at 130° C. for 1.5 hr, the mixture was cooled to room temperature. 1N Hydrochloric acid (0.34 ml) and water (10 ml) were added to the reaction mixture and the mixture was stirred. The precipitate was collected by filtration and dried under reduced pressure. To the obtained solid were added ethyl acetate (1 ml) and 4N hydrochloric acid-ethyl acetate (0.1 ml) and the mixture was stirred at room temperature for 20 min. The solid was collected by filtration to give the title compound (0.052 mg, 67%).

$^1$H-NMR (DMSO-D6) δ: 1.15 (t, 3H, J=7.5 Hz), 1.29 (t, 3H, J=7.5 Hz), 2.72 (q, 2H, J=7.5 Hz), 3.20 (q, 2H, J=7.6 Hz), 4.21 (d, 2H, J=5.6 Hz), 8.52 (s, 1H), 9.95 (t, 1H, J=5.6 Hz).

Example 5

Production of [(7-hydroxy-6-phenethyl[1,2,4]triazolo[1,5-a]pyridine-8-carbonyl)amino]acetic acid hydrochloride Step 5-1

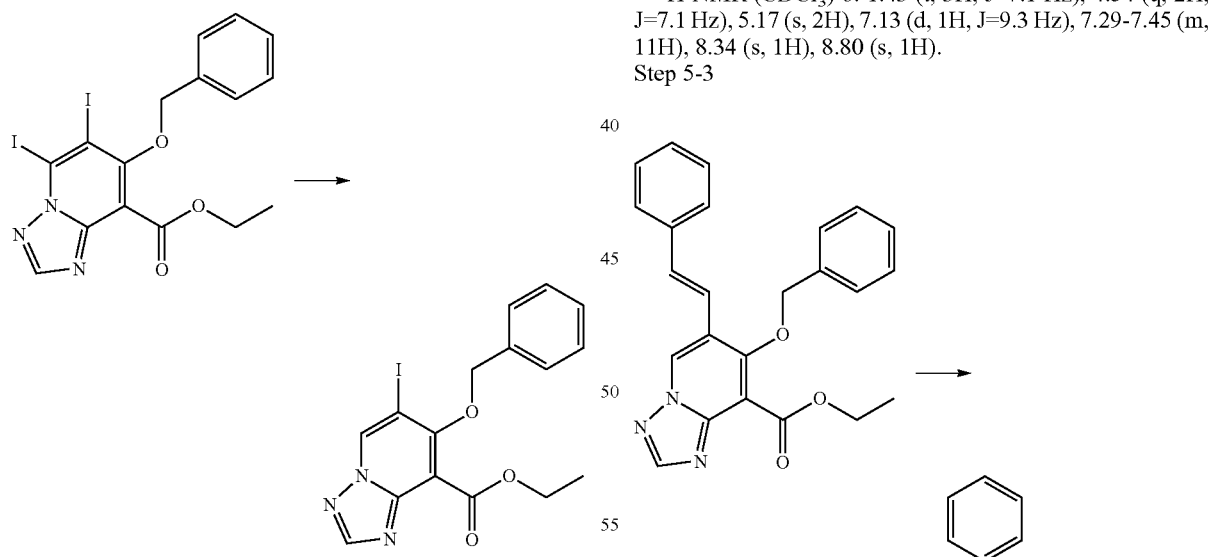

The compound (1.31 g) obtained by a method similar to Example 4, step 4-1, tetrakis(triphenylphosphine)palladium (0) (0.137 g) and tetrahydrofuran (15 ml) were mixed, and tri-n-butyltin hydride (0.7 ml) was added under ice-cooling. After stirring under ice-cooling for 20 min, the mixture was stirred at room temperature for 20 min, and concentrated under reduced pressure. The obtained residue was purified by column chromatography (eluent: hexane/ethyl acetate=10/0-1/1) to give the compound described in the above-mentioned scheme (0.44 g, 44%).

$^1$H-NMR (CDCl$_3$) δ: 1.39 (t, 3H, J=7.2 Hz), 4.51 (q, 2H, J=7.2 Hz), 5.23 (s, 2H), 7.36-7.56 (m, 5H), 8.31 (s, 1H), 8.99 (s, 1H).

Step 5-2

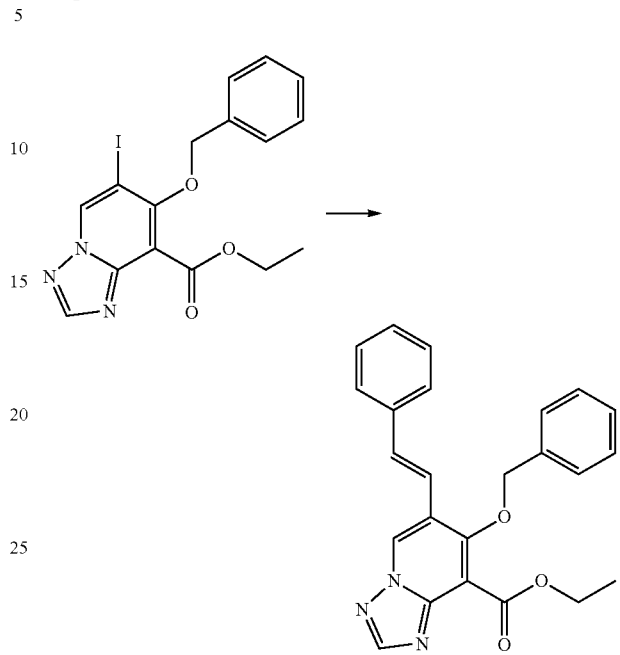

In the same manner as in Example 1, step 1-8, the compound described in the above-mentioned scheme (0.078 g, 109%) was obtained from the compound (0.070 g) obtained in step 5-1.

$^1$H-NMR (CDCl$_3$) δ: 1.43 (t, 3H, J=7.1 Hz), 4.54 (q, 2H, J=7.1 Hz), 5.17 (s, 2H), 7.13 (d, 1H, J=9.3 Hz), 7.29-7.45 (m, 11H), 8.34 (s, 1H), 8.80 (s, 1H).

Step 5-3

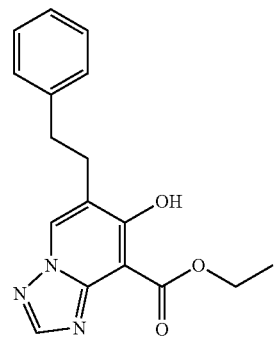

In the same manner as in Example 2, step 2-5, the compound described in the above-mentioned scheme (0.037 g, 72%) was obtained from the compound (0.070 g) obtained in step 5-2.

$^1$H-NMR (CDCl$_3$) δ: 1.54 (t, 3H, J=7.2 Hz), 3.00 (s, 4H), 4.66 (q, 2H, J=7.2 Hz), 7.16-7.31 (m, 5H), 8.20 (s, 1H), 8.23 (s, 1H), 13.17 (s, 1H).

The compound obtained in this step was converted to hydrochloride in the same manner as in Example 4, step 4-4 and according to a conventional method to give the title compound.

$^1$H-NMR (DMSO-D6) δ: 2.93 (s, 4H), 4.22 (d, 2H, J=5.7 Hz), 7.19 (tt, 1H, J=7.1, 1.8 Hz), 7.23-7.31 (m, 4H), 8.50 (s, 1H), 8.78 (s, 1H), 9.97 (s, 1H).

Example 6

Production of [(5-butyl-6-chloro-7-hydroxy[1,2,4]triazolo[1,5-a]pyridine-8-carbonyl)amino]acetic acid hydrochloride Step 6-1

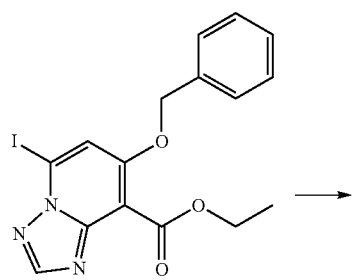

The compound (200 mg) obtained by a method similar to Example 4, step 4-1, hexachloroethane (224 mg) and tetrahydrofuran (4.0 ml) were mixed, and lithium bis(trimethylsilyl)amide (0.473 ml) was added at −78° C. After stirring at −78° C. for 2 hr, the mixture was slowly warmed to −40° C. Thereafter, the mixture was added dropwise to saturated aqueous sodium hydrogen carbonate solution, and ethyl acetate was added. The organic layer was separated from the mixture, and the aqueous layer was extracted twice with ethyl acetate. The organic layers were combined, washed twice with saturated brine, dried over sodium sulfate, and concentrated under reduced pressure. The concentrated residue was purified by column chromatography (eluent: hexane/ethyl acetate=3/1-2/1) to give a crude product (180 mg) containing the compound described in the above-mentioned scheme as a main component.

Step 6-2

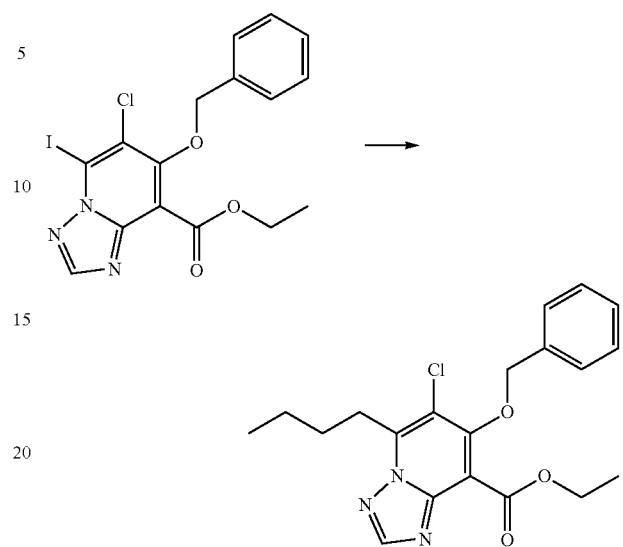

In the same manner as in Example 3, step 3-1, the compound described in the above-mentioned scheme (71 mg) was obtained from the compound (180 mg) obtained in step 6-1.

$^1$H-NMR (DMSO-D$_6$) δ: 0.94 (3H, t, J=7.5 Hz), 1.28 (3H, t, J=7.1 Hz), 1.37-1.47 (2H, m), 1.68-1.75 (2H, m), 3.32-3.37 (2H, m), 4.37 (2H, q, J=7.1 Hz), 5.19 (2H, s), 7.37-7.52 (5H, m), 8.57 (1H, s).

Step 6-3

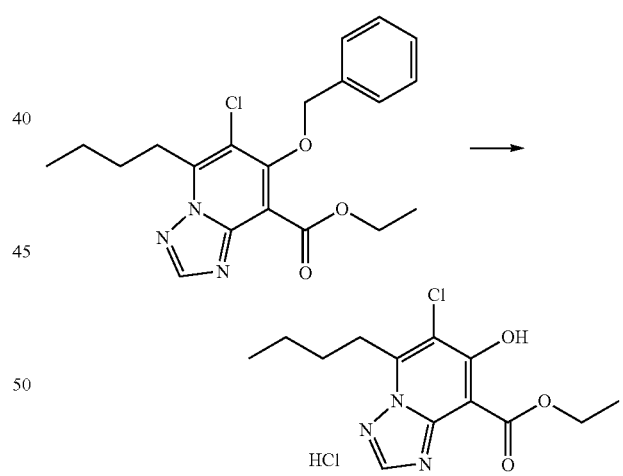

The compound (70 mg) obtained in step 6-2 and trifluoroacetic acid (1 ml) were mixed, and the mixture was stirred at room temperature for 3 hr. To this reaction mixture was added chloroform and the mixture was concentrated under reduced pressure. To the concentrated residue was added 4N hydrochloric acid-ethyl acetate (1 ml) and the mixture was stirred. Hexane (3 ml) was added and the mixture was stirred. The solid was collected by filtration to give the compound described in the above-mentioned scheme (50 mg, 83%).

$^1$H-NMR (DMSO-D$_6$) δ: 0.92 (3H, t, J=7.3 Hz), 1.31 (3H, t, J=7.1 Hz), 1.37-1.45 (2H, m), 1.62-1.69 (2H, m), 3.17 (2H, t, J=7.7 Hz), 4.35 (2H, q, J=7.1 Hz), 8.69 (1H, s).

Step 6-4

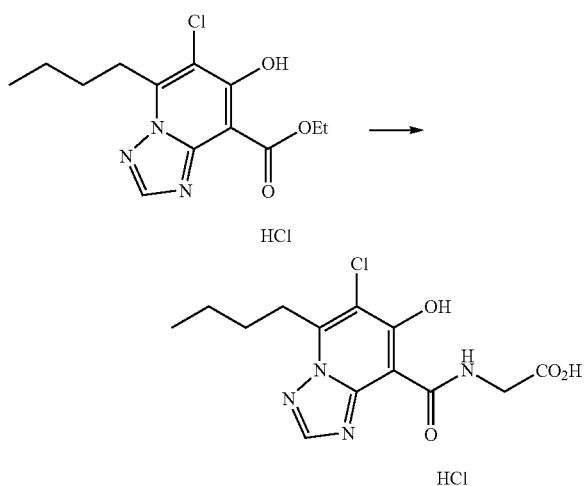

In the same manner as in Example 4, step 4-4, the compound described in the above-mentioned scheme (48 mg, 88%) was obtained from the compound (50 mg) obtained in step 6-3.

$^1$H-NMR (DMSO-D$_6$) δ: 0.93 (t, 3H, J=7.3 Hz), 1.36-1.47 (m, 2H), 1.64-1.72 (m, 2H), 3.15-3.28 (m, 2H), 4.15 (d, 2H, J=2.8 Hz), 8.74 (br s, 1H), 10.20 (br s, 1H).

Example 7

Production of [(7-hydroxy-2-methyl-5-phenethyl[1,2,4]triazolo[1,5-a]pyridine-8-carbonyl)amino]acetic acid hydrochloride Step 7-1

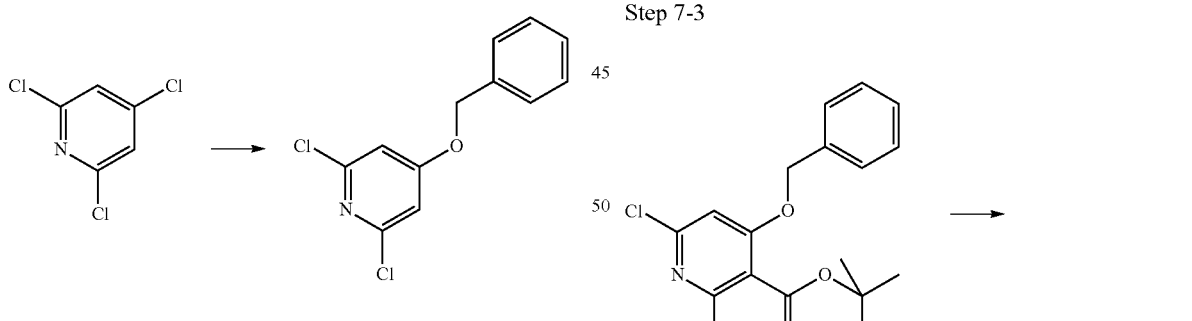

2,4,6-Trichloropyridine (50 g) and N,N-dimethylformamide (400 ml) were mixed, and sodium hydride (60% oil suspension) (11.5 g) was added by portions under ice-cooling. To this mixture was added dropwise under ice-cooling benzyl alcohol (28 ml) over 40 min, and the mixture was stirred at the same temperature for 3 hr. Water (550 ml) was added dropwise under ice-cooling and the resulting solid was collected by filtration to give the compound described in the above-mentioned scheme (50 g, 72%).

$^1$H-NMR (CDCl$_3$) δ: 5.11 (s, 2H), 6.86 (s, 2H), 7.36-7.46 (m, 5H).

Step 7-2

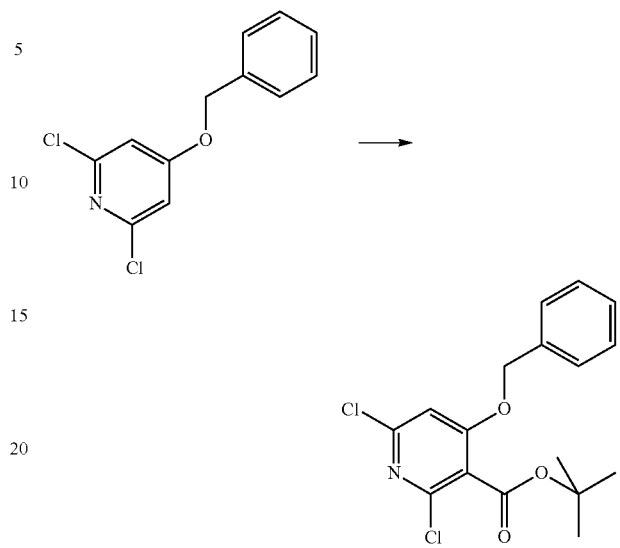

Under cooling in a dry ice/acetone bath, tetrahydrofuran (250 ml) and n-butyllithium (1.65M, 119 ml) were mixed, a solution of the compound (50 g) obtained in step 7-1 in tetrahydrofuran (110 ml) was added dropwise over 30 min. To this mixture was added dropwise a solution of di-tert-butyldicarbonate (45 ml) in tetrahydrofuran (100 ml) over 1 hr, and the mixture was stirred at the same temperature for 30 min. Water (450 ml) was added to quench the reaction, ethyl acetate (200 ml) was added to separate the organic layer and the organic layer was washed with water (200 ml) and saturated brine (200 ml). The organic layer was concentrated under reduced pressure and the residue was purified by column chromatography (eluent: hexane/ethyl acetate=50/0-11/1) and the obtained solid was further slurried in hexane (100 ml) to give the compound described in the above-mentioned scheme (15.7 g, 31%).

$^1$H-NMR (CDCl$_3$) δ: 1.53 (s, 9H), 5.11 (s, 2H), 6.86 (s, 1H), 7.32-7.46 (m, 5H).

Step 7-3

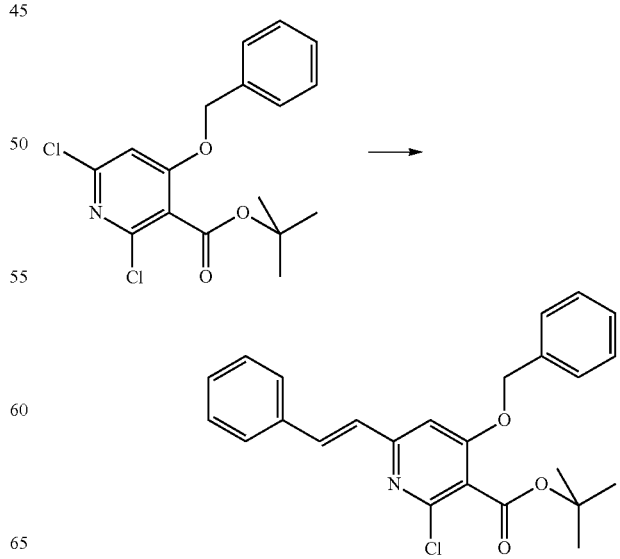

The compound (15 g) obtained in step 7-2 and 1,4-dioxane (150 ml) were mixed, potassium carbonate (18 g), phenylvinylboric acid (7.1 g), [1,1'-bis(diphenylphosphino)ferrocene]palladium(II) dichloride dichloromethane complex (1:1) (1.8 g) and water (45 ml) were added and the mixture was stirred at 80° C. for 1.5 hr with heating. Phenylvinylboric acid (0.64 g) was added and the mixture was stirred for 1.5 hr. The mixture was cooled to room temperature, and water, ethyl acetate and saturated brine were added to separate the organic layer. The organic layer was concentrated under reduced pressure and the obtained residue was purified by column chromatography (eluent: chloroform). To the obtained solid was added isopropyl alcohol (100 ml) and the mixture was slurried at 70° C. for 0.5 hr and under ice-cooling to give the compound described in the above-mentioned scheme (11.5 g, 62%).

$^1$H-NMR (CDCl$_3$) δ: 1.55 (s, 9H), 5.21 (s, 2H), 6.87 (s, 1H), 7.01 (d, 1H, J=15.9 Hz), 7.30-7.44 (m, 8H), 7.56 (d, 2H, J=7.1 Hz), 7.65 (d, 1H, J=16.1 Hz).

Step 7-4

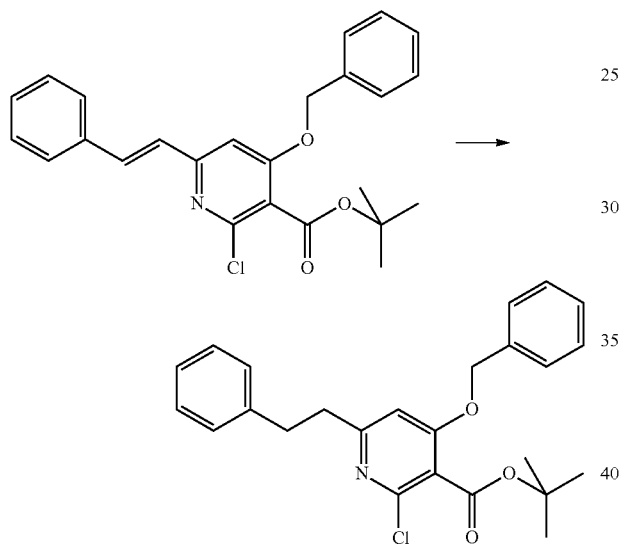

The compound (11.5 g) obtained in step 7-3, ethyl acetate (120 ml) and 2% platinum-carbon (2.5 g) were mixed, and the mixture was stirred under a hydrogen atmosphere (3.8 kgf/cm$^2$) at room temperature for 23 hr. The reaction mixture was filtered through celite, and the filtrate was concentrated under reduced pressure to give the compound described in the above-mentioned scheme (11.5 g, 100%).

$^1$H-NMR (CDCl$_3$) δ: 1.55 (s, 9H), 3.02 (br s, 4H), 5.05 (s, 2H), 6.55 (s, 1H), 7.16-7.41 (m, 10H).

Step 7-5

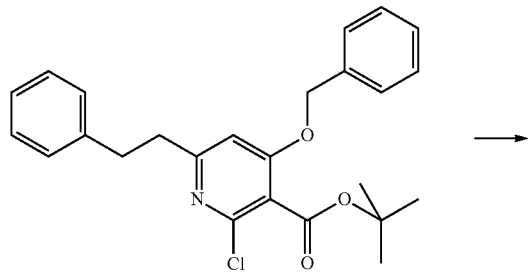

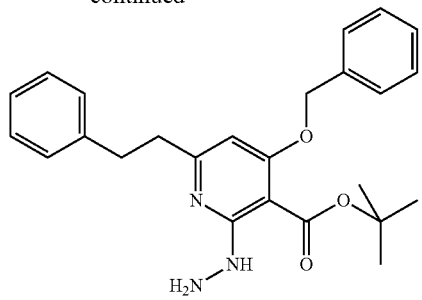

In the same manner as in Example 1, step 1-4, the compound described in the above-mentioned scheme (11.9 g, 104%) was obtained from the compound (11.5 g) obtained in step 7-4.

$^1$H-NMR (CDCl$_3$) δ: 1.39 (s, 9H), 2.92 (t, 2H, J=8.2 Hz), 3.03 (t, 2H, J=8.2 Hz), 4.05 (br s, 2H), 5.00 (s, 2H), 6.10 (s, 1H), 7.16-7.43 (m, 10H), 8.10 (s, 1H).

Step 7-6

The compound (126 mg) obtained in step 7-5, p-toluenesulfonic acid monohydrate (50 mg) and trimethyl orthoformate (1 ml) were mixed, toluene (1 ml) was added and the mixture was heated at 60° C. for 1 hr. The reaction mixture was added dropwise at room temperature to saturated aqueous sodium hydrogen carbonate solution, and ethyl acetate was added to separate the organic layer. The organic layer was concentrated under reduced pressure and the concentrated residue was purified by thin layer chromatography (eluent: chloroform/methanol=9:1) to give the compound described in the above-mentioned scheme (32 mg, 24%).

$^1$H-NMR (CD$_3$OD) δ: 1.51 (9H, s), 2.93 (3H, s), 3.06 (2H, t, J=7.6 Hz), 3.52 (2H, t, J=7.6 Hz), 5.16 (2H, s), 6.72 (1H, s), 7.14-7.48 (10H, m).

Step 7-7

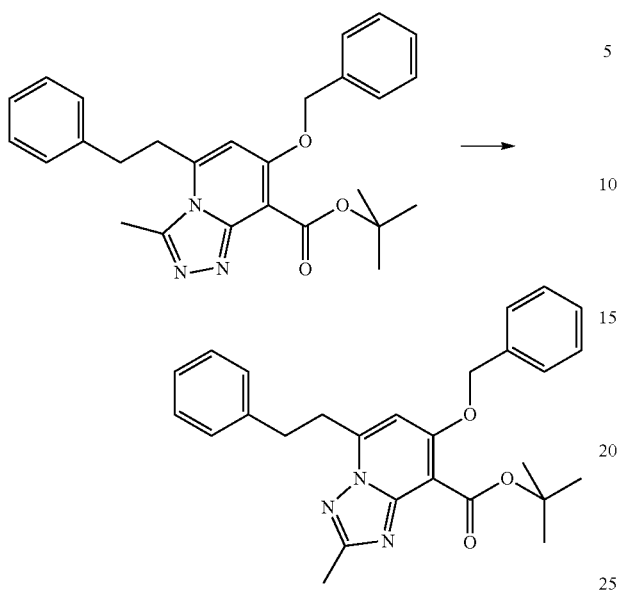

In the same manner as in Example 1, step 1-6, the compound described in the above-mentioned scheme (29 mg, 53%) was obtained from the compound (55 mg) obtained in step 7-6.

$^1$H-NMR (CD$_3$OD) δ: 1.49 (9H, s), 2.52 (3H, s), 3.13 (2H, t, J=7.6 Hz), 3.42 (2H, t, J=7.7 Hz), 5.16 (2H, s), 6.83 (1H, s), 7.15-7.19 (3H, m), 7.24-7.28 (2H, m), 7.32-7.44 (5H, m).

Step 7-8

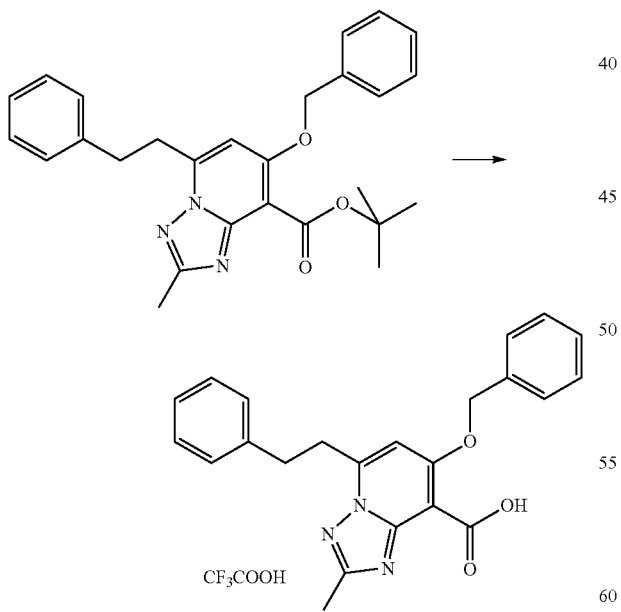

The compound (54 mg) obtained in step 7-7 and chloroform (0.5 ml) were mixed, trifluoroacetic acid (0.22 ml) was added, and the mixture was stirred at room temperature for 2 hr. The reaction mixture was concentrated under reduced pressure, and the residue was azeotropically distilled with toluene to give a crude product (69 mg) containing the compound described in the above-mentioned scheme as a main component.

The compound obtained in this step was treated in the same manner as in Example 1, step 1-10 to step 1-12, and the obtained compound was converted to hydrochloride by a conventional method to give the title compound.

$^1$H-NMR (DMSO-D6) δ: 2.52 (s, 3H), 3.10 (t, 2H, J=7.8 Hz), 3.35 (t, 2H, J=7.8 Hz), 4.19 (d, 2H, J=5.7 Hz), 6.69 (s, 1H), 7.18-7.31 (m, 5H), 9.81 (t, 1H, J=5.5 Hz).

Example 8

Production of {[8-(3,3-dimethyl-butyl)-6-hydroxy[1,2,4]triazolo[1,5-a]pyridine-5-carbonyl]amino}acetic acid hydrochloride Step 8-1

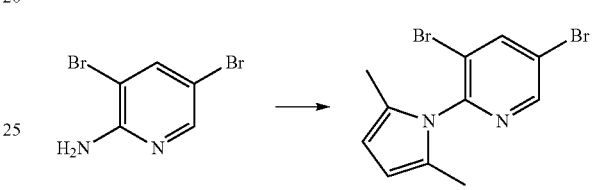

2-Amino-3,5-dibromopyridine (50.4 g), 2,5-hexanedione (23.5 g) and p-toluenesulfonic acid monohydrate (2.7 g) were dissolved in toluene (300 ml), and the mixture was heated under reflux for 5 hr while removing water. The mixture was allowed to cool to room temperature, ethyl acetate was added, and the mixture was washed successively with saturated aqueous sodium hydrogen carbonate solution, water and saturated brine (once each). The organic layer was dried over sodium sulfate, filtered, and concentrated under reduced pressure to give a crude product (66.6 g) of the compound described in the above-mentioned scheme.

$^1$H-NMR (CDCl$_3$) δ: 2.00 (6H, s), 5.92 (2H, s), 8.22 (1H, d, J=2.4 Hz), 8.63 (1H, d, J=2.4 Hz).

Step 8-2

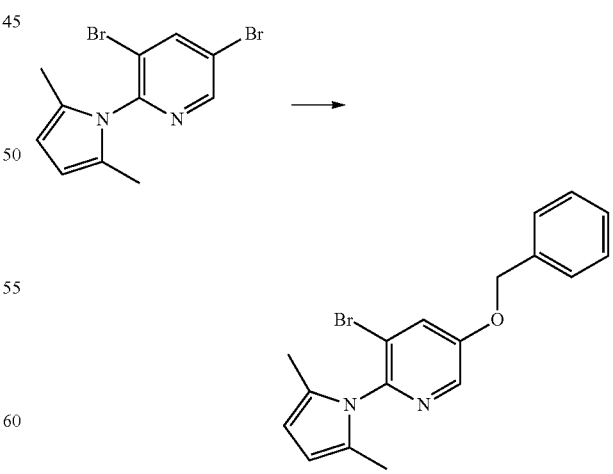

In the same manner as in Example 1, step 1-3, the compound described in the above-mentioned scheme (58.4 g, 82%) was obtained from the compound (66.6 g) obtained in step 8-1.

¹H-NMR (CDCl₃) δ: 1.99 (6H, s), 5.15 (2H, s), 5.89 (2H, s), 7.37-7.48 (5H, m), 7.64 (1H, d, J=2.8 Hz), 8.31 (1H, d, J=2.8 Hz).

Step 8-3

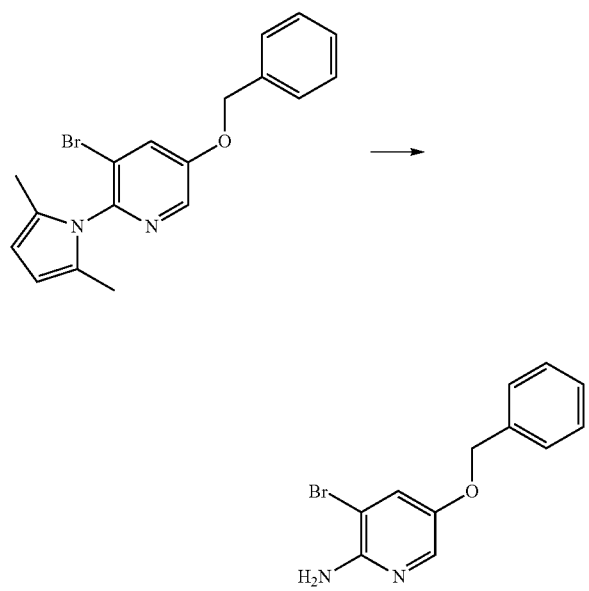

The compound (58.4 g) obtained in step 8-2, hydroxylammonium chloride (233 g), ethanol (600 ml) and water (350 ml) were mixed. To this mixture was added dropwise at room temperature triethylamine (46 ml), ethanol (100 ml) was added and the mixture was heated under reflux at a bath temperature of 95° C. for 89 hr. The reaction mixture was ice-cooled, and 50% aqueous sodium hydroxide solution (96 ml), 8N aqueous sodium hydroxide solution (134 ml) and saturated aqueous sodium hydrogen carbonate solution (50 ml) were successively added. Water (1800 ml) was added at room temperature, the mixture was stirred for 1 hr and a precipitated solid was collected by filtration. The precipitated solid was dried under reduced pressure overnight and the crude product (49 g) was slurried in 2-propanol (120 ml) to give the compound described in the above-mentioned scheme (34.3 g, 75%).

¹H-NMR (CDCl₃) δ: 4.60 (2H, br s), 5.00 (2H, s), 7.31-7.40 (5H, m), 7.41 (1H, d, J=2.8 Hz), 7.83 (1H, d, J=2.8 Hz).

Step 8-4

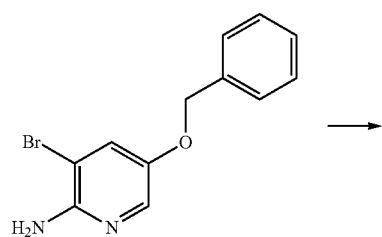

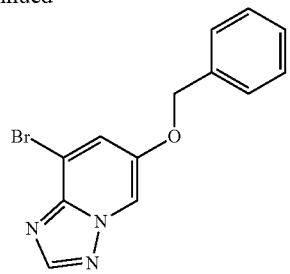

The compound (7.25 g) obtained in step 8-3, N,N-dimethylformamide (11 ml) and N,N-dimethylformamide dimethyl acetal (11 ml) were mixed, and the mixture was stirred with heating at 130° C. for 15 min. After stirring at room temperature for 20 min, the mixture was concentrated under reduced pressure. To the obtained residue were added methanol (58 ml) and pyridine (4.2 ml), and hydroxylamine-O-sulfonic acid (4.1 g) was added to the mixture under ice-cooling. After stirring at room temperature overnight, water (29 ml) and saturated aqueous sodium hydrogen carbonate solution (58 ml) were added under ice-cooling, and the mixture was stirred at room temperature for 1 hr. The resulting solid was collected by filtration to give the compound described in the above-mentioned scheme (6.13 g, 78%).

¹H-NMR (CDCl₃) δ: 5.09 (s, 2H), 7.36-7.45 (m, 5H), 7.66 (d, 1H, J=2.0 Hz), 8.19 (d, 1H, J=2.0 Hz), 8.29 (s, 1H).

Step 8-5

In the same manner as in Example 1, step 1-1, the compound described in the above-mentioned scheme (5.67 g, 49%) was obtained from the compound (10 g) obtained in step 8-4.

¹H-NMR (DMSO-D₆) δ: 5.33 (s, 2H), 7.31-7.49 (m, 5H), 8.37 (s, 1H), 8.56 (s, 1H).

Step 8-6

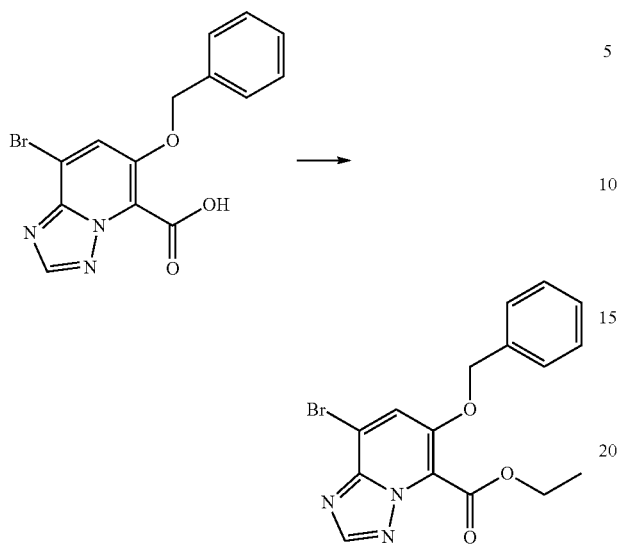

To the compound (5.68 g) obtained in step 8-5 was added toluene (57 ml), and N,N-dimethylformamide diethyl acetal (4.5 ml) was added in 3 portions at 80° C. After completion of the reaction, the mixture was concentrated under reduced pressure, and the obtained residue was purified by column chromatography (eluent: chloroform/ethyl acetate=10/1-4/1). Hexane was added to the obtained compound, and the precipitated solid was slurried to give the compound described in the above-mentioned scheme (4.68 g, 69%).

$^1$H-NMR (CDCl$_3$) δ: 1.39 (t, 3H, J=7.1 Hz), 4.53 (q, 2H, J=7.1 Hz), 5.21 (s, 2H), 7.35-7.43 (m, 5H), 7.72 (s, 1H), 8.38 (s, 1H).

Step 8-7

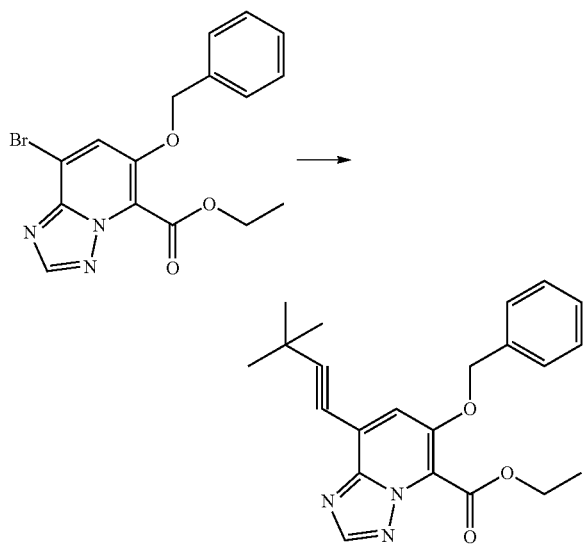

The compound (100 mg) obtained in step 8-6, tert-butylacetylene (0.1 ml), bis(triphenylphosphine)palladium(II) dichloride (18 mg), and copper iodide(I) (5 mg) were added to a screw bottle. To this mixture were added tetrahydrofuran (0.4 ml) and triethylamine (0.8 ml) and the bottle was tightly sealed. The mixture was stirred at room temperature for 1 hr, passed though a small amount of silica gel and concentrated under reduced pressure. The residue was purified twice by thin layer chromatography (eluent: hexane/ethyl acetate=2/1) to give the compound described in the above-mentioned scheme (85 mg, 85%).

Step 8-8

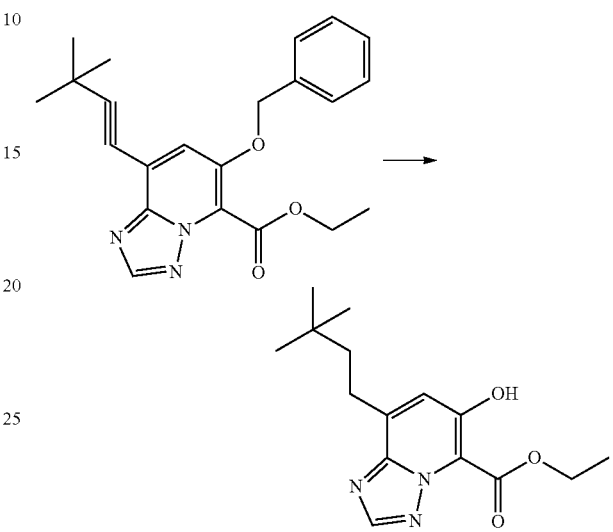

In the same manner as in Example 2, step 2-5, the compound described in the above-mentioned scheme (62 mg, 94%) was obtained from the compound (85 mg) obtained in step 8-7.

In the same manner as in Example 4, step 4-4, the title compound was obtained from the compound obtained in this step.

$^1$H-NMR δ: 0.98 (s, 9H), 1.57-1.66 (m, 2H), 2.89-2.99 (m, 2H), 4.25 (d, 2H, J=5.4 Hz), 7.42 (s, 1H), 8.64 (s, 1H), 10.42 (t, 1H, J=5.4 Hz), 13.28 (s, 1H).

Example 9

Production of [(7-hydroxy-6-phenyl[1,2,4]triazolo[4,3-a]pyridine-8-carbonyl)amino]acetic acid Step 9-1

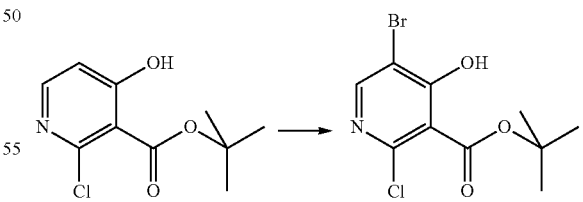

The hydroxyl-protecting group of the compound obtained in Example 1, step 1-3 was removed in the same manner as in Example 2, step 2-5. To a solution of the obtained compound (3.30 g) in chloroform (30 ml) was added under ice-cooling N-bromosuccinimide (2.82 g). After stirring at room temperature for 5 hr, the reaction mixture was separated by adding saturated aqueous sodium hydrogen carbonate solution (20 ml). The organic layer was further washed with aqueous sodium sulfite solution and saturated brine, and dried over anhydrous magnesium sulfate. After filtration, the mixture was concentrated under reduced pressure to give the compound described in the above-mentioned scheme (5.37 g) as a crude product.

$^1$H-NMR (CDCl$_3$) δ: 1.66 (9H, s), 8.39 (1H, s), 12.77 (1H, s).

Step 9-2

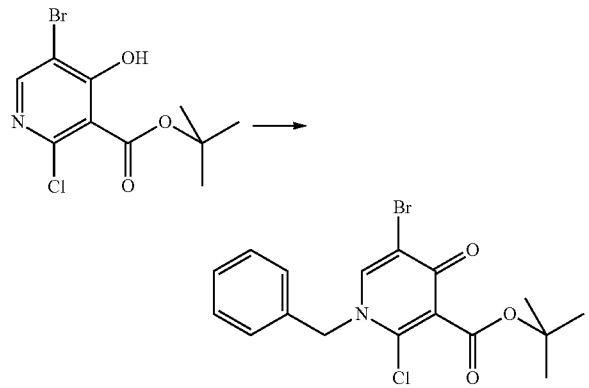

To a solution of the compound (5.37 g) obtained in step 9-1 in N,N-dimethylformamide were added under ice-cooling potassium carbonate (2.19 g) and benzyl bromide (1.88 ml) and the mixture was stirred at room temperature for 20 hr. The reaction mixture was separated by adding water (50 ml) and ethyl acetate (50 ml). The organic layer was further washed with saturated brine, dried over anhydrous magnesium sulfate, and concentrated under reduced pressure. The residue was purified by column chromatography (eluent: hexane/ethyl acetate=3/1-1/2) to give the compound described in the above-mentioned scheme (3.73 g, 2 steps 65%).

$^1$H-NMR (CDCl$_3$) δ: 1.58 (9H, s), 5.21 (2H, s), 7.19-7.21 (2H, m), 7.37-7.46 (3H, m), 7.76 (1H, s).

Step 9-3

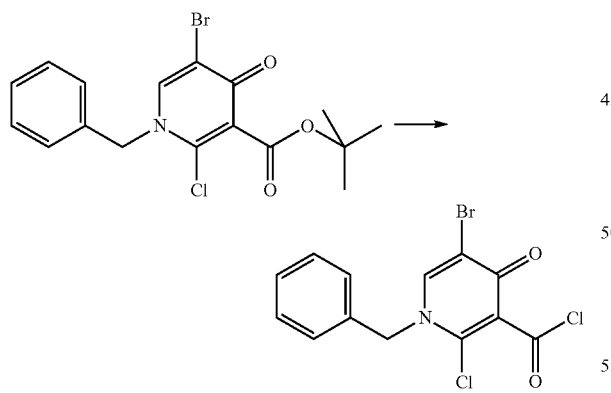

To the compound (610 mg) obtained in step 9-2 was added trifluoroacetic acid (180 ml) under ice-cooling, and the mixture was stirred at room temperature for 2 hr. The reaction mixture was diluted with chloroform (6 ml) and concentrated under reduced pressure. Chloroform (6 ml) was added again to the residue, thionyl chloride (0.18 ml) and N,N-dimethylformamide (one drop) were added, and the mixture was heated at 70° C. for 30 min. The obtained solution was concentrated under reduced pressure to give the compound described in the above-mentioned scheme (540 mg, 98%).

Step 9-4

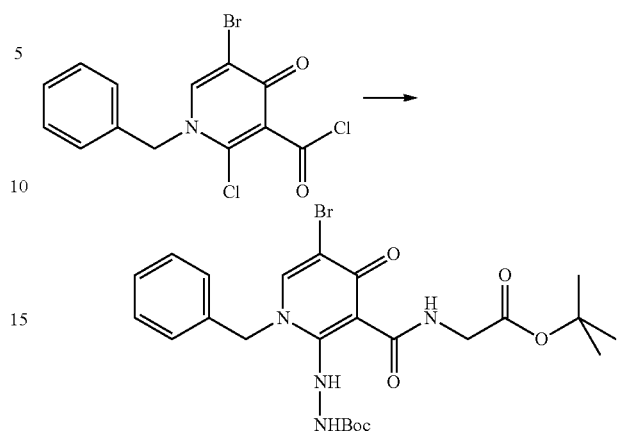

To a solution of the compound (540 mg) obtained in step 9-3 in tetrahydrofuran (6 ml) were added under ice-cooling diisopropylethylamine (0.29 ml) and glycine tert-butyl ester (0.21 ml), and the mixture was stirred for 2 hr. To the reaction mixture were added diisopropylethylamine (0.29 ml) and tert-butyl carbazate, and the mixture was heated at 70° C. for 3 hr. The reaction mixture was concentrated under reduced pressure, and the residue was purified by column chromatography (eluent: hexane/ethyl acetate=3/1-3/2) to give the compound described in the above-mentioned scheme (790 mg, 92%).

$^1$H-NMR (CDCl$_3$) δ: 1.30 (9H, s), 1.48 (9H, s), 4.05 (2H, d, J=5.5 Hz), 5.24 (2H, s), 6.27 (1H, s), 7.14 (2H, t, J=4.1 Hz), 7.34-7.41 (3H, m), 7.47 (1H, s), 11.50 (1H, t, J=5.4 Hz), 11.83 (1H, s).

Step 9-5

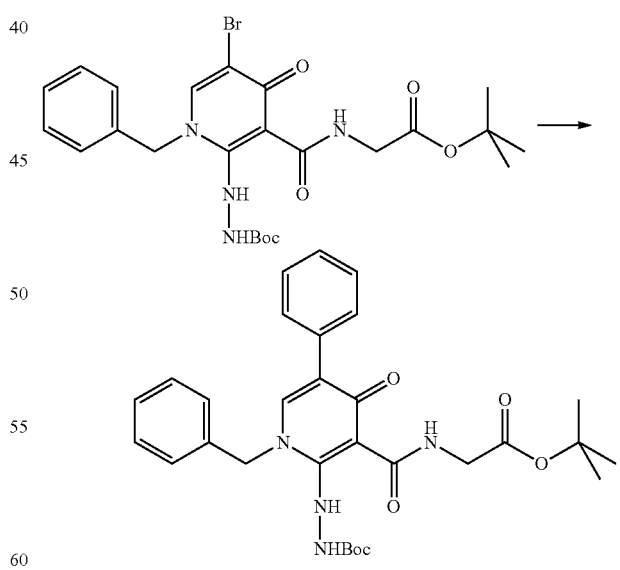

In the same manner as in Example 1, step 1-8, the compound described in the above-mentioned scheme (280 g, 84%) was obtained from the compound (330 mg) obtained in step 9-4.

$^1$H-NMR (CDCl$_3$) δ: 1.31 (9H, s), 1.48 (9H, s), 4.06 (2H, d, J=5.5 Hz), 5.30 (2H, s), 6.16 (1H, s), 7.17 (2H, d, J=7.4 Hz), 7.18 (1H, s), 7.28-7.40 (6H, m), 7.43-7.46 (2H, m), 11.79 (1H, s), 11.85 (1H, t, J=5.4 Hz).
Step 9-6

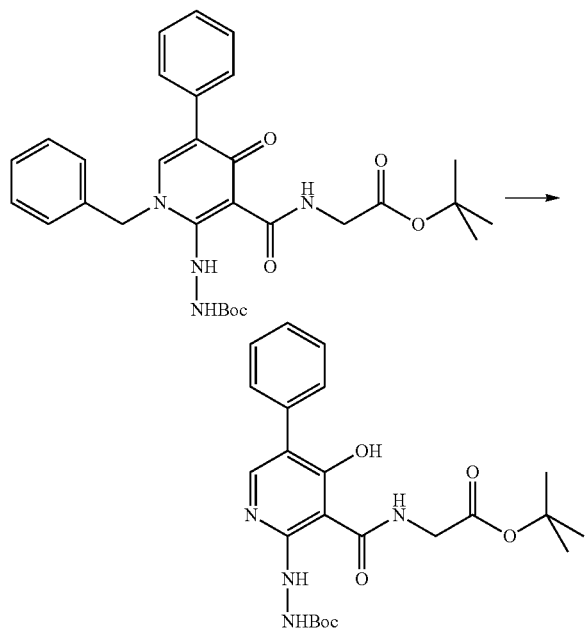

In the same manner as in Example 2, step 2-5, the compound described in the above-mentioned scheme (86 mg, 87%) was obtained from the compound (120 mg) obtained in step 9-5.

$^1$H-NMR (CDCl$_3$) δ: 1.45 (9H, s), 1.49 (9H, s), 4.15 (2H, s), 7.06-7.29 (8H, m), 10.40 (1H, s), 10.95 (1H, s).
Step 9-7

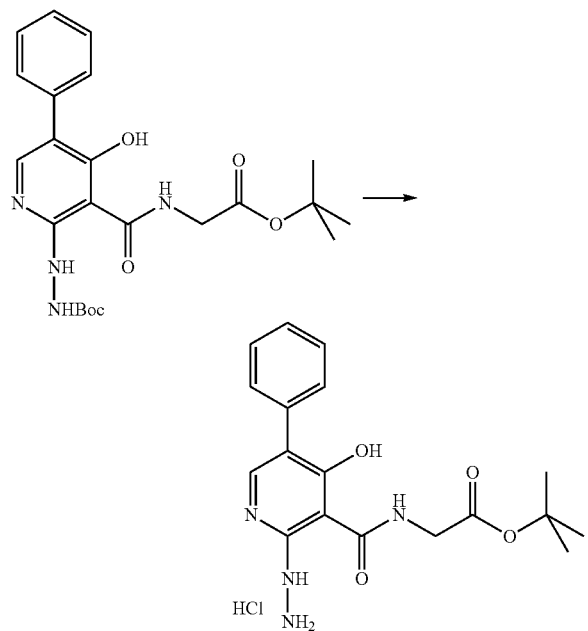

To a solution of the compound (110 mg) obtained in step 9-6 in chloroform (0.3 ml) was added 4N hydrochloric acid dioxane solution (1 ml), and the mixture was stirred under ice-cooling for 2 hr. The reaction mixture was concentrated under reduced pressure to give the compound described in the above-mentioned scheme (84 mg, 87%).

$^1$H-NMR (CD$_3$OD) δ: 1.49 (9H, s), 4.04 (2H, s), 7.36-7.47 (5H, m), 7.57 (1H, s).
Step 9-8

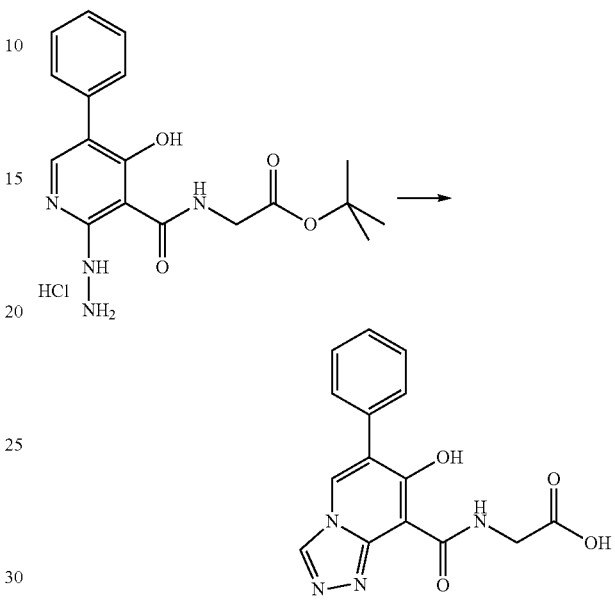

To the compound (41 mg) obtained in step 9-7 was added trimethyl orthoformate (0.41 ml), and the mixture was heated at 100° C. for 30 min. The reaction mixture was concentrated under reduced pressure, and the residue was dissolved in chloroform (1 ml). Trifluoroacetic acid (2 ml) was added and the mixture was stirred at room temperature for 3 hr. The reaction mixture was concentrated under reduced pressure, 4N hydrochloric acid dioxane solution (1 ml) was added, and the mixture was stirred at room temperature for 30 min. The reaction mixture was concentrated under reduced pressure and the residue was slurried in water to give the title compound (29 mg, 89%).

$^1$H-NMR (DMSO-D$_6$) δ: 4.06 (2H, d, J=5.5 Hz), 7.39-7.46 (3H, m), 7.60 (2H, dd, J=8.3, 1.4 Hz), 8.39 (1H, s), 8.86 (1H, s), 10.50 (1H, t, J=5.7 Hz), 12.59 (1H, s), 13.75 (1H, s).

Example 10

Production of [(7-hydroxy[1,2,4]triazolo[4,3-a]pyridine-8-carbonyl)amino]acetic acid hydrochloride Step 10-1

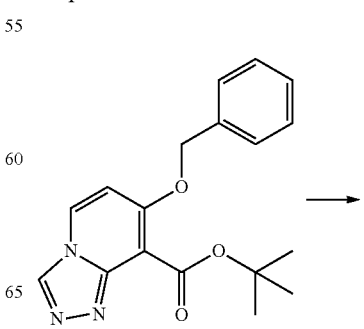

-continued

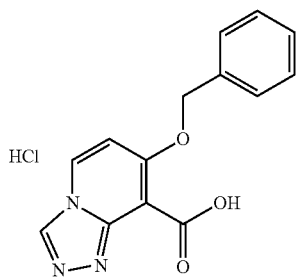

In the same manner as in the deprotection reaction of the carboxyl-protecting group in Example 9, step 9-8, a crude product containing the compound described in the above-mentioned scheme as a main component was obtained from the compound (0.050 g) obtained in Example 1, step 1-5.

$^1$H-NMR (DMSO-D$_6$) δ: 5.60 (s, 2H), 7.35-7.55 (m, 5H), 7.69 (d, 1H, J=7.7 Hz), 9.03 (d, 1H, J=7.7 Hz), 9.48 (s, 1H).

Step 10-2

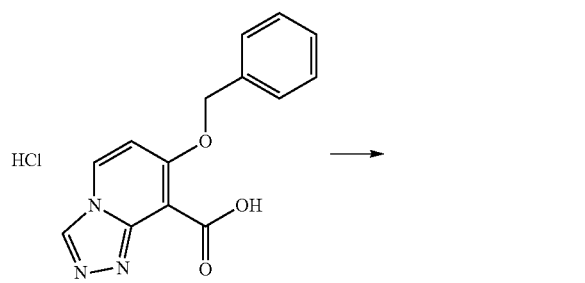

In the same manner as in Example 1, step 1-10, the compound described in the above-mentioned scheme (0.024 g, 41%) was obtained from the compound obtained in step 10-1.

$^1$H-NMR (CDCl$_3$) δ: 1.51 (s, 9H), 4.23 (d, 2H, J=5.6 Hz), 5.35 (s, 2H), 6.81 (d, 1H, J=7.7 Hz), 7.26-7.51 (m, 5H), 8.10 (d, 1H, J=7.7 Hz), 8.67 (s, 1H), 9.66 (br s, 1H).

The compound obtained in this step was subjected to removal of the hydroxyl-protecting group and carboxyl-protecting group in the same manner as above, and the obtained compound was converted to hydrochloride by a conventional method to give the title compound.

$^1$H-NMR (DMSO-D$_6$) δ: 4.07 (s, 2H), 6.65 (d, 1H, J=7.7 Hz), 8.32 (d, 1H, J=7.7 Hz), 8.99 (s, 1H), 10.09 (s, 1H).

Example 11

Production of [(6-hydroxy[1,2,3]triazolo[1,5-a]pyridine-7-carbonyl)amino]acetic acid Step 11-1

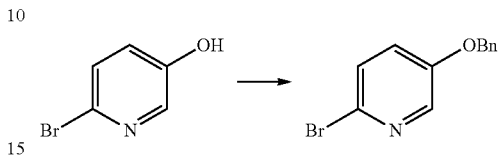

2-Bromo-5-hydroxypyridine (5.8 g), N,N-dimethylformamide (58 ml) and potassium carbonate (5.1 g) were mixed, benzyl bromide (4.4 ml) was added under ice-cooling and the mixture was stirred at room temperature for 13 hr. To the reaction mixture were added ethyl acetate (58 ml) and water (87 ml) and the organic layer was separated from the mixture and washed successively with water (60 ml, 30 ml) twice and with saturated brine (30 ml). The organic layer was dried over anhydrous magnesium sulfate, and filtered. The filtrate was concentrated under reduced pressure. The obtained residue was purified by column chromatography (eluent: hexane/ethyl acetate=10/1-7/1) to give the compound described in the above-mentioned scheme (7.4 g, 83%).

$^1$H-NMR (CDCl$_3$) δ: 5.09 (s, 2H), 7.15 (dd, 1H, J=8.1, 3.2 Hz), 7.33-7.38 (m, 1H), 7.36 (d, 1H, J=8.1 Hz), 7.40-7.41 (m, 4H), 8.13 (d, 1H, J=3.2 Hz).

Step 11-2

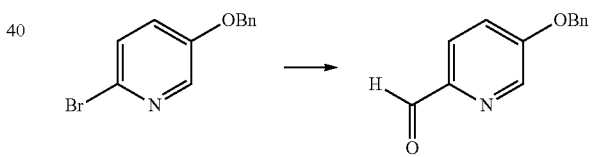

To n-butyllithium (1.54 mol/l hexane solution 25 ml) was added dropwise a solution of the compound (1 g) obtained in step 11-1 in toluene (4 ml) at −78° C. over 7 min. The reaction mixture was stirred at −78° C. for 50 min, and a solution of N,N-dimethylformamide (0.352 ml) in toluene (4 ml) was added dropwise. The reaction mixture was further stirred at −78° C. for 1 hr, water (6 ml) was added at −10° C., and the mixture was stirred at room temperature for 2 hr. The organic layer and the aqueous layer were separated, the aqueous layer was extracted twice with toluene (5 ml). The organic layers were combined and washed with saturated brine (10 ml). The organic layer was dried over anhydrous magnesium sulfate, and the mixture was filtered. The filtrate was concentrated under reduced pressure and the obtained residue was purified by column chromatography (eluent: hexane/ethyl acetate=10/1-7/1) to give the compound described in the above-mentioned scheme (641 mg, 79%).

$^1$H-NMR (CDCl$_3$) δ: 5.21 (s, 2H), 7.35-7.45 (m, 6H), 7.95 (d, 1H, J=8.9 Hz), 8.51 (d, 1H, J=2.8 Hz), 9.99 (s, 1H).

Step 11-3

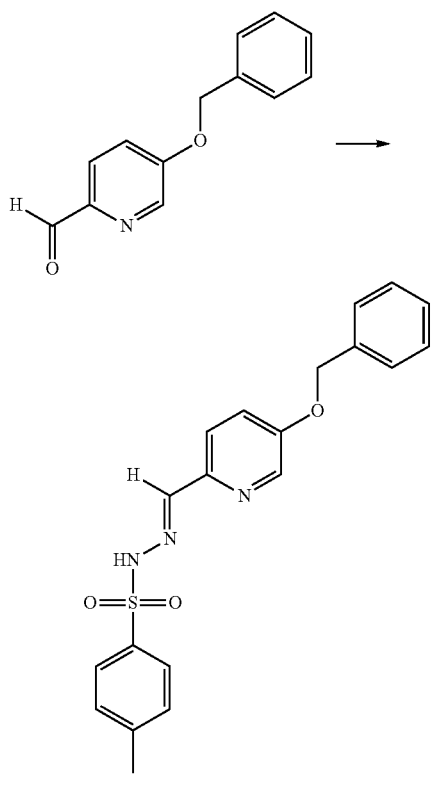

The compound (637 mg) obtained in step 11-2, methanol (6.4 ml) and tosylhydrazide (574 mg) were mixed, and the mixture was heated under reflux for 10 min. The reaction mixture was concentrated under reduced pressure, morpholine (6.4 ml) was added, and the mixture was heated under reflux for 30 min. The reaction mixture was concentrated under reduced pressure, and ethyl acetate (12 ml), 2M aqueous sodium carbonate solution (6 ml) and water (5 ml) were added. Further, tetrahydrofuran (6 ml) was added and the organic layer was separated. The aqueous layer was extracted twice with ethyl acetate (5 ml), and the organic layers were combined and washed with saturated brine (10 ml). The organic layer was dried over anhydrous magnesium sulfate, and filtered. The filtrate was concentrated under reduced pressure and the obtained solid was slurried in diisopropyl ether to give the compound described in the above-mentioned scheme (566 mg, 84%).

$^1$H-NMR (CDCl$_3$) δ: 5.12 (s, 2H), 7.11 (dd, 1H, J=9.7, 2.0 Hz), 7.36-7.47 (m, 5H), 7.61 (dd, 1H, J=9.7, 0.8 Hz), 7.99 (d, 1H, J=0.8 Hz), 8.34 (d, 1H, J=2.0 Hz).

Step 11-4

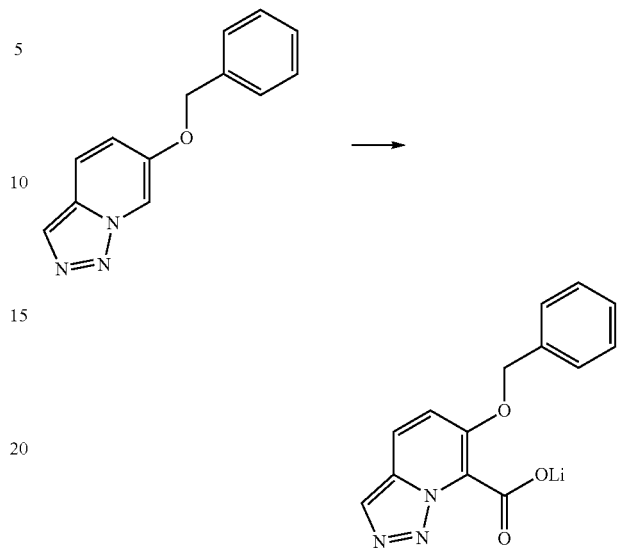

The compound (200 mg) obtained in step 11-3 and tetrahydrofuran (2 ml) were mixed, and lithium diisopropylamide (2M tetrahydrofuran, heptane, ethylbenzene solution, 0.45 ml) was added at −40° C. After stirring at −40° C. for 1 hr, dry ice was added, and the mixture was allowed to warm to room temperature by stirring for 1 hr. Thereafter, methanol (2 ml) was added, and the reaction mixture was concentrated under reduced pressure to give the compound described in the above-mentioned scheme as a crude product. This was directly used for the next step.

Step 11-5

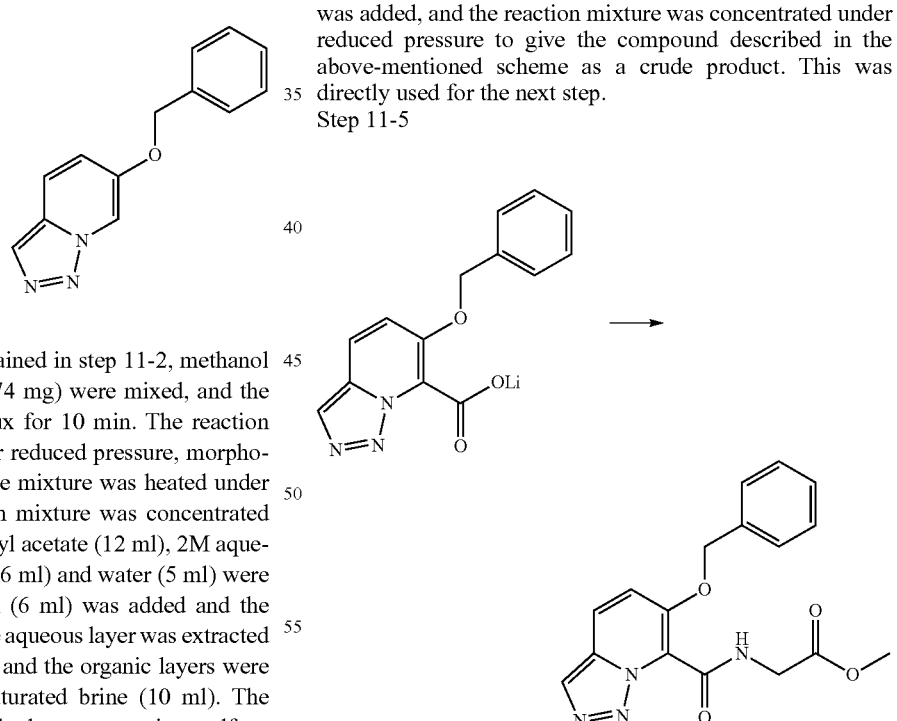

In the same manner as in Example 1, step 1-10, the compound described in the above-mentioned scheme (85 mg, 28% (2 step)) was obtained from the crude product obtained in step 11-4. $^1$H-NMR (CDCl$_3$) δ: 3.80 (s, 3H), 4.38 (d, 2H, J=5.2 Hz), 5.32 (s, 2H), 7.24 (d, 1H, J=9.7 Hz), 7.31-7.41 (m, 3H), 7.46-7.49 (m, 2H), 7.75 (d, 1H, J=9.7 Hz), 8.11 (s, 1H), 8.79 (br s, 1H).

Step 11-6

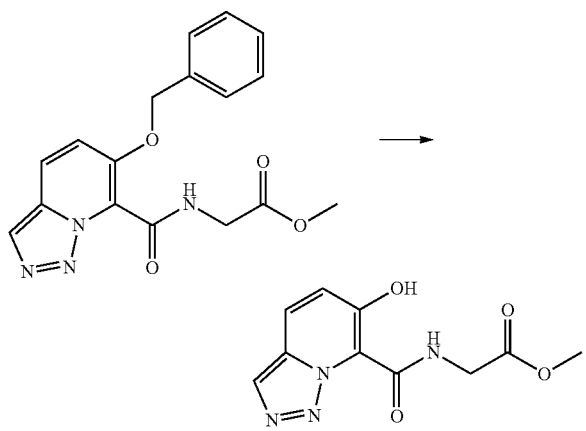

In the same manner as in Example 2, step 2-5, the compound described in the above-mentioned scheme (40 mg, 76%) was obtained from the compound (72 mg) obtained in step 11-5.

$^1$H-NMR (CDCl$_3$) δ: 3.83 (s, 3H), 4.37 (d, 2H, J=6.0 Hz), 7.17 (d, 1H, J=9.7 Hz), 7.80 (d, 1H, J=9.7 Hz), 8.12 (s, 1H), 10.57 (br s, 1H), 13.56 (s, 1H).

The compound obtained in this step was subjected to removal of the carboxyl group in the same manner as above to give the title compound.

$^1$H-NMR (DMSO-D$_6$) δ: 4.28 (d, 2H, J=5.2 Hz), 7.31 (d, 1H, J=9.7 Hz), 8.20 (d, 1H, J=9.7 Hz), 8.39 (s, 1H), 10.36 (t, 1H, J=5.2 Hz), 13.82 (s, 1H).

Example 116

Production of [(7-hydroxy-5-phenethyl[1,2,4]triazolo[1,5-a]pyridine-8-carbonyl)amino]acetic acid Step 116-1

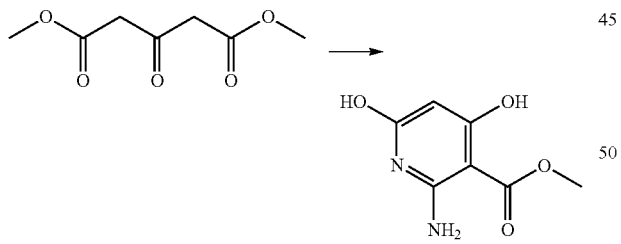

Cyanamide (1.4 g) and 1,4-dioxane (20 ml) were mixed, and dimethyl 1,3-acetonedicarboxylate (2.0 g) and nickel(II) acetylacetonate (0.30 g) were added. The mixture was heated under reflux for 16 hr. The mixture was cooled to room temperature, stirred for 1 hr and the resulting solid was collected by filtration. To the obtained solid was added methanol (6.0 ml) and the mixture was stirred at room temperature for 1.5 hr. The solid was collected by filtration to give the compound described in the above-mentioned scheme (1.4 g, 64%).

$^1$H-NMR (DMSO-D$_6$) δ: 3.80 (s, 3H), 4.92 (s, 1H), 7.20 (s, 2H), 10.29 (s, 1H), 11.51 (s, 1H).

Step 116-2

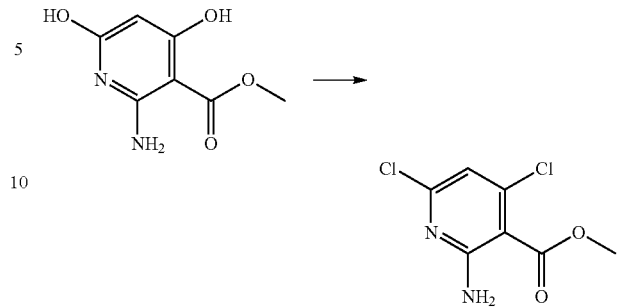

The compound (30 g) obtained in step 116-1, phosphorus oxychloride (150 ml) and N,N-diisopropylethylamine (30 ml) were mixed, and the mixture was stirred at room temperature for 3 days. The reaction mixture was concentrated, and azeotropically distilled 3 times with toluene. Under ice-cooling, methanol (30 ml) and water (150 ml) were added and the mixture was stirred at room temperature for 1 hr. The resulting solid was collected by filtration, and combined with the solid resulting from the filtrate. Methanol (50 ml) was added and the mixture was stirred at room temperature for 1 hr. The solid was collected by filtration to give primary crystals. The filtrate was concentrated, and methanol (10 ml) was added to the residue, and the resulting solid was collected by filtration to give a secondary crystal. The primary crystal and the secondary crystal were combined to give the compound described in the above-mentioned scheme (21 g, 59%).

$^1$H-NMR (DMSO-D$_6$) δ: 3.84 (s, 3H), 6.84 (s, 1H), 7.16 (br s, 2H).

Step 116-3

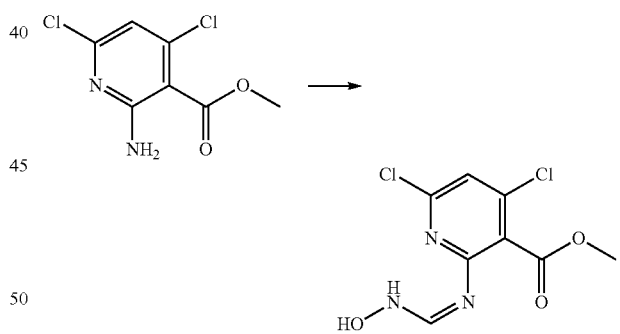

The compound (2.2 g) obtained in step 116-2 and 2-propanol (31 ml) were mixed, and N,N-dimethylformamide dimethyl acetal (2.9 ml) was added. The mixture was heated under reflux for 30 min. The reaction mixture was cooled to room temperature, hydroxylamine hydrochloride (1.4 g) was added, and the mixture was stirred at room temperature for 30 min. The reaction mixture was concentrated to an about half amount, and water (40 ml) and 2-propanol (6.6 ml) were added. The mixture was stirred at room temperature for 30 min, and the resulting solid was collected by filtration to give the compound described in the above-mentioned scheme (2.2 g, 84%).

$^1$H-NMR (DMSO-D$_6$) δ: 3.92 (s, 3H), 7.37 (s, 1H), 7.85 (d, 1H, J=9.5 Hz), 10.12 (d, 1H, J=9.5 Hz), 10.83 (s, 1H).

Step 116-4

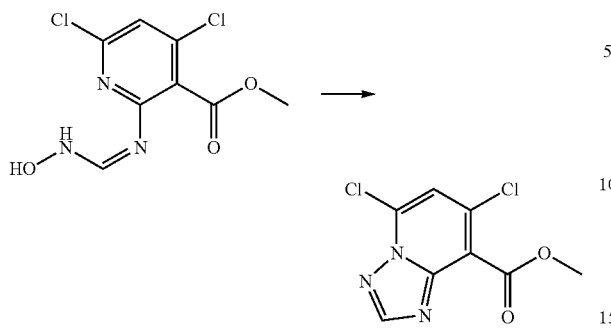

The compound (0.66 g) obtained in step 116-3 and tetrahydrofuran (6.6 ml) were mixed, and trifluoroacetic anhydride (0.37 ml) was added. The mixture was heated under reflux for 22 hr. The reaction mixture was cooled to room temperature, ethyl acetate and saturated aqueous sodium hydrogen carbonate solution were added, and the organic layer was separated. The organic layer was washed with saturated brine, and dried over sodium sulfate. After filtration, the filtrate was concentrated under reduced pressure and the obtained residue was purified by column chromatography (eluent: chloroform/ethyl acetate=4/1) to give the compound described in the above-mentioned scheme (0.32 g, 51%).

$^1$H-NMR (DMSO-D$_6$) δ: 3.99 (s, 3H), 7.92 (s, 1H), 8.71 (s, 1H).

Step 116-5

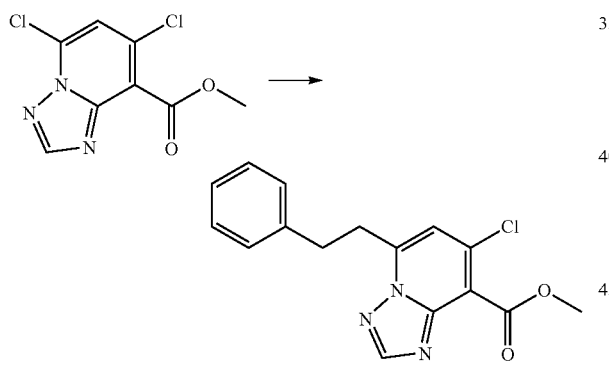

The compound (1.0 g) obtained in step 116-4, phenethylboronic acid (1.2 g), potassium carbonate (1.7 g), [1,1'-bis(diphenylphosphino)ferrocene]palladium(II) dichloride dichloromethane complex (1:1) (0.083 g), cyclopentyl methyl ether (6.0 ml) and water (0.15 ml) were mixed, and the mixture was stirred with heating at 50° C. for 6 hr. The reaction mixture was cooled to room temperature, and the organic layer was washed twice with 3% aqueous diethylenetriamine solution (10 ml) and saturated brine (5 ml). Sodium sulfate and metal scavenger silica gel (1 g) were added and the mixture was stirred at room temperature for 1 hr, and filtered through a Kiriyama funnel packed with silica gel (1 g). The filtrate was concentrated under reduced pressure to give the compound described in the above-mentioned scheme (1.87 g) as a crudely purified product.

$^1$H-NMR (CDCl$_3$) δ: 3.17 (t, 2H, J=7.8 Hz), 3.48 (t, 2H, J=7.8 Hz), 4.08 (s, 3H), 6.84 (s, 1H), 7.18-7.28 (m, 5H), 8.42 (s, 1H).

Step 116-6

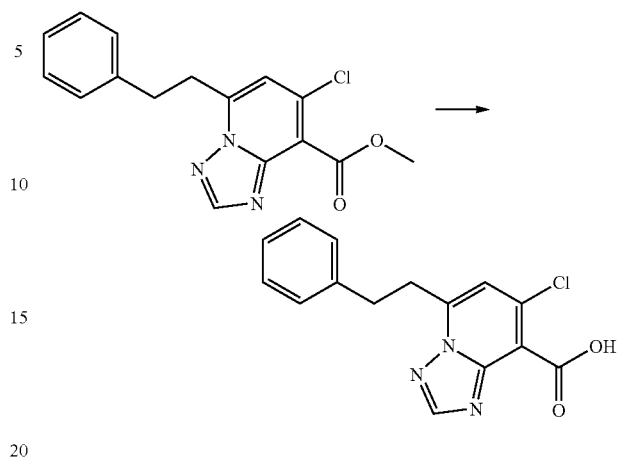

The compound (1.87 g) obtained in step 116-5 and tetrahydrofuran were mixed, and 4N aqueous sodium hydroxide solution (4.0 ml) was added under ice-cooling. After stirring at room temperature for 2 hr, the reaction mixture was neutralized with concentrated hydrochloric acid (1.4 ml) under ice-cooling. To the suspension were added ethanol (5 ml) and water (1.3 ml) and the mixture was stirred for 1 hr. The solid was collected by filtration to give the compound described in the above-mentioned scheme (0.847 g, 69%).

$^1$H-NMR (DMSO-D$_6$) δ: 3.13 (t, 2H, J=7.8 Hz), 3.45 (t, 2H, J=7.8 Hz), 7.23-7.31 (m, 5H), 8.65 (s, 1H), 14.19 (s, 1H).

Step 116-7

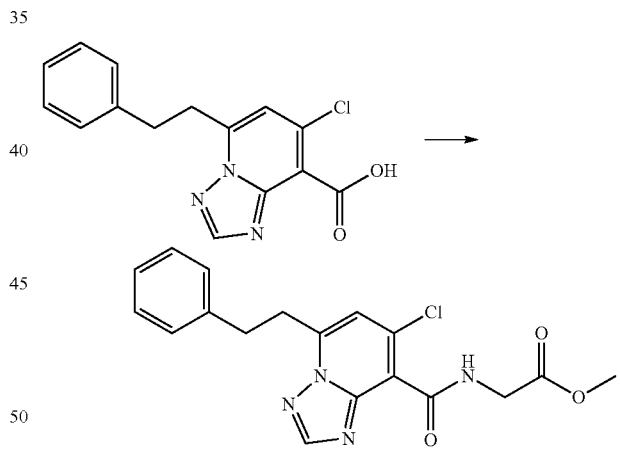

The compound (0.200 g) obtained in step 116-6, acetonitrile (1.0 ml), 1-hydroxybenzotriazole monohydrate (0.122 g) and glycine methyl ester hydrochloride (0.100 g) were mixed, and triethylamine (0.111 ml) and 1-ethyl-3-(3-dimethylaminopropyl)carbodiimide hydrochloride (0.153 g) were added under ice-cooling. The mixture was stirred at room temperature for 2 hr. Saturated aqueous sodium hydrogen carbonate solution (2 ml) was added to the reaction mixture and the precipitated solid was collected by filtration to give the compound described in the above-mentioned scheme (0.194 g, 78%).

$^1$H-NMR (CDCl$_3$) δ: 3.18 (t, 2H, J=7.8 Hz), 3.48 (t, 2H, J=7.8 Hz), 3.81 (s, 3H), 4.34 (d, 2H, J=5.2 Hz), 6.92 (s, 1H), 7.15-7.33 (m, 5H), 8.42 (s, 1H), 9.90 (s, 1H).

Step 116-8

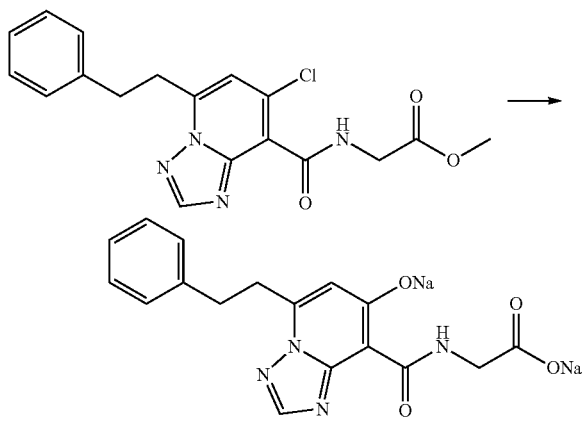

The compound (0.150 g) obtained in step 116-7, 2-ethoxyethanol (0.75 ml) and 8N aqueous sodium hydroxide solution (0.23 ml) were mixed and the mixture was stirred at 90° C. for 18 hr. To this mixture were added ethanol (0.75 ml) and water (0.23 ml) and the mixture was stirred at room temperature for 1 hr. The solid was collected by filtration to give a crudely purified product of the compound described in the above-mentioned scheme (0.19 g).

$^1$H-NMR (DMSO-D$_6$) δ: 2.99-3.11 (m, 4H), 3.58 (d, 2H, J=4.4 Hz), 6.01 (s, 1H), 7.20-7.27 (m, 5H), 7.86 (s, 1H), 11.23 (t, 1H, J=4.4 Hz).

Step 116-9

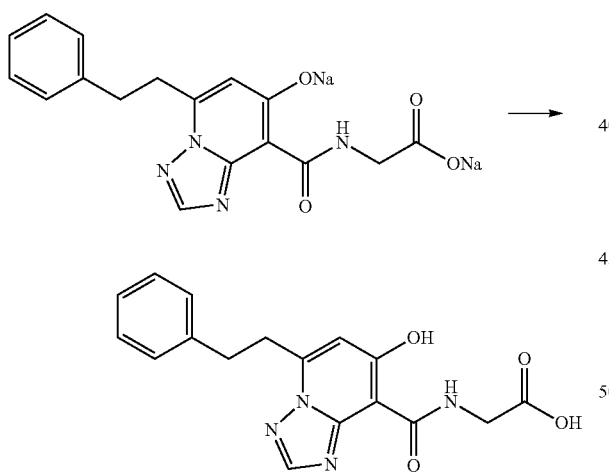

The compound (0.19 g) obtained in step 116-8 and water (0.63 ml) were mixed and the mixture was warmed to 50° C. Acetone (0.78 ml) and 6N hydrochloric acid (0.2 ml) were added, and the mixture was stirred at the same temperature for 1 hr. After stirring under ice-cooling for 1 hr, the solid was collected by filtration to give the compound described in the above-mentioned scheme (0.11 g, 80%).

$^1$H-NMR (DMSO-D$_6$) δ: 3.12 (t, 2H, J=7.9 Hz), 3.40 (t, 3H, J=7.9 Hz), 4.22 (d, 2H, J=5.2 Hz), 6.79 (s, 1H), 7.21-7.29 (m, 5H), 8.58 (s, 1H), 9.84 (t, 1H, J=5.2 Hz), 12.97 (s, 1H), 14.22 (s, 1H).

Step 116-10

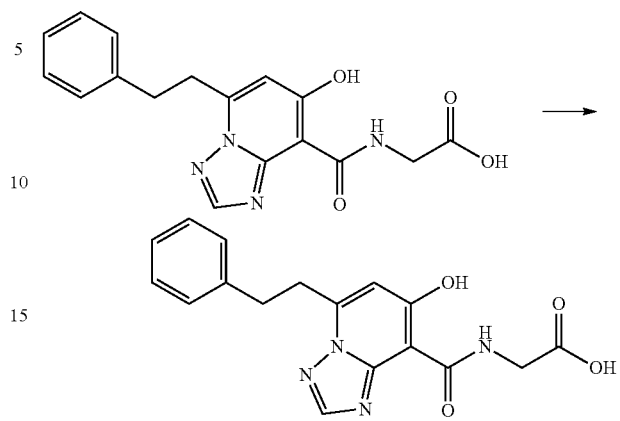

The compound (0.050 g) obtained in step 116-9 and methanol (3 ml) were mixed and the mixture was heated to 60° C. The solution was cooled to room temperature and stirred for one day. The solid was collected by filtration to give the title compound (0.031 g, 61%).

$^1$H-NMR (DMSO-D$_6$) δ: 3.12 (t, 2H, J=7.9 Hz), 3.40 (t, 3H, J=7.9 Hz), 4.22 (d, 2H, J=5.2 Hz), 6.79 (s, 1H), 7.21-7.29 (m, 5H), 8.58 (s, 1H), 9.84 (t, 1H, J=5.2 Hz), 12.97 (s, 1H), 14.22 (s, 1H).

Example 117

Production of [(5-butyl-7-hydroxy[1,2,4]triazolo[1,5-a]pyridine-8-carbonyl)amino]acetic acid Step 117-1

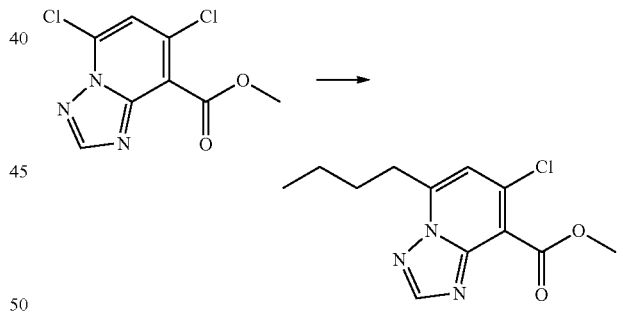

The compound (0.050 g) obtained in step 116-4, butylboronic acid (0.042 g), silver(I) oxide (0.071 g), potassium carbonate (0.084 g), [1,1'-bis(diphenylphosphino)ferrocene] palladium(II) dichloride dichloromethane complex (1:1) (0.008 g) and tetrahydrofuran (1.0 ml) were mixed, and the mixture was heated under reflux for 10 hr. Insoluble material was filtered off through celite, and saturated aqueous sodium hydrogen carbonate solution and ethyl acetate were added. The organic layer was separated from the mixture. The organic layer was washed twice with saturated aqueous sodium hydrogen carbonate solution and saturated brine, dried over sodium sulfate and filtered. The filtrate was concentrated under reduced pressure and the obtained residue was purified by thin layer chromatography (eluent: hexane/ethyl acetate=1/1) to give the compound described in the above-mentioned scheme (0.046 g, 77%).

$^1$H-NMR (CDCl$_3$) δ: 1.00 (t, 3H, J=7.4 Hz), 1.45-1.53 (m, 2H), 1.79-1.87 (m, 2H), 3.18 (t, 2H, J=7.9 Hz), 4.08 (s, 3H), 6.92 (s, 1H), 8.38 (s, 1H).

Step 117-2

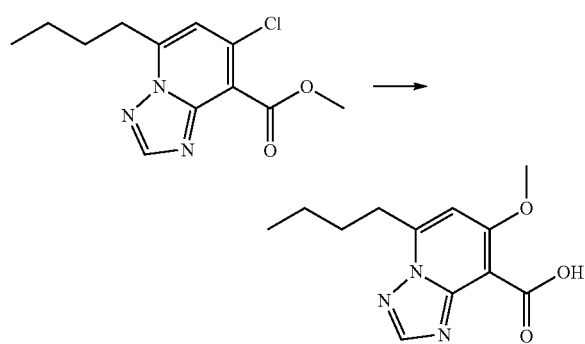

The compound (0.043 g) obtained in step 117-1 and methanol (0.22 ml) were mixed, and 28% sodium methoxide methanol solution (0.014 ml) was added. The mixture was stirred at room temperature for 4 hr. Water (0.22 ml) was added, and the mixture was stirred at room temperature for 1 hr. 1N Hydrochloric acid (0.16 ml) was added to the reaction mixture, and the resulting solid was collected by filtration to give the compound described in the above-mentioned scheme (0.026 g, 66%).

$^1$H-NMR (CDCl$_3$) δ: 1.01 (t, 3H, J=7.3 Hz), 1.46-1.57 (m, 2H), 1.82-1.90 (m, 2H), 3.21 (t, 2H, J=7.9 Hz), 4.15 (s, 3H), 6.77 (s, 1H), 8.28 (s, 1H).

Step 117-3

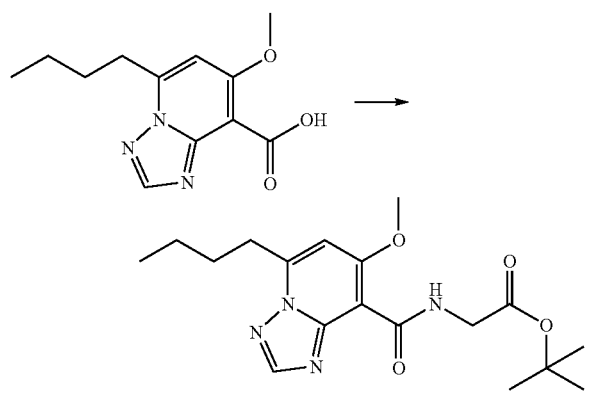

The compound (0.025 g) obtained in step 117-2 and N,N-dimethylformamide (0.50 ml) were mixed, and 1-hydroxybenzotriazole monohydrate (0.016 g) and glycine tert-butyl-lester (0.015 ml) and 1-ethyl-3-(3-dimethylaminopropyl) carbodiimide hydrochloride (0.020 g) were added. The mixture was stirred at room temperature for 1.5 hr. Under ice-cooling, 5% aqueous sodium hydrogen carbonate solution and water were added to the reaction mixture and the resulting solid was collected by filtration to give the compound described in the above-mentioned scheme (0.033 g, 94%).

$^1$H-NMR (CDCl$_3$) δ: 1.00 (t, 4H, J=7.3 Hz), 1.51 (s, 9H), 1.80-1.90 (m, 2H), 3.18 (t, 2H, J=7.9 Hz), 4.21 (d, 2H, J=5.2 Hz), 6.72 (s, 1H), 8.29 (s, 1H), 9.72 (t, 1H, J=4.2 Hz).

Step 117-4

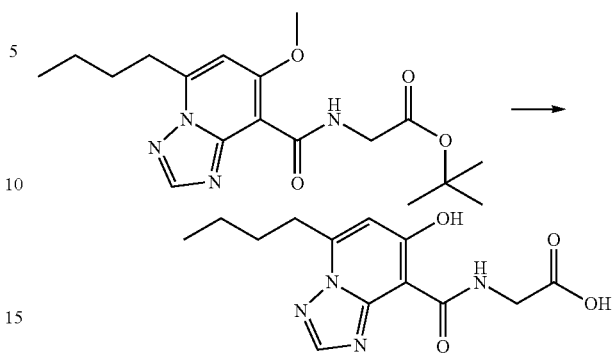

The compound (0.030 g) obtained in step 117-3 and 25% hydrogen bromide acetic acid solution (0.60 ml) were mixed, and the mixture was heated under reflux for 3 hr. The reaction mixture was concentrated under reduced pressure. To the obtained residue were added water (0.60 ml) and 4N aqueous sodium hydroxide solution (0.23 ml) under ice-cooling. Then, 2N hydrochloric acid (0.23 ml) was added under ice-cooling, and the resulting solid was collected by filtration to give the compound described in the above-mentioned scheme (0.010 g, 42%).

$^1$H-NMR (DMSO-D$_6$) δ: 0.93 (t, 3H, J=7.5 Hz), 1.33-1.44 (m, 2H), 1.71-1.80 (m, 2H), 3.10 (t, 2H, J=7.5 Hz), 4.20 (d, 2H, J=5.2 Hz), 6.85 (s, 1H), 8.55 (s, 1H), 9.84 (br s, 1H), 14.26 (br s, 1H).

Step 117-5

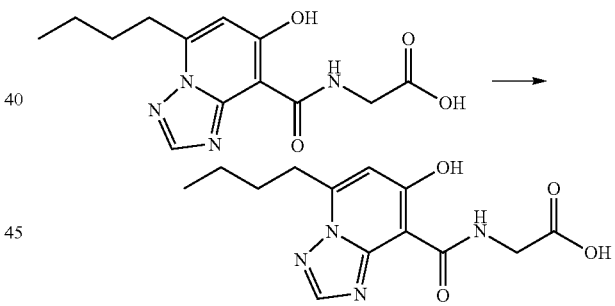

The compound (0.100 g) obtained in step 117-4 and methyl ethyl ketone (1.0 ml) were mixed, and heated to 80° C. Heptane (1.0 ml) was added to the solution, and the mixture was stirred at room temperature overnight. The solid was collected by filtration to give the title compound (0.089 g, 89%).

$^1$H-NMR (DMSO-D$_6$) δ: 0.93 (t, 3H, J=7.5 Hz), 1.33-1.44 (m, 2H), 1.71-1.80 (m, 2H), 3.10 (t, 2H, J=7.5 Hz), 4.20 (d, 2H, J=5.2 Hz), 6.85 (s, 1H), 8.55 (s, 1H), 9.84 (br s, 1H), 14.26 (br s, 1H).

In the same manner as in the above-mentioned Examples 1 to 11, Example 116 or 117, or other conventional methods as necessary, the compounds of Examples 12 to 115 and Examples 118 to 122 shown in the following Tables 3 to 24 were produced.

The structural formulas and property data of the compounds of Examples 1 to 122 are shown in the following Tables 1 to 24.

TABLE 1

| Ex. No. | compound name | structural formula | ¹H-NMR, δppm | MS (M + H) | Ms (M − H) |
|---|---|---|---|---|---|
| 1 | {[5-(4-fluoro-3-trifluoromethylphenyl)-7-hydroxy[1,2,4]triazolo[1,5-a]pyridine-8-carbonyl]amino} acetic acid hydrochloride | | ¹H-NMR (DMSO-D₆, 400 MHz) δ: 4.25 (d, 2H, J = 5.6 Hz), 7.31 (s, 1H), 7.73-7.82 (m, 1H), 8.34-8.43 (m, 1H), 8.43-8.51 (m, 1H), 8.61 (s, 1H), 9.99 (t, 1H, J = 5.6 Hz). | 399 | 397 |
| 2 | [(7-hydroxy-5-phenethyl[1,2,4]triazolo[1,5-a]pyridine-8-carbonyl)amino]acetic acid hydrochloride | | ¹H-NMR (DMSO-D₆, 400 MHz,) δ: 3.12 (t, 2H, J = 7.8 Hz), 3.41 (t, 2H, J = 7.8 Hz), 4.21 (d, 2H, J = 5.6 Hz), 6.81 (s, 1H), 7.14-7.33 (m, 5H), 8.60 (s, 1H), 9.85 (t, 1H, J = 5.6 Hz). | 341 | 339 |
| 3 | [(5-butyl-7-hydroxy[1,2,4]triazolo[1,5-a]pyridine-8-carbonyl)amino]acetic acid hydrochloride | | ¹H-NMR (DMSO-D₆, 400 MHz) δ: 0.93 (t, 3H, J = 7.4 Hz), 1.39 (td, 2H, J = 14.8, 7.4 Hz), 1.72-1.79 (m, 2H), 3.10 (t, 2H, J = 7.7 Hz), 4.21 (d, 2H, J = 5.5 Hz), 6.85 (s, 1H), 8.56 (s, 1H), 9.84 (t, 1H, J = 5.6 Hz). | 293 | 291 |
| 4 | [(5,6-diethyl-7-hydroxy[1,2,4]triazolo[1,5-a]pyridine-8-carbonyl)amino]acetic acid hydrochloride | | ¹H-NMR (DMSO-D₆, 400 MHz) δ: 1.15 (t, 3H, J = 7.5 Hz), 1.29 (t, 3H, J = 7.5 Hz), 2.72 (q, 2H, J = 7.5 Hz), 3.20 (q, 2H, J = 7.6 Hz), 4.21 (d, 2H, J = 5.6 Hz), 8.52 (s, 1H), 9.95 (t, 1H, J = 5.6 Hz). | 293 | 291 |
| 5 | [(7-hydroxy-6-phenethyl[1,2,4]triazolo[1,5-a]pyridine-8-carbonyl)amino]acetic acid hydrochloride | | ¹H-NMR (DMSO-D₆, 400 MHz) δ: 2.93 (s, 4H), 4.22 (d, 2H, J = 5.7 Hz), 7.19 (tt, 1H, J = 7.1, 1.8 Hz), 7.23-7.31 (m, 4H), 8.50 (s, 1H), 8.78 (s, 1H), 9.97 (s, 1H). | 341 | 339 |

TABLE 2

| Ex. No. | compound name | structural formula | $^1$H-NMR, δ ppm | MS (M + H) | MS (M − H) |
|---|---|---|---|---|---|
| 6 | [(5-butyl-6-chloro-7-hydroxy[1,2,4]triazolo[1,5-a]pyridine-8-carbonyl)amino]acetic acid hydrochloride | 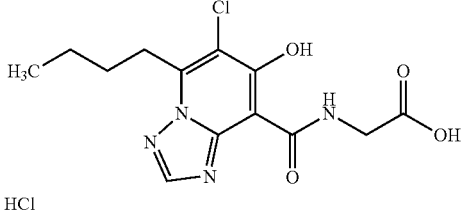 | $^1$H-NMR (DMSO-d$_6$, 400 MHz) δ: 0.93 (t, 3H, J = 7.3 Hz), 1.36-1.47 (m, 2H), 1.64-1.72 (m, 2H), 3.15-3.28 (m, 2H), 4.15 (d, 2H, J = 2.8 Hz), 8.74 (br s, 1H), 10.20 (br s, 1H). | 327 | 325 |
| 7 | [(7-hydroxy-2-methyl-5-phenethyl[1,2,4]triazolo[1,5-a]pyridine-8-carbonyl)amino]acetic acid hydrochloride | 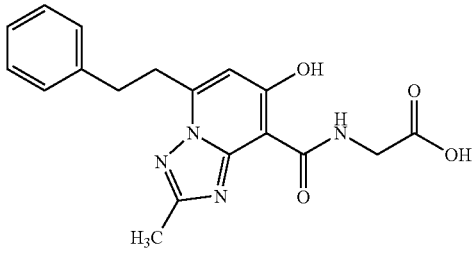 | $^1$H-NMR (DMSO-D$_6$, 400 MHz) δ: 2.52 (s, 3H), 3.10 (t, 2H, J = 7.8 Hz), 3.35 (t, 2H, J = 7.8 Hz), 4.19 (d, 2H, J = 5.7 Hz), 6.69 (s, 1H), 7.18-7.31 (m, 5H), 9.81 (t, 1H, J = 5.5 Hz). | 355 | 353 |
| 8 | {[8-[(3,3-dimethylbutyl)-6-hydroxy[1,2,4]triazolo[1,5-a]pyridine-5-carbonyl]amino}acetic acid hydrochloride | 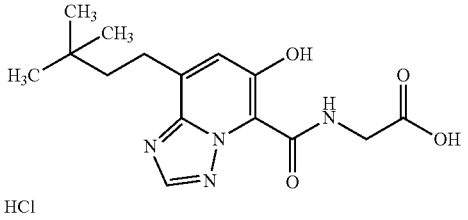 | $^1$H-NMR (DMSO-D$_6$, 400 MHz) δ: 0.98 (s, 9H), 1.57-1.66 (m, 2H), 2.89-2.99 (m, 2H), 4.25 (d, 2H, J = 5.4 Hz), 7.42 (s, 1H), 8.64 (s, 1H), 10.42 (t, 1H, J = 5.4 Hz), 13.28 (s, 1H). | 321 | 319 |
| 9 | [(7-hydroxy-6-phenyl[1,2,4]triazolo[4,3-a]pyridine-8-carbonyl)amino]acetic acid | 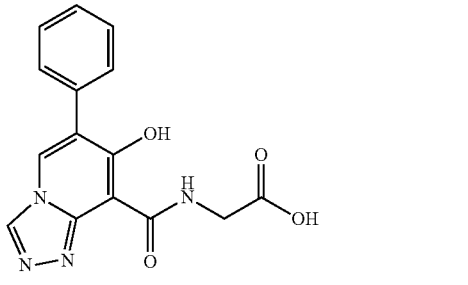 | $^1$H-NMR (DMSO-D$_6$, 400 MHz) δ: 4.06 (d, 2H, J = 5.5 Hz), 7.39-7.46 (m, 3H), 7.60 (dd, 2H, J = 8.3, 1.4 Hz), 8.39 (s, 1H), 8.86 (s, 1H), 10.50 (t, 1H, J = 5.7 Hz), 12.59 (s, 1H), 13.75 (s, 1H). | 313 | 311 |
| 10 | [(7-hydroxy[1,2,4]triazolo[4,3-a]pyridine-8-carbonyl)amino]acetic acid hydrochloride | 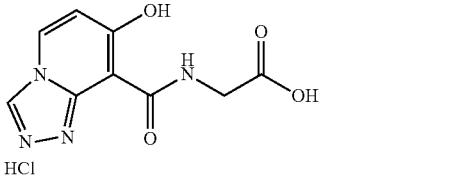 | $^1$H-NMR (DMSO-D$_6$, 400 MHz) δ: 4.07 (s, 2H), 6.65 (d, 1H, J = 7.7 Hz), 8.32 (d, 1H, J = 7.7 Hz), 8.99 (s, 1H), 10.09 (s, 1H). | 237 | 235 |
| 11 | [(6-hydroxy[1,2,3]triazolo[1,5-a]pyridine-7-carbonyl)amino]acetic acid | 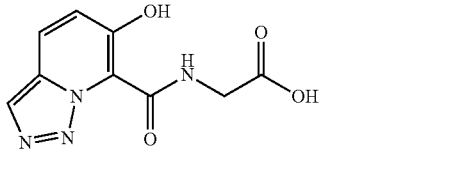 | $^1$H-NMR (DMSO-D$_6$, 400 MHz) δ: 4.28 (d, 2H, J = 5.2 Hz), 7.31 (d, 1H, J = 9.7 Hz), 8.20 (d, 1H, J = 9.7 Hz), 8.39 (s, 1H), 10.36 (t, 1H, J = 5.2 Hz), 13.82 (s, 1H). | 237 | 235 |

TABLE 3

| Ex. No. | compound name | structural formula | ¹H-NMR, δ ppm | MS (M + H) | MS (M − H) |
|---|---|---|---|---|---|
| 12 | [(7-hydroxy[1,2,4]triazolo[1,5-a]pyridine-8-carbonyl)amino]acetic acid hydrochloride | | ¹H-NMR (DMSO-D₆, 400 MHz) δ: 4.22 (d, 2H, J = 5.6 Hz), 6.93 (d, 1H, J = 7.7 Hz), 8.56 (s, 1H), 8.96 (d, 1H, J = 7.7 Hz), 9.81-9.91 (m, 1H). | 237 | 235 |
| 13 | [(7-hydroxy-2-phenyl[1,2,4]triazolo[1,5-a]pyridine-8-carbonyl)amino]acetic acid hydrochloride | | ¹H-NMR (DMSO-D₆, 400 MHz) δ: 4.27 (d, 2H, J = 5.6 Hz), 6.94 (d, 1H, J = 7.7 Hz), 7.55-7.58 (m, 3H), 8.31-8.33 (m, 2H), 9.00 (d, 1H, J = 7.3 Hz), 10.11 (t, 1H, J = 5.2 Hz). | 313 | 311 |
| 14 | ({5-[2-(4-chlorophenyl)ethyl]-7-hydroxy[1,2,4]triazolo[1,5-a]pyridine-8-carbonyl}amino)acetic acid hydrochloride | | ¹H-NMR (DMSO-D₆, 400 MHz) δ: 3.12 (2H, t, J = 7.9 Hz), 3.40 (2H, t, J = 7.7 Hz), 4.21 (2H, d, J = 5.6 Hz), 6.80 (1H, s), 7.27 (2H, d, J = 8.5 Hz), 7.35 (2H, d, J = 8.5 Hz), 8.59 (1H, s), 9.85 (1H, t, J = 5.6 Hz). | 375 | 373 |
| 15 | [(2-cyclopropyl-7-hydroxy-5-phenethyl[1,2,4]triazolo[1,5-a]pyridine-8-carbonyl)amino]acetic acid hydrochloride | | ¹H-NMR (DMSO-D₆, 400 MHz) δ: 1.04-1.12 (m, 4H), 2.17-2.23 (m, 1H), 3.10 (t, 2H, J = 7.9 Hz), 3.29-3.37 (m, 2H), 4.18 (d, 2H, J = 5.3 Hz), 6.66 (s, 1H), 7.18-7.32 (m, 5H), 9.84 (t, 1H, J = 4.9 Hz), 14.10 (s, 1H). | 381 | 379 |
| 16 | ({7-hydroxy-5-[2-(4-trifluoromethylphenyl)ethyl][1,2,4-]triazolo[1,5-a]pyridine-8-carbonyl}amino)acetic acid hydrochloride | | ¹H-NMR (DMSO-D₆, 400 MHz) δ: 3.21 (2H, t, J = 7.8 Hz), 3.44 (2H, t, J = 7.8 Hz), 4.20 (2H, d, J = 5.8 Hz), 6.83 (1H, s), 7.48 (2H, d, J = 8.1 Hz), 7.66 (2H, d, J = 8.1 Hz), 8.59 (1H, s), 9.81-9.88 (1H, m). | 409 | 407 |

TABLE 3-continued

| Ex. No. | compound name | structural formula | $^1$H-NMR, δ ppm | MS (M + H) | MS (M − H) |
|---|---|---|---|---|---|
| 17 | ({5-[2-(4-fluorophenyl)ethyl]-7-hydroxy[1,2,4]triazolo[1,5-a]pyridine-8-carbonyl}amino)acetic acid hydrochloride | 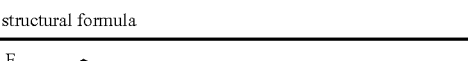 | $^1$H-NMR (DMSO-D$_6$, 400 MHz) δ: 3.11 (2H, t, J = 7.9 Hz), 3.39 (2H, t, J = 7.7 Hz), 4.21 (2H, d, J = 5.2 Hz), 6.80 (1H, s), 7.07-7.16 (2H, m), 7.23-7.30 (2H, m), 8.60 (1H, s), 9.85 (1H, t, J = 5.4 Hz). | 359 | 357 |

TABLE 4

| Ex. No. | compound name | structural formula | $^1$H-NMR, δ ppm | MS (M + H) | MS (M − H) |
|---|---|---|---|---|---|
| 18 | {[7-hydroxy-5-(3-methylbutyl)[1,2,4]triazolo[1,5-a]pyridine-8-carbonyl]amino}acetic acid hydrochloride | | $^1$H-NMR (DMSO-D$_6$, 400 MHz) δ: 0.95 (6H, d, J = 6.5 Hz), 1.58-1.70 (3H, m), 3.07-3.13 (2H, m), 4.21 (2H, d, J = 5.6 Hz), 6.87 (1H, s), 8.57 (1H, s), 9.85 (1H, t, J = 5.6 Hz). | 307 | 305 |
| 19 | ({5-[2-(3,5-difluorophenyl)ethyl]-7-hydroxy[1,2,4]triazolo[1,5-a]pyridine-8-carbonyl}amino)acetic acid hydrochloride | | $^1$H-NMR (DMSO-D$_6$, 400 MHz) δ: 3.15 (2H, t, J = 7.8 Hz), 3.42 (2H, t, J = 7.8 Hz), 4.20 (2H, d, J = 5.6 Hz), 6.83 (1H, s), 6.97-7.11 (3H, m), 8.58-8.61 (1H, m), 9.79-9.89 (1H, m). | 377 | 375 |
| 20 | [(5-cyclopentylmethyl-7-hydroxy[1,2,4]triazolo[1,5-a]pyridin-8-carbonyl)amino]acetic acid hydrochloride | | $^1$H-NMR (DMSO-D$_6$, 400 MHz) δ: 1.21-1.32 (2H, m), 1.45-1.55 (2H, m), 1.59-1.74 (4H, m), 2.40-2.49 (1H, m), 3.09 (2H, d, J = 7.3 Hz), 4.21 (2H, d, J = 5.6 Hz), 6.88 (1H, s), 8.55 (1H, s), 9.85 (1H, t, J = 5.6 Hz). | 319 | 317 |
| 21 | {[5-(3,5-difluorophenyl)-7-hydroxy[1,2,4]triazolo[1,5-a]pyridine-8-carbonyl]amino}acetic acid | | $^1$H-NMR (DMSO-D$_6$, 400 MHz) δ: 4.25 (d, 2H, J = 5.8 Hz), 7.29 (s, 1H), 7.56 (tt, 1H, J = 9.3, 2.3 Hz), 7.78-7.86 (m, 2H), 8.62 (s, 1H), 9.99 (t, 1H, J = 5.8 Hz). | 349 | 347 |

TABLE 4-continued

| Ex. No. | compound name | structural formula | $^1$H-NMR, δ ppm | MS (M + H) | MS (M − H) |
|---|---|---|---|---|---|
| 22 | [(7-hydroxy-5-phenyl[1,2,4]triazolo[1,5-a]pyridine-8-carbonyl)amino]acetic acid hydrochloride | | $^1$H-NMR (DMSO-D$_6$, 400 MHz) δ: 4.25 (d, 2H, J = 5.6 Hz), 7.12 (s, 1H), 7.59-7.62 (m, 3H), 7.99-8.02 (m, 2H), 8.58 (s, 1H), 9.98 (t, 1H, J = 5.6 Hz). | 313 | 311 |
| 23 | {[5-(3-chloro-4-fluorophenyl)-7-hydroxy[1,2,4]triazolo[1,5-a]pyridine-8-carbonyl]amino}acetic acid hydrochloride | | $^1$H-NMR (DMSO-D$_6$, 400 MHz) δ: 4.25 (s, 2H, J = 5.6 Hz), 7.23 (s, 1H), 7.67 (dd, 1H, J = 8.9, 8.9 Hz), 8.05 (ddd, 1H, J = 8.9, 2.4, 8.8 Hz), 8.30 (dd, 1H, J = 7.3, 2.4 Hz), 8.60 (s, 1H), 9.98 (t, 1H, J = 5.4 Hz). | 365 | 363 |

TABLE 5

| Ex. No. | compound name | structural formula | $^1$H-NMR, δ ppm | MS (M + H) | MS (M − H) |
|---|---|---|---|---|---|
| 24 | {[5-(3,3-dimethylbutyl)-7-hydroxy[1,2,4]triazolo[1,5-a]pyridine-8-carbonyl]amino}acetic acid hydrochloride | | $^1$H-NMR (DMSO-D$_6$, 400 MHz) δ: 0.98 (s, 9H), 1.59-1.70 (m, 2H), 3.01-3.13 (m, 2H), 4.21 (d, 2H, J = 5.6 Hz), 6.89 (s, 1H), 8.57 (s, 1H), 9.84 (t, 1H, J = 5.6 Hz). | 321 | 319 |
| 25 | {[5-(3,4-difluorophenyl)-7-hydroxy[1,2,4]triazolo[1,5-a]pyridine-8-carbonyl]amino}acetic acid hydrochloride | | $^1$H-NMR (DMSO-D$_6$, 400 MHz) δ: 4.25 (d, 2H, J = 5.5 Hz), 7.22 (s, 1H), 7.69 (dt, 1H, J = 15.0, 5.3 Hz), 7.92-7.94 (m, 1H), 8.17 (ddd, 1H, J = 11.9, 7.7, 2.2 Hz), 8.60 (s, 1H), 9.98 (t, 1H, J = 5.5 Hz). | 349 | 347 |
| 26 | {[7-hydroxy-5-(p-tolyl)[1,2,4]triazolo[1,5-a]pyridine-8-carbonyl]amino}acetic acid hydrochloride | | $^1$H-NMR (DMSO-D$_6$, 400 MHz) δ: 2.42 (s, 3H), 4.24 (d, 2H, J = 5.5 Hz), 7.09 (s, 1H), 7.40 (d, 2H, J = 8.2 Hz), 7.93 (d, 2H, J = 8.2 Hz), 8.58 (s, 1H), 9.97 (t, 1H, J = 5.5 Hz). | 327 | 325 |

TABLE 5-continued

| Ex. No. | compound name | structural formula | ¹H-NMR, δ ppm | MS (M + H) | MS (M − H) |
|---|---|---|---|---|---|
| 27 | [(5-cyclohexyl-7-hydroxy[1,2,4]triazolo[1,5-a]pyridine-8-carbonyl)amino]acetic acid hydrochloride | | ¹H-NMR (DMSO-$D_6$, 400 MHz) δ: 1.21-1.62 (5H, m), 1.69-1.79 (1H, m), 1.80-1.88 (2H, m), 1.98-2.09 (2H, m), 3.31-3.43 (1H, m), 4.20 (2H, d, J = 5.8 Hz), 6.76 (1H, s), 8.56 (1H, s), 9.80-9.87 (1H, m). | 319 | 317 |
| 28 | [(5-cyclohexylmethyl-7-hydroxy[1,2,4]triazolo[1,5-a]pyridine-8-carbonyl)amino]acetic acid hydrochloride | | ¹H-NMR (DMSO-$D_6$, 400 MHz) δ: 0.98-1.23 (5H, m), 1.56-1.70 (5H, m), 1.90-1.99 (1H, m), 3.00 (2H, d, J = 7.2 Hz), 4.21 (2H, d, J = 5.6 Hz), 6.84 (1H, s), 8.55 (1H, s), 9.85 (1H, t, J = 5.6 Hz). | 333 | 331 |

TABLE 6

| Ex. No. | compound name | structural formula | ¹H-NMR, δ ppm | MS (M + H) | MS (M − H) |
|---|---|---|---|---|---|
| 29 | {[7-hydroxy-5-(3-phenylpropyl)[1,2,4]triazolo[1,5-a]pyridine-8-carbonyl]amino}acetic acid | | ¹H-NMR (DMSO-$D_6$, 400 MHz) δ: 2.07-2.15 (m, 2H), 2.71 (t, 2H, J = 7.7 Hz), 3.12 (t, 2H, J = 7.6 Hz), 4.21 (d, 2H, J = 5.5 Hz), 6.85 (s, 1H), 7.15-7.31 (m, 5H), 8.55 (s, 1H), 9.84 (t, 1H, J = 5.5 Hz). | 355 | 353 |
| 30 | [(5-cyclopentyl-7-hydroxy[1,2,4]triazolo[1,5-a]pyridine-8-carbonyl)amino]acetic acid hydrochloride | | ¹H-NMR (DMSO-$D_6$, 400 MHz) δ: 1.68-1.84 (m, 6H), 2.14-2.21 (m, 2H), 3.69-3.76 (m, 1H), 4.21 (d, 2H, J = 5.7 Hz), 6.83 (s, 1H), 8.56 (s, 1H), 9.85 (t, 1H, J = 5.6 Hz). | 305 | 303 |
| 31 | {[5-(3-fluoro-5-trifluoromethyl-phenyl)-7-hydroxy[1,2,4]triazolo[1,5-a]pyridine-8-carbonyl]amino}acetic acid hydrochloride | | ¹H-NMR (DMSO-$D_6$, 400 MHz) δ: 4.25 (d, 2H, J = 5.6 Hz), 7.37 (s, 1H), 7.99 (d, 1H, J = 9.3 Hz), 8.23 (d, 1H, J = 9.3 Hz), 8.30 (s, 1H), 8.63 (s, 1H), 10.00 (t, 1H, J = 5.6 Hz). | 399 | 397 |

TABLE 6-continued

| Ex. No. | compound name | structural formula | $^1$H-NMR, δ ppm | MS (M + H) | MS (M − H) |
|---|---|---|---|---|---|
| 32 | {[5-(4-fluorophenyl)-7-hydroxy[1,2,4]triazolo[1,5-a]pyridine-8-carbonyl]ammino} acetic acid hydrochloride | 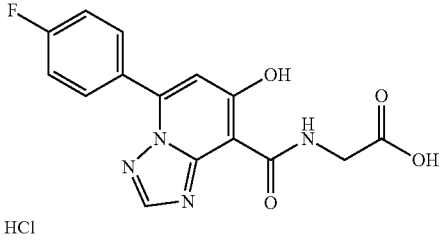 | $^1$H-NMR (DMSO-D$_6$, 400 MHz) δ: 4.24 (d, 2H, J = 5.7 Hz), 7.14 (s, 1H), 7.41-7.48 (m, 2H), 8.07-8.13 (m, 2H), 8.59 (s, 1H), 9.97 (t, 1H, J = 5.7 Hz). | 331 | 329 |
| 33 | {[7-hydroxy-5-(3-trifluoromethyl-phhenyl)[1,2,4]triazolo[1,5-a]pyridine-8-carbonyl]ammino} acetic acid hydrochloride | 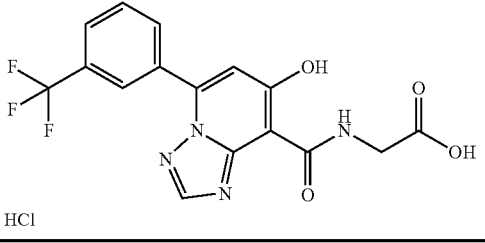 | $^1$H-NMR (DMSO-D$_6$, 400 MHz) δ: 4.25 (d, 2H, J = 5.5 Hz), 7.28 (s, 1H), 7.84 (t, 1H, J = 7.9 Hz), 7.98 (d, 1H, J = 7.9 Hz), 8.28 (d, 1H, J = 7.9 Hz), 8.41 (s, 1H), 8.61 (s, 1H), 10.00 (t, 1H, J = 5.7 Hz). | 381 | 379 |

TABLE 7

| Ex. No. | compound name | structural formula | $^1$H-NMR, δ ppm | MS (M + H) | MS (M − H) |
|---|---|---|---|---|---|
| 34 | {[5-(2-fluoro-5-trifluoromethyl-phenyl)-7-hydroxy[1,2,4]triazolo[1,5-a]pyridine-8-carbonyl]amino} acetic acid hydrochloride | 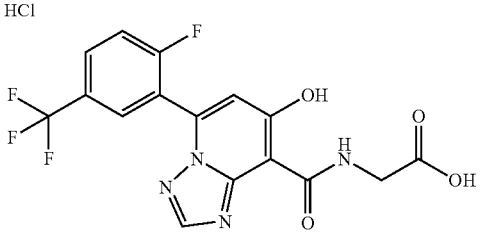 | $^1$H-NMR (DMSO-D$_6$, 400 MHz) δ: 4.25 (d, 2H, J = 5.6 Hz), 7.28 (s, 1H), 7.73 (dd, 1H, J = 9.1, 9.1 Hz), 8.10 (ddd, 1H, J = 9.1, 4.5, 2.0 Hz), 8.24 (dd, 1H, J = 6.4, 2.0 Hz), 8.57 (s, 1H), 9.95 (t, 1H, J = 5.6 Hz). | 399 | 397 |
| 35 | [(7-hydroxy-5-isopropyl[1,2,4]triazolo[1,5-a]pyridine-8-carbonyl)amino] acetic acid hydrochloride | 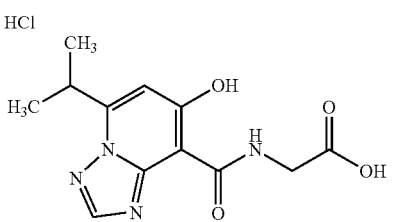 | $^1$H-NMR (DMSO-D$_6$, 400 MHz) δ: 1.37 (d, 6H, J = 7.3 Hz), 3.67 (sept, 1H, J = 7.3 Hz), 4.21 (d, 2H, J = 5.6 Hz), 6.82 (s, 1H), 8.59 (s, 1H), 9.84 (t, 1H, J = 5.6 Hz). | 279 | 277 |
| 36 | {[5-(3-chloro-5-trifluoromethyl-phenyl)-7-hydroxy[1,2,4]triazolo[1,5-a]pyridine-8-carbonyl]amino} acetic acid hydrochloride | 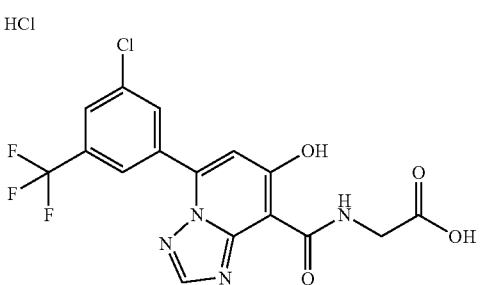 | $^1$H-NMR (DMSO-D$_6$, 400 MHz) δ: 4.25 (d, 2H, J = 5.6 Hz), 7.37 (s, 1H), 8.14 (s, 1H), 8.37 (s, 1H), 8.41 (s, 1H), 8.62 (s, 1H), 9.99 (t, 1H, J = 5.6 Hz). | 415 | 413 |

TABLE 7-continued

| Ex. No. | compound name | structural formula | $^1$H-NMR, δ ppm | MS (M + H) | MS (M − H) |
|---|---|---|---|---|---|
| 37 | {[5-(3-cyanophenyl)-7-hydroxy[1,2,4]triazolo[1,5-a]pyridine-8-carbonyl]amino}acetic acid hydrochloride | 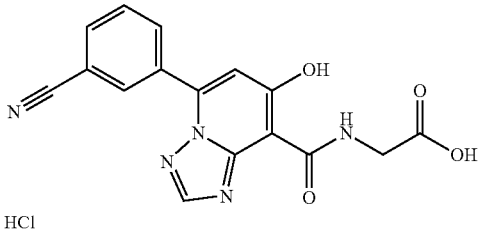 | $^1$H-NMR (DMSO-D$_6$, 400 MHz) δ: 4.25 (d, 2H, J = 5.7 Hz), 7.28 (s, 1H), 7.81 (t, 1H, J = 7.9 Hz), 8.08 (dt, 1H, J = 7.9, 1.0 Hz), 8.34 (d, 1H, J = 8.4 Hz), 8.48 (t, 1H, J = 1.3 Hz), 8.61 (s, 1H), 9.99 (t, 1H, J = 5.7 Hz). | 338 | 336 |
| 38 | ({5-[2-(4-cyclopropyl-phenyl)ethyl]-7-hydroxy[1,2,4]trizazolo[1,5-a]pyridine-8-carbonyl}amino)acetic acid hydrochloride | 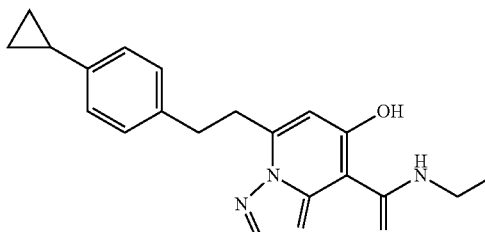 | $^1$H-NMR (DMSO-D$_6$, 400 MHz) δ: 0.59-0.64 (m, 2H), 0.88-0.93 (m, 2H), 1.83-1.90 (m, 1H), 3.06 (t, 2H, J = 7.9 Hz), 3.37 (t, 2H, J = 7.9 Hz), 4.21 (d, 2H, J = 5.6 Hz), 6.81 (s, 1H), 6.99 (d, 2H, J = 8.1 Hz), 7.11 (d, 2H, J = 8.1 Hz), 8.60 (s, 1H), 9.84 (t, 1H, J = 5.6 Hz). | 381 | 379 |

TABLE 8

| Ex. No. | compound name | structural formula | $^1$H-NMR, δ ppm | MS (M + H) | MS (M − H) |
|---|---|---|---|---|---|
| 39 | {[5-(2,2-dimethylpropyl)-7-hydroxy[1,2,4]triazolo[1,5-a]pyridine-8-carbonyl]amino}acetic acid hydrochloride | 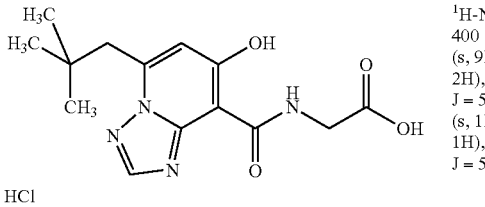 | $^1$H-NMR (DMSO-D$_6$, 400 MHz) δ: 0.97 (s, 9H), 3.12 (s, 2H), 4.21 (d, 2H, J = 5.6 Hz), 6.78 (s, 1H), 8.53 (s, 1H), 9.88 (t, 1H, J = 5.6 Hz). | 307 | 305 |
| 40 | {[5-(1-ethylpropyl)-7-hydroxy[1,2,4]triazolo[1,5-a]pyridine-8-carbonyl]amino}acetic acid hydrochloride | 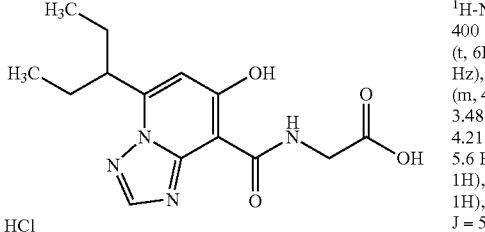 | $^1$H-NMR (DMSO-D$_6$, 400 MHz) δ: 0.78 (t, 6H, J = 7.3 Hz), 1.72-1.94 (m, 4H), 3.37-3.48 (m, 1H), 4.21 (d, 2H, J = 5.6 Hz), 6.85 (s, 1H), 8.55 (s, 1H), 9.88 (t, 1H, J = 5.6 Hz). | 307 | 305 |
| 41 | {[5-(3-chloro-5-fluorophenyl)-7-hydroxy[1,2,4]triazolo[1,5-a]pyridine-8-carbonyl]amino}acetic acid hydrochloride | 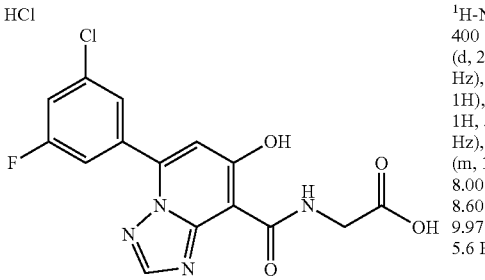 | $^1$H-NMR (DMSO-D$_6$, 400 MHz) δ: 4.24 (d, 2H, J = 5.8 Hz), 7.28 (s, 1H), 7.73 (dt, 1H, J =8.7, 2.1 Hz), 7.88-7.91 (m, 1H), 7.98-8.00 (m, 1H), 8.60 (s, 1H), 9.97 (t, 1H, J = 5.6 Hz). | 365 | 363 |

TABLE 8-continued

| Ex. No. | compound name | structural formula | ¹H-NMR, δ ppm | MS (M + H) | MS (M − H) |
|---|---|---|---|---|---|
| 42 | {[5-(3-fluorophenyl)-7-hydroxy[1,2,4]triazolo[1,5-a]pyridine-8-carbonyl]amino} acetic acid hydrochloride | | ¹H-NMR (DMSO-D$_6$, 400 MHz) δ: 4.25 (d, 2H, J = 5.5 Hz), 7.21 (s, 1H), 7.47 (tdd, 1H, J = 8.6, 2.6, 0.7 Hz), 7.64 (td, 1H, J = 8.1, 6.0 Hz), 7.87 (dt, 1H, J = 7.8, 1.0 Hz), 7.90 (dt, 1H, J = 10.1, 2.1 Hz), 8.60 (s, 1H), 9.99 (t, 1H, J = 5.4 Hz). | 331 | 329 |
| 43 | [(7-hydroxy-5-isobutyl[1,2,4]triazolo[1,5-a]pyridine-8-carbonyl)amino] acetic acid | | ¹H-NMR (DMSO-D$_6$, 400 MHz) δ: 0.94 (d, 6H, J = 6.9 Hz), 2.28 (sept, 1H, J = 6.9, 7.3 Hz), 2.98 (d, 2H, J = 7.3 Hz), 4.21 (d, 2H, J = 5.6 Hz), 6.85 (s, 1H), 8.55 (s, 1H), 9.85 (t, 1H, J = 5.6 Hz). | 293 | 291 |
| 44 | {[5-(3-chlorophenyl)-7-hydroxy[1,2,4]triazolo[1,5-a]pyridine-8-carbonyl]amino} acetic acid | | ¹H-NMR (DMSO-D$_6$, 400 MHz) δ: 4.25 (d, 2H, J = 5.6 Hz), 7.22 (s, 1H), 7.59-7.71 (m, 2H), 7.96 (d, 1H, J = 7.7 Hz), 8.11 (s, 1H), 8.59 (s, 1H), 9.98 (br s, 1H), 12.99 (br s, 1H), 14.38 (br s, 1H). | 347, 349 | 345, 347 |

TABLE 9

| Ex. No. | compound name | structural formula | ¹H-NMR, δ ppm | MS (M + H) | MS (M − H) |
|---|---|---|---|---|---|
| 45 | {[5-(2-ethylbutyl)-7-hydroxy[1,2,4]triazolo[1,5-a]pyridine-8-carbonyl]amino} acetic acid hydrochloride | | ¹H-NMR (DMSO-D$_6$, 400 MHz) δ: 0.85 (t, 6H, J = 7.4 Hz), 1.25-1.39 (m, 4H), 1.94-2.02 (m, 1H), 3.03 (d, 2H, J = 7.3 Hz), 4.21 (d, 2H, J = 5.5 Hz), 6.87 (s, 1H), 8.56 (s, 1H), 9.85 (t, 1H, J = 5.5 Hz). | 321 | 319 |
| 46 | {[5-(3,5-dichlorophenyl)-7-hydroxy[1,2,4]triazolo[1,5-a]pyridine-8-carbonyl]amino} acetic acid hydrochloride | | ¹H-NMR (DMSO-D$_6$, 400 MHz) δ: 4.25 (d, 3H, J = 5.6 Hz), 7.30 (s, 1H), 7.89 (t, 1H, J = 3.5 Hz), 8.08 (s, 1H), 8.09 (s, 1H), 8.61 (s, 1H), 9.99 (t, 1H, J = 5.6 Hz). | 381, 383 | 379, 381 |

TABLE 9-continued

| Ex. No. | compound name | structural formula | ¹H-NMR, δ ppm | MS (M + H) | MS (M − H) |
|---|---|---|---|---|---|
| 47 | {[5-(2-cyclopropylethyl)-7-hydroxy[1,2,4]triazolo[1,5-a]pyridine-8-carbonyl]amino}acetic acid hydrochloride | 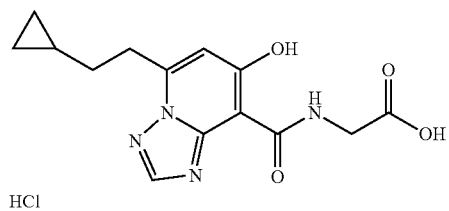 | ¹H-NMR (DMSO-D₆, 400 MHz) δ: 0.00-0.05 (2H, m), 0.35-0.42 (2H, m), 0.72-0.81 (1H, m), 1.64-1.73 (2H, m), 3.15-3.21 (2H, m), 4.20 (2H, d, J = 5.6 Hz), 6.86 (1H, s), 8.55 (1H, s), 9.79-9.87 (1H, m). | 305 | 303 |
| 48 | {[5-(3,3-dimethylphenyl)-7-hydroxy[1,2,4]triazolo[1,5-a]pyridine-8-carbonyl]amino}acetic acid hydrochloride | 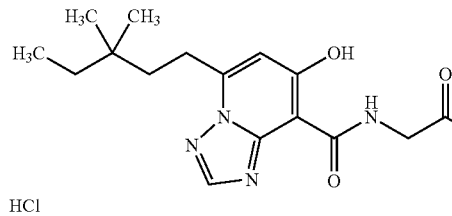 | ¹H-NMR (CD₃OD, 400 MHz) δ: 0.91 (t, 3H, J = 7.6 Hz), 0.98 (s, 6H), 1.39 (q, 2H, J = 7.5 Hz), 1.70 (ddd, 2H, J = 8.7, 4.7, 3.8 Hz), 3.08-3.14 (m, 2H), 4.24 (s, 2H), 6.82 (s, 1H), 8.54 (s, 1H). | 335 | 333 |
| 49 | {[7-hydroxy-5-(3,4,5-trifluorophenyl)[1,2,4]triazolo[1,5-a]pyridine-8-carbonyl]amino}acetic acid hydrochloride | 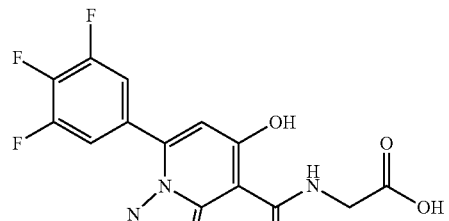 | ¹H-NMR (DMSO-D₆, 400 MHz) δ: 4.25 (d, 2H, J = 5.5 Hz), 7.28 (s, 1H), 8.09 (dd, 2H, J = 9.0, 6.8 Hz), 8.62 (s, 1H), 9.98 (t, 1H, J = 5.1 Hz). | 367 | 365 |
| 50 | {[5-(4-chlorophenyl)-7-hydroxy[1,2,4]triazolo[1,5-a]pyridine-8-carbonyl]amino}acetic acid hydrochloride | 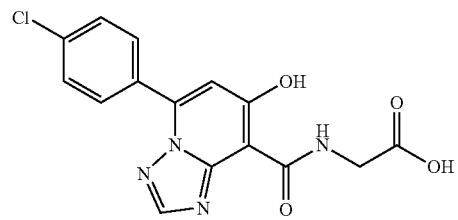 | ¹H-NMR (DMSO-D₆, 400 MHz) δ: 4.25 (d, 2H, J = 5.6 Hz), 7.17 (s, 1H), 7.67 (d, 2H, J = 8.6 Hz), 8.05 (d, 2H, J = 8.6 Hz), 8.59 (s, 1H), 9.98 (t, 1H, J = 5.6 Hz). | 347 | 345 |

TABLE 10

| Ex. No. | compound name | structural formula | ¹H-NMR, δ ppm | MS (M + H) | MS (M − H) |
|---|---|---|---|---|---|
| 51 | [(7-hydroxy-5-(m-tolyl)[1,2,4]triazolo[1,5-a]pyridine-8-carbonyl)amino]acetic acid hydrochloride | 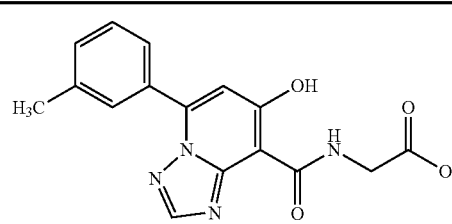 | ¹H-NMR (DMSO-D₆, 400 MHz) δ: 2.42 (3H, s), 4.24 (2H, d, J = 5.6 Hz), 7.09 (1H, s), 7.47-7.51 (2H, m), 7.78-7.84 (2H, m), 8.58 (1H, s), 9.98 (1H, t, J = 5.6 Hz). | 327 | 325 |

TABLE 10-continued

| Ex. No. | compound name | structural formula | $^1$H-NMR, δ ppm | MS (M + H) | MS (M − H) |
|---|---|---|---|---|---|
| 52 | {[5-(3-cyclopropyl-5-fluorophenyl)-7-hydroxy[1,2,4]triazolo[1,5-a]pyridine-8-carbonyl]amino} acetic acid hydrochloride | HCl | $^1$H-NMR (DMSO-D$_6$, 400 MHz) δ: 0.82-0.86 (m, 2H), 1.01-1.06 (m, 2H), 2.03-2.10 (m, 1H), 4.24 (d, 2H, J = 5.6 Hz), 7.15-7.18 (m, 1H), 7.20 (s, 1H), 7.56 (dd, 1H, J = 1.4, 1.4 Hz), 7.62-7.65 (m, 1H), 8.59 (s, 1H), 9.98 (t, 1H, J = 5.6 Hz). | 371 | 369 |
| 53 | [(5-cyclobutylmethyl-7-hydroxy[1,2,4]triazolo[1,5-a]pyridine-8-carbonyl)amino] acetic acid hydrochloride | HCl | $^1$H-NMR (DMSO-D$_6$, 400 MHz) δ: 1.72-1.90 (m, 4H), 1.98-2.10 (m, 2H), 2.80-2.92 (m, 1H), 3.20 (d, 2H, J = 7.4 Hz), 4.20 (d, 2H, J = 5.6 Hz), 6.79 (s, 1H), 8.55 (s, 1H), 9.83 (t, 1H, J = 5.6 Hz). | 305 | 303 |
| 54 | {[5-(2-cyclobutylethyl)-7-hydroxy[1,2,4]triazolo[1,5-a]pyridine-8-carbonyl]amino} acetic acid hydrochloride | HCl | $^1$H-NMR (DMSO-D$_6$, 400 MHz) δ: 1.54-1.67 (m, 2H), 1.72-1.92 (m, 4H), 1.95-2.06 (m, 2H), 2.26-2.37 (m, 1H), 3.00 (t, 2H, J = 7.7 Hz), 4.21 (d, 2H, J = 5.6 Hz), 6.85 (s, 1H), 8.56 (s, 1H), 9.85 (t, 1H, J = 5.6 Hz). | 319 | 317 |
| 55 | {[5-(2-fluoro-3-trifluoromethyl-phenyl)-7-hydroxy[1,2,4]triazolo[1,5-a]pyridine-8-carbonyl]amino} acetic acid hydrochloride | HCl | $^1$H-NMR (DMSO-D$_6$, 400 MHz) δ: 4.24 (2H, d, J = 5.6 Hz), 7.25 (1H, s), 7.61-7.68 (1H, m), 8.03-8.13 (2H, m(), 8.57 (1H, s), 9.87-10.01 (1H, m). | 399 | 397 |

TABLE 11

| Ex. No. | compound name | structural formula | $^1$H-NMR, δ ppm | MS (M + H) | MS (M − H) |
|---|---|---|---|---|---|
| 56 | {[5-(3-chloro-2-fluorophenyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 4.25 (2H, d, J = 5.6 Hz), 7.21 (1H, s), 7.47 (1H, dd, J = 7.9, 3.9 Hz), 7.73 (1H, dd, J = 7.1, 3.5 Hz), 7.88 (1H, dd, J = 7.7, 3.8 Hz), 8.56 (1H, s), 9.95 (1H, t, J = 5.0 Hz). | 365 | 363 |
| 57 | {[7-hydroxy-5-(4-trifluoromethylphenyl)[1,2,4]triazolo[1,5-a]pyridine-8-carbonyl]amino} acetic acid hydrochloride | | $^1$H-NMR (DMSO-D$_6$, 400 MHz) δ: 4.24 (2H, d, J = 5.6 Hz), 7.23 (1H, s), 7.96 (2H, d, J = 8.1 Hz), 8.21 (2H, d, J = 8.1 Hz), 8.59 (1H, s), 9.99 (1H, t, J = 5.3 Hz). | 381 | 379 |
| 58 | [(5-cycloheptyl-7-hydroxy[1,2,4]triazolo[1,5-a]pyridine-8-carbonyl)amino] acetic acid hydrochloride | | $^1$H-NMR (DMSO-D$_6$, 400 MHz) δ: 1.52-1.86 (m, 10H), 1.96-2.04 (m, 2H), 3.50-3.59 (m, 1H), 4.21 (d, 2H, J = 5.5 Hz), 6.78 (s, 1H), 8.56 (s,m 1H), 9.86 (t, 1H, J = 5.5 Hz). | 333 | 331 |
| 59 | {[5-(2,3-difluorophenyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 4.25 (d, 2H, J = 5.7 Hz), 7.20 (s, 1H), 7.45 (tdd, 1H, J = 8.2, 4.9, 1.4 Hz), 7.59 (ddt, 1H, J = 8.3, 5.4, 1.2 Hz), 7.70-7.77 (m, 1H), 8.56 (s, 1H), 9.95 (t, 1H, J = 5.6 Hz). | 349 | 347 |
| 60 | {[5-(2-cyclopentylethyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 1.11-1.19 (m, 2H), 1.47-1.61 (m, 4H), 1.74-1.87 (m, 5H), 3.10 (t, 2H, J = 7.5 Hz), 4.21 (d, 2H, J = 5.6 Hz), 6.87 (s, 1H), 8.56 (s, 1H), 9.84 (t, 1H, J = 5.6 Hz). | 333 | 331 |

TABLE 12

| Ex. No. | compound name | structural formula | $^1$H-NMR, δ ppm | MS (M + H) | MS (M − H) |
|---|---|---|---|---|---|
| 61 | {[5-(2-fluorophenyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 4.25 (d, 2H, J = 5.6 Hz), 7.13 (s, 1H), 7.41-7.48 (m, 2H), 7.66-7.72 (m, 1H), 7.74-7.78 (m, 1H), 8.55 (s, 1H), 9.95 (t, 1H, J = 5.6 Hz). | 331 | 329 |
| 62 | {[5-(4-chloro-2-fluorophenyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 4.25 (d, 2H, J = 5.2 Hz), 7.16 (s, 1H), 7.55 (dd, 1H, J = 8.1, 1.4 Hz), 7.74 (dd, 1H, J = 10.0, 1.4 Hz), 7.81 (dd, 1H, J = 8.1, 8.1 Hz), 8.56 (s, 1H), 9.94 (t, 1H, J = 5.2 Hz). | 365 | 363 |
| 63 | {[5-(4-fluorophenyl)-7-hydroxy[1,2,4]triazolo[1,5-a]pyridine-8-carbonyl]amino} acetic acid hydrochloride | | $^1$H-NMR (DMSO-D$_6$, 400 MHz) δ: 4.20 (2H, d, J = 5.5 Hz), 4.46 (2H, s), 6.74 (1H, s), 7.16 (2H, dd, J = 8.9, 4.5 Hz), 7.45 (2H, dd, J = 8.6, 5.5 Hz), 8.57 (1H, s), 9.83 (1H, t, J = 5.4 Hz). | 345 | 343 |
| 64 | (R)-2-{[5-(3,5-difluorophenyl)-7-hydroxy[1,2,4]triazolo[1,5-a]pyridine-8-carbonyl]amino} propionic acid hydrochloride | | $^1$H-NMR (DMSO-D$_6$, 400 MHz) δ: 1.52 (d, 3H, J = 7.1 Hz), 4.58-4.67 (m, 1H), 7.28 (br s, 1H), 7.51-7.59 (m, 1H), 7.81 (d, 2H, J = 6.4 Hz), 8.62 (s, 1H), 10.08-10.15 (br m, 1H). | 363 | 361 |
| 65 | [(7-hydroxy-5-propyl[1,2,4]triazolo[1,5-a]pyridine-8-carbonyl)amino] acetic acid hydrochloride | | $^1$H-NMR (DMSO-D$_6$, 400 MHz) δ: 0.97 (t, 3H, J = 7.4 Hz), 1.80 (tq, 2H, J = 7.4, 7.4 Hz), 3.07 (t, 2H, J = 7.4 Hz), 4.21 (d, 1H, J = 5.7 Hz), 6.85 (s, 1H), 8.56 (s, 1H), 9.84 (t, 1H, J = 5.7 Hz). | 279 | 277 |

TABLE 13

| Ex. No. | compound name | structural formula | $^1$H-NMR, δ ppm | MS (M + H) | MS (M − H) |
|---|---|---|---|---|---|
| 66 | 2-{[5-(3,5-difluorophenyl)-7-hydroxy-[1,2,4]triazolo[1,5-a]pyridine-8-carbonyl]amino} propionic acid hydrochloride | HCl | $^1$H-NMR (DMSO-D$_6$, 400 MHz) δ: 1,52 (d, 3H, J = 7.1 Hz), 4.58-4.67 (m, 1H), 7.28 (br s, 1H), 7.51-7.59 (m, 1H), 7.81 (d, 2H, J = 6.4 Hz), 8.62 (s, 1H), 10.08-10.15 (br m, 1H). | 363 | 361 |
| 67 | (S)-2-{[5-(3,5-difluorophenyl)-7-hydroxy[1,2,4]triazolo[1,5-a]pyridine-8-carbonyl]amino} propionic acid hydrochloride | HCl | $^1$H-NMR (DMSO-D$_6$, 400 MHz) δ: 1.52 (d, 3H, J = 7.1 Hz), 4.60-4.67 (m, 1H), 7.31 (s, 1H), 7.56 (t, 1H, J = 9.3 Hz), 7.82 (d, 2H, J = 6.6 Hz), 8.61 (s, 1H), 10.10 (d, 1H, J = 6.6 Hz), 13.16 (br s, 1H), 14.32 (s, 1H). | 363 | 361 |
| 68 | 2-{[5-(3,5-difluorophenyl)-7-hydroxy[1,2,4]triazolo[1,5-a]pyridine-8-carbonyl]amino}-2-methylpropionic acid hydrochloride | HCl | $^1$H-NMR (DMSO-D$_6$, 400 MHz) δ: 1.63 (s, 6H), 7.27 (s, 1H), 7.51-7.60 (m, 1H), 7.76-7.83 (m, 2H), 8.61 (s, 1H), 10.15 (s, 1H). | 377 | 375 |
| 69 | (S)-2-[(7-hydroxy-5-phenethyl[1,2,4]triazolo[1,5-a]pyridine-8-carbonyl)amino] propionic acid hydrochloride | HCl | $^1$H-NMR (DMSO-D$_6$, 400 MHz) δ: 1.49 (d, 3H, J = 7.3 Hz), 3.12 (t, 2H, J = 7.8 Hz), 3.41 (t, 2H, J = 7.8 Hz), 4.56-4.63 (m, 1H), 6.81 (s, 1H), 7.18-7.33 (m, 5H), 8.61 (s, 1H), 9.97 (d, 1H, J = 7.1 Hz). | 355 | 353 |
| 70 | (R)-2-[(7-hydroxy-5-phenethyl[1,2,4]triazolo[1,5-a]pyridine-8-carbonyl)amino] propionic acid hydrochloride | HCl | $^1$H-NMR (DMSO-D$_6$, 400 MHz) δ: 1.49 (d, 3H, J = 7.3 Hz), 3.12 (t, 2H, J = 7.8 Hz), 3.41 (t, 2H, J = 7.8 Hz), 4.56-4.63 (m, 1H), 6.80 (s, 1H), 7.18-7.33 (m, 5H), 8.61 (s, 1H), 9.97 (d, 1H, J = 7.1 Hz). | 355 | 353 |

TABLE 14

| Ex. No. | compound name | structural formula | ¹H-NMR, δppm | MS (M + H) | MS (M − H) |
|---|---|---|---|---|---|
| 71 | [(7-hydroxy-6-pentyl[1,2,4]triazolo[1,5-a]pyridine-8-carbonyl)amino]acetic acid hydrochloride | | ¹H-NMR (DMSO-D₆, 400 MHz) δ: 0.87 (t, 3H, J = 6.9 Hz), 1.28-1.36 (m, 4H), 1.61 (t, 2H, J = 7.6 Hz), 2.62 (t, 2H, J = 7.6 Hz), 4.21 (d, 2H, J = 5.3 Hz), 8.50 (s, 1H), 8.88 (s, 1H), 9.93 (s, 1H), 14.81 (s, 1H). | 307 | 305 |
| 72 | {[7-hydroxy-5-(5-methylthiophen-2-yl)[1,2,4]triazolo[1,5-a]pyridine-8-carbonyl]amino}acetic acid hydrochloride | | ¹H-NMR (DMSO-D₆, 400 MHz) δ: 2.58 (s, 3H), 4.23 (d, 2H, J = 5.5 Hz), 7.07 (d, 1H, J = 3.7 Hz), 7.50 (s, 1H), 8.27 (d, 1H, J = 4.0 Hz), 8.67 (s, 1H), 9.85-9.90 (br m, 1H). | 333 | 331 |
| 73 | [(5-hexyl-7-hydroxy[1,2,4]triazolo[1,5-a]pyridine-8-carbonyl)amino]acetic acid hydrochloride | | ¹H-NMR (DMSO-D₆, 400 MHz) δ: 0.85 (3H, t, J = 7.0 Hz), 1.23-1.41 (6H, m), 1.71-1.81 (2H, m), 3.08 (2H, t, J = 7.7 Hz), 4.20 (2H, d, J = 5.6 Hz), 6.85 (1H, s), 8.56 (1H, s), 9.79-9.86 (1H, m). | 321 | 319 |
| 74 | [(7-hydroxy-5-pentyl[1,2,4]triazolo[1,5-a]pyridine-8-carbonyl)amino]acetic acid hydrochloride | | ¹H-NMR (DMSO-D₆, 400 MHz) δ: 0.84-0.91 (m, 3H), 1.29-1.40 (m, 4H), 1.72-1.83 (m, 2H), 3.09 (t, 2H, J = 7.5 Hz), 4.21 (d, 2H, J = 5.4 Hz), 6.86 (s, 1H), 8.56 (s, 1H), 9.83 (t, 1H, J = 5.4 Hz). | 307 | 305 |
| 75 | {[5-(2,5-difluorophenyl)-7-hydroxy[1,2,4]triazolo[1,5-a]pyridine-8-carbonyl]amino}acetic acid hydrochloride | | ¹H-NMR (DMSO-D₆, 400 MHz) δ: 4.25 (d, 2H, J = 5.6 Hz), 7.19 (s, 1H), 7.49-7.60 (m, 2H), 7.67-7.73 (m, 1H), 8.56 (s, 1H), 9.95 (t, 1H, J = 5.6 Hz). | 349 | 347 |

TABLE 15

| Ex. No. | compound name | structural formula | ¹H-NMR, δppm | MS (M + H) | MS (M − H) |
|---|---|---|---|---|---|
| 76 | {[7-hydroxy-5-(2,3,5-trifluorophenyl)[1,2,4]triazolo[1,5-a]pyridine-8-carbonyl]amino} acetic acid hydrochloride | 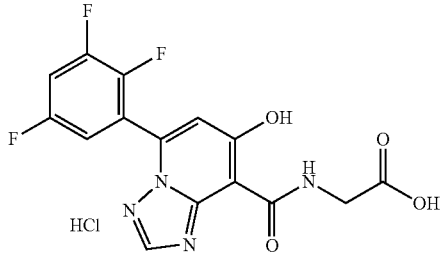 | ¹H-NMR (DMSO-D₆, 400 MHz) δ: 4.25 (d, 2H, J = 5.5 Hz), 7.25 (s, 1H), 7.58-7.64 (m, 1H), 7.86-7.93 (m, 1H), 8.59 (s, 1H), 9.95 (t, 1H, J = 5.5 Hz). | 367 | 365 |
| 77 | {[5-(2,4-difluorophenyl)-7-hydroxy[1,2,4]triazolo[1,5-a]pyridine-8-carbonyl]amino} acetic acid hydrochloride | 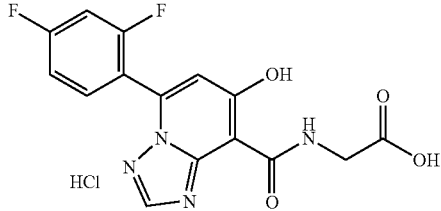 | ¹H-NMR (DMSO-D₆, 400 MHz) δ: 4.25 (d, 2H, J = 5.2 Hz), 7.14 (s, 1H), 7.30-7.39 (m, 1H), 7.50-7.60 (m, 1H), 7.81-7.89 (m, 1H), 8.55 (s, 1H), 9.94 (t, 1H, J = 5.4 Hz). | 349 | 347 |
| 78 | {[5-(4-chloro-3-fluorophenyl)-7-hydroxy[1,2,4]triazolo[1,5-a]pyridine-8-carbonyl]amino} acetic acid hydrochloride | 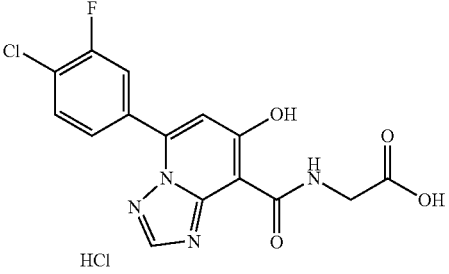 | ¹H-NMR (DMSO-D₆, 400 MHz) δ: 4.24 (d, 2H, J = 5.6 Hz), 7.26 (s, 1H), 7.82-7.86 (m, 1H), 7.93 (dd, 1H, J = 8.5, 1.6 Hz), 8.13 (dd, 1H, J = 10.5, 2.0 Hz), 8.61 (s, 1H), 9.98 (t, 1H, J = 5.4 Hz). | 365 | 363 |
| 79 | {[5-(3-fluoro-5-methylphenyl)-7-hydroxy[1,2,4]triazolo[1,5-a]pyridine-8-carbonyl]amino} acetic acid hydrochloride | 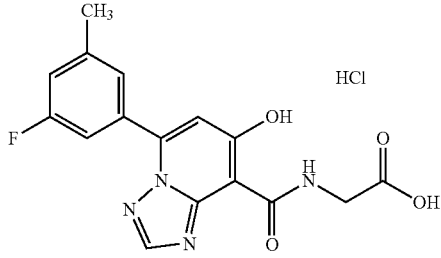 | ¹H-NMR (DMSO-D₆, 400 MHz) δ: 2.43 (s, 3H), 4.25 (d, 2H, J = 5.3 Hz), 7.18 (s, 1H), 7.32 (d, 1H, J = 9.3 Hz), 7.70 (d, 2H, J = 10.4 Hz), 8.60 (d, 1H, J = 0.7 Hz), 9.99 (t, 1H, J = 5.3 Hz). | 345 | 343 |
| 80 | [(6-chloro-7-hydroxy-5-phenethyl[1,2,4]triazolo[1,5-a]pyridine-8-carbonyl)amino] acetic acid hydrochloride | 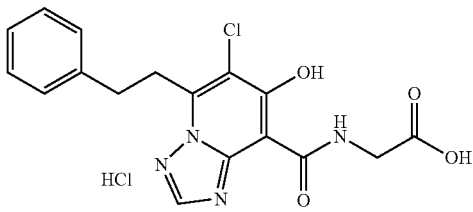 | ¹H-NMR (DMSO-D₆, 400 MHz) δ: 3.05 (t, 2H, J = 7.8 Hz), 3.56 (t, 2H, J = 7.8 Hz), 4.17 (d, 2H, J = 5.1 Hz), 7.16-7.22 (m, 3H), 7.23-7.29 (m, 2H), 8.60 (s, 1H). | 375 | 373 |
| 81 | [(6-chloro-7-hydroxy-5-propyl[1,2,4]triazolo[1,5-a]pyridine-8-carbonyl)amino] acetic acid hydrochloride | 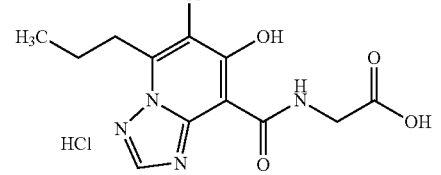 | ¹H-NMR (DMSO-D₆, 400 MHz) δ: 3.09 (t, 2H, J = 7.8 Hz), 3.28 (t, 2H, J = 7.8 Hz), 4.25 (d, 2H, J = 5.6 Hz), 7.16-7.32 (m, 5H), 7.36 (s, 1H), 8.68 (s, 1H), 10.42 (t, 1H, J = 5.6 Hz), 13.26 (s, 1H). | 313 | 311 |

TABLE 16

| Ex. No. | compound name | structural formula | ¹H-NMR, δppm | MS (M + H) | MS (M − H) |
|---|---|---|---|---|---|
| 82 | {[5-(4-cyclopropyl-2-fluorophenyl)-7-hydroxy[1,2,4]triazolo[1,5-a]pyridine-8-carbonyl]amino}acetic acid hydrochloride | | ¹H-NMR (DMSO-D₆, 400 MHz) δ: 0.82-0.86 (m, 2H), 1.05-1.10 (m, 2H), 2.04-2.11 (m, 1H), 4.24 (d, 2H, J = 5.6 Hz), 7.06 (s, 1H), 7.14 (d, 1H, J = 8.1 Hz), 7.15 (d, 1H, J = 7.7 Hz), 7.62 (dd, 1H, J = 7.7, 7.7 Hz), 8.53 (s, 1H), 9.94 (t, 1H, J = 5.6 Hz). | 371 | 369 |
| 83 | [(6-hydroxy-8-phenyl[1,2,4]triazolo[1,5-a]pyridine-5-carbonyl)amino]acetic acid hydrochloride | | ¹H-NMR (DMSO-D₆, 400 MHz) δ: 4.28 (d, 2H, J = 5.5 Hz), 7.50-7.63 (m, 3H), 7.80 (s, 1H), 8.21 (d, 2H, J = 7.3 Hz), 8.74 (s, 1H), 10.53 (t, 1H, J = 5.5 Hz), 13.36 (s, 1H). | 313 | 311 |
| 84 | {[8-(3-chlorophenyl)-6-hydroxy[1,2,4]triazolo[1,5-a]pyridine-5-carbonyl]amino}acetic acid | | ¹H-NMR (DMSO-D₆, 400 MHz) δ: 4.28 (d, 2H, J = 5.6 Hz), 7.58-7.64 (m, 2H), 7.92 (s, 1H), 8.15-8.21 (m, 1H), 8.37-8.39 (m, 1H), 8.76 (s, 1H), 10.54 (t, 1H, J = 5.4 Hz), 13.06 (s, 1H), 13.36 (s, 1H). | 347 | 345 |
| 85 | {[8-(3,5-difluorophenyl)-6-hydroxy[1,2,4]triazolo[1,5-a]pyridine-5-carbonyl]amino}acetic acid hydrochloride | | ¹H-NMR (DMSO-D₆, 400 MHz) δ: 4.28 (d, 2H, J = 5.6 Hz), 7.47 (tt, 1H, J = 9.3, 2.3 Hz), 8.03 (s, 1H), 8.06-8.14 (m, 2H), 8.78 (s, 1H), 10.54 (t, 1H, J = 5.4 Hz), 13.35 (s, 1H). | 349 | 347 |
| 86 | [(8-benzyl-6-hydroxy[1,2,4]triazolo[1,5-a]pyridine-5-carbonyl)amino]acetic acid hydrochloride | | ¹H-NMR (DMSO-D₆, 400 MHz) δ 4.24 (d, 2H, J = 5.6 Hz), 4.33 (s, 2H), 7.20-7.25 (m, 1H), 7.28-7.33 (m, 2H), 7.35 (s, 1H), 7.38-7.41 (m, 2H), 8.66 (s, 1H), 10.40 (t, 1H, J = 5.6 Hz), 13.27 (s, 1H). | 327 | 325 |

TABLE 17

| Ex. No. | compound name | structural formula | ¹H-NMR, δppm | MS (M + H) | MS (M − H) |
|---|---|---|---|---|---|
| 87 | [(6-hydroxy-8 phenethyl[1,2,4]triazolo[1,5-a]pyridine-5-carbonyl)amino] acetic acid hydrochloride | | ¹H-NMR (DMSO-D₆, 400 MHz) δ: 3.09 (t, 2H, J = 7.8 Hz), 3.28 (t, 2H, J = 7.8 Hz), 4.25 (d, 2H, J = 5.6 Hz), 7.16-7.32 (m, 5H), 7.36 (s, 1H), 10.42 (t, 1H, J = 5.6 Hz), 13.26 (s, 1H). | 341 | 339 |
| 88 | {[8-(2-chlorophenyl)-6-hydroxy[1,2,4]triazolo[1,5-a]pyridine-5-carbonyl]amino} acetic acid | | ¹H-NMR (DMSO-D₆, 400 MHz) δ: 4.28 (d, 2H, J = 5.6 Hz), 7.49-7.59 (m, 2H), 7.60-7.63 (m, 2H), 7.67 (dd, 1H, J = 7.9, 1.4 Hz), 8.66 (s, 1H), 10.50 (t, 1H, J = 5.6 Hz), 13.06 (s, 1H), 13.37 (s, 1H). | 347 | 345 |
| 89 | {[8-(3,5-dichlorophenyl)-6-hydroxy[1,2,4]triazolo[1,5-a]pyridine-5-carbonyl]amino} acetic acid hydrochloride | | ¹H-NMR (DMSO-D₆, 400 MHz) δ: 4.28 (d, 2H, J = 5.3 Hz), 7.80 (t, 1H, J = 1.9 Hz), 8.03 (s, 1H), 8.36 (d, 2H, J = 1.8 Hz), 8.77 (s, 1H), 10.53 (t, 1H, J = 5.3 Hz), 13.34 (s, 1H). | 381 | 379 |
| 90 | ({8-[2-(4-fluorophenyl)-ethyl]-6-hydroxy[1,2,4]triazolo[1,5-a]pyridine-5-carbonyl}amino) acetic acid hydrochloride | | ¹H-NMR (DMSO-D₆, 400 MHz) δ: 3.09 (t, 2H, J = 7.9 Hz), 3.27 (t, 2H, J = 7.7 Hz), 4.25 (d, 2H, J = 5.5 Hz), 7.10 (t, 2H, J = 8.9 Hz), 7.26 (dd, 2H, J = 8.7, 5.8 Hz), 7.35 (s, 1H), 8.66 (s, 1H), 10.42 (t, 1H, J = 5.3 Hz), 13.26 (s, 1H). | 359 | 357 |
| 91 | [(8-cyclohexylmethyl-6-hydroxy[1,2,4]triazolo[1,5-a]pyridine-5-carbonyl)amino] acetic acid hydrochloride | | ¹H-NMR (DMSO-D₆, 400 MHz) δ: 0.94-1.23 (m, 5H), 1.53-1.70 (m, 5H), 1.80-1.94 (m, 1H), 2.86 (d, 2H, J = 7.2 Hz), 4.25 (d, 2H, J = 5.6 Hz), 7.36 (s, 1H), 8.62 (s, 1H), 10.42 (t, 1H, J = 5.6 Hz), 13.28 (s, 1H). | 333 | 331 |

TABLE 18

| Ex. No. | compound name | structural formula | ¹H-NMR, δppm | MS (M + H) | MS (M − H) |
|---|---|---|---|---|---|
| 92 | [(8-cyclohexyl-6-hydroxy[1,2,4]triazolo[1,5-a]pyridine-8-carbonyl]amino]acetic acid hydrochloride | | ¹H-NMR (DMSO-$D_6$, 400 MHz) δ: 1.23-1.34 (m, 1H), 1.38-1.49 (m, 2H), 1.57-1.67 (m, 2H), 1.73-1.77 (m, 1H), 1.82-1.86 (m, 2H), 1.91-1.96 (m, 2H), 3.15-3.22 (m, 1H), 4.25 (d, 2H, J = 5.6 Hz), 7.33 (s, 1H), 8.63 (s, 1H), 10.42 (t, 1H, J = 5.6 Hz), 13.29 (s, 1H). | 319 | 317 |
| 93 | [(8-cyclohex-1-enyl-6-hydroxy[1,2,4]triazolo[1,5-a]pyridine-5-carbonyl)amino]acetic acid hydrochloride | | ¹H-NMR (DMSO-$D_6$, 400 MHz) δ: 1.62-1.68 (m, 2H), 1.74-1.80 (m, 2H), 2.31-2.35 (m, 2H), 2.49-2.54 (m, 2H), 4.25 (d, 2H, J = 5.6 Hz), 7.33 (s, 1H), 7.58-7.61 (m, 1H), 8.66 (s, 1H), 10.48 (t, 1H, J = 5.6 Hz), 13.28 (s, 1H). | 317 | 315 |
| 94 | {[8-(3-chloro-4-fluorophenyl)-6-hydroxy[1,2,4]triazolo[1,5-a]pyridine-5-carbonyl]amino}acetic acid hydrochloride | | ¹H-NMR (DMSO-$D_6$, 400 MHz) δ: 4.28 (d, 2H, J = 5.5 Hz), 7.64 (t, 1H, J = 8.9 Hz), 7.94 (s, 1H), 8.29 (dq, 1H, J = 8.7, 2.3 Hz), 8.57 (dd, 1H, J = 7.2, 2.3 Hz), 8.77 (s, 1H), 10.52 (t, 1H, J = 5.5 Hz), 13.36 (s, 1H). | 365 | 363 |
| 95 | {[8-(3,4-dichlorophenyl)-6-hydroxy[1,2,4]triazolo[1,5-a]pyridine-5-carbonyl]amino}acetic acid hydrochloride | | ¹H-NMR (DMSO-$D_6$, 400 MHz) δ: 4.28 (d, 2H, J = 5.5 Hz), 7.84 (d, 1H, J = 8.4 Hz), 7.97 (s, 1H), 8.25 (dd, 1H, J = 8.4, 2.2 Hz), 8.60 (d, 1H, J = 2.2 Hz), 8.77 (s, 1H), 10.52 (t, 1H, J = 5.5 Hz), 13.35 (s, 1H). | 381 | 379 |

TABLE 19

| Ex. No. | compound name | structural formula | ¹H-NMR, δppm | MS (M + H) | MS (M − H) |
|---|---|---|---|---|---|
| 96 | {[8-(5-chlorothiophen-2-yl)-6-hydroxy[1,2,4]triazolo[1,5-a]pyridine-5-carbonyl]amino}acetic acid hydrochloride | | ¹H-NMR (DMSO-$D_6$, 400 MHz) δ: 4.26 (d, 2H, J = 5.5 Hz), 7.35 (d, 1H, J = 4.2 Hz), 8.06 (s, 1H), 8.22 (d, 1H, J = 4.2 Hz), 8.78 (s, 1H), 10.41 (t, 1H, J = 5.5 Hz), 13.35 (s, 1H). | 353 | 351 |

TABLE 19-continued

| Ex. No. | compound name | structural formula | ¹H-NMR, δppm | MS (M + H) | MS (M − H) |
|---|---|---|---|---|---|
| 97 | {[8-(3,5-bis-trifluoromethyl-phenyl)-6-hydroxy[1,2,4]triazolo[1,5-a]pyridine-5-carbonyl]amino} acetic acid hydrochloride | | ¹H-NMR (DMSO-D₆, 400 MHz) δ: 4.29 (d, 2H, J = 5.5 Hz), 8.24 (s, 1H), 8.29 (s, 1H), 8.82 (s, 1H), 8.98 (s, 2H), 10.55 (t, 1H, J = 5.5 Hz), 13.36 (s, 1H). | 449 | 447 |
| 98 | {[8-(2-cyclohexylethyl)-6-hydroxy[1,2,4]triazolo[1,5-a]pyridine-5-carbonyl]amino} acetic acid hydrochloride | | ¹H-NMR (DMSO-D₆, 400 MHz) δ: 0.85-1.34 (m, 6H), 1.53-1.82 (m, 7H), 2.94-3.02 (m, 2H), 4.25 (d, 2H, J = 5.6 Hz), 7.40 (s, 1H), 8.63 (s, 1H), 10.41 (t, 1H, J = 5.6 Hz), 13.28 (s, 1H). | 347 | 345 |
| 99 | {[8-(2-cyclopentylethyl)-6-hydroxy[1,2,4]triazolo[1,5-a]pyridine-5-carbonyl]amino} acetic acid hydrochloride | | ¹H-NMR (DMSO-D₆, 400 MHz) δ: 1.07-1.22 (m, 2H), 1.41-1.65 (m, 4H), 1.70-1.86 (m, 5H), 2.93-3.02 (m, 2H), 4.25 (d, 2H, J = 5.6 Hz), 7.40 (s, 1H), 8.64 (s, 1H), 10.41 (t, 1H, J = 5.6 Hz), 13.28 (s, 1H). | 333 | 331 |
| 100 | ({6-hydroxy-8-[2-(2-trifluoromethyl phenyl)ethyl][1,2,4]triazolo[1,5-a]pyridine-5-carbonyl}amino) acetic acid hydrochloride | | ¹H-NMR (DMSO-D₆, 400 MHz) δ: 3.21-3.35 (m, 4H), 4.25 (d, 2H, J = 5.6 Hz), 7.38 (s, 1H), 7.44 (t, 1H, J = 7.5 Hz), 7.56 (d, 1H, J = 7.7 Hz), 7.63 (t, 1H, J = 7.7 Hz), 7.70 (d, 1H, J = 7.5 Hz), 8.68 (s, 1H), 10.43 (t, 1H, J = 5.6 Hz), 13.28 (s, 1H). | 409 | 407 |

TABLE 20

| Ex. No. | compound name | structural formula | ¹H-NMR, δppm | MS (M + H) | MS (M − H) |
|---|---|---|---|---|---|
| 101 | ({6-hydroxy-8-[2-(3-trifluoromethyl phenyl)ethyl] [1,2,4]triazolo[1,5-a]pyridine-5-carbonyl}amino) acetic acid hydrochloride | | ¹H-NMR (DMSO-D₆, 400 MHz) δ: 3.20 (dd, 2H, J = 9.4, 6.5 Hz), 3.32 (dd, 2H, J = 9.4, 6.5 Hz), 4.25 (d, 2H, J = 5.6 Hz), 7.40 (s, 1H), 7.49-7.59 (m, 3H), 7.63 (s, 1H), 8.68 (s, 1H), J = 5.6 Hz), 13.27 (s, 1H). | 409 | 407 |

TABLE 20-continued

| Ex. No. | compound name | structural formula | ¹H-NMR, δppm | MS (M + H) | MS (M − H) |
|---|---|---|---|---|---|
| 102 | ({6-hydroxy-8-[2-(4-trifluoromethylphenyl)ethyl][1,2,4]triazolo[1,5-a]pyridine-5-carbonyl}amino)acetic acid hydrochloride | | ¹H-NMR (DMSO-D₆, 400 MHz) δ: 3.17-3.24 (m, 2H), 3.28-3.36 (m, 2H), 4.25 (d, 2H, J = 5.6 Hz), 7.40 (s, 1H)m 7.48 (d, 2H, J = 7.9 Hz), 7.65 (d, 2H, J = 7.9 Hz), 8.68 (s, 1H), 10.42 (t, 1H, J = 5.6 Hz), 13.27 (s, 1H). | 409 | 407 |
| 103 | {[8-(3-chloro-5-cyclopropylphenyl)-6-hydroxy[1,2,4]triazolo[1,5-a]pyridine-5-carbonyl]amino}acetic acid hydrochloride | | ¹H-NMR (DMSO-D₆, 400 MHz) δ: 0.84-0.90 (m, 2H), 1.01-1.06 (m, 2H), 2.03-2.10 (m, 1H), 4.28 (d, 2H, J = 5.4 Hz), 7.31 (dd, 1H, J = 1.8, 1.8 Hz), 7.83 (dd, 1H, J = 1.8, 1.8 Hz), 7.93 (s, 1H), 8.13 (dd, 1H, J = 1.8, 1.8 Hz), 8.75 (s, 1H), 10.53 (t, 1H, J = 5.4 Hz), 13.35 (s, 1H). | 387 | 385 |
| 104 | {[8-(3-fluoro-5-trifluoromethylphenyl)-6-hydroxy[1,2,4]triazolo[1,5-a]pyridine-5-carbonyl]amino}acetic acid hydrochloride | | ¹H-NMR (DMSO-D₆, 400 MHz) δ: 4.29 (d, 2H, J = 5.5 Hz), 7.89 (d, 1H, J = 8.6 Hz), 8.12 (s, 1H), 8.46 (d, 1H, J = 8.6 Hz), 8.63 (s, 1H), 8.80 (s, 1H), 10.54 (t, 1H, J = 5.5 Hz), 13.36 (s, 1H). | 399 | 397 |
| 105 | {[8-(3-chloro-5-fluorophenyl)-6-hydroxy[1,2,4]triazolo[1,5-a]pyridine-5-carbonyl]amino}acetic acid hydrochloride | | ¹H-NMR (DMSO-D₆, 400 MHz) δ: 4.28 (d, 2H, J = 5.3 Hz), 7.62-7.67 (m, 1H), 8.03 (s, 1H), 8.13-8.19 (m, 1H), 8.31 (s, 1H), 8.78 (s, 1H), 10.54 (t, 1H, J = 5.3 Hz), 13.35 (s, 1H). | 365 | 363 |

TABLE 21

| Ex. No. | compound name | structural formula | ¹H-NMR, δppm | MS (M + H) | MS (M − H) |
|---|---|---|---|---|---|
| 106 | {[8-(4-fluoro-3-trifluoromethylphenyl)-6-hydroxy[1,2,4]triazolo[1,5-a]pyridine-5-carbonyl]amino}acetic acid hydrochloride | | ¹H-NMR (DMSO-D₆, 400 MHz) δ: 4.29 (d, 2H, J = 5.6 Hz), 7.71-7.80 (m, 1H), 8.03 (s, 1H), 8.56-8.63 (m, 1H), 8.73-8.82 (m, 2H), 10.53 (t, 1H, J = 5.6 Hz), 13.37 (s, 1H). | 399 | 397 |

TABLE 21-continued

| Ex. No. | compound name | structural formula | ¹H-NMR, δppm | MS (M + H) | MS (M − H) |
|---|---|---|---|---|---|
| 107 | [(6-hydroxy[1,2,4]triazolo[1,5-a]pyridine-5-carbonyl]amino} acetic acid hydrochloride | | ¹H-NMR (DMSO-D$_6$, 400 MHz) δ: 4.27 (d, 2H, J = 5.3 Hz), 7.56 (d, 1H, J = 9.7 Hz), 8.09 (d, 1H, J = 9.7 Hz), 8.68 (s, 1H), 10.49 (t, 1H, J = 5.3 Hz), 13.29 (br s, 1H). | 237 | 235 |
| 108 | {[8-(4-chlorophenyl)-6-hydroxy[1,2,4]triazolo[1,5-a]pyridine-5-carbonyl]amino} acetic acid | | ¹H-NMR (DMSO-D$_6$, 400 MHz) δ: 4.24 (d, 2H, J = 5.2 Hz), 7.62-7.67 (m, 2H), 7.86 (s, 1H), 8.26-8.31 (m, 2H), 8.74 (s, 1H), 10.53 (t, 1H, J = 5.2 Hz), 13.31 (br s, 1H). | 347 | 345 |
| 109 | ({8-[2-(3,5-difluoro-phenyl)-ethyl]-6-hydroxy[1,2,4]triazolo[1,5-a]pyridine-5-carbonyl}amino) acetic acid hydrochloride | | ¹H-NMR (DMSO-D$_6$, 400 MHz) δ: 3.13 (t, 2H, J = 7.9 Hz), 3.30 (t, 2H, J = 7.9 Hz), 4.25 (d, 2H, J = 5.2 Hz), 6.98-7.08 (m, 3H), 7.40 (s, 1H), 8.67 (s, 1H), 10.42 (t, 1H, J = 5.2 Hz), 13.27 (br s, 1H). | 377 | 375 |
| 110 | {[6-hydroxy-8-(3-trifluoromethylphenyl)[1,2,4]triazolo[1,5-a]pyridine-5-carbonyl]amino} acetic acid hydrochloride | | ¹H-NMR (DMSO-D$_6$, 400 MHz) δ 4.29 (d, 2H, J = 5.5 Hz), 7.82 (t, 1H, J = 7.9 Hz), 7.91 (d, 1H, J = 7.9 Hz), 8.00 (s, 1H), 8.48 (d, 1H), 10.54 (t, 1H, J = 5.5 Hz), 13.36 (br s, 1H). | 381 | 379 |

TABLE 22

| Ex. No. | compound name | structural formula | ¹H-NMR, δppm | MS (M + H) | MS (M − H) |
|---|---|---|---|---|---|
| 111 | [(7-hydroxy-3,6-diphenyl[1,2,4]triazolo[4,3-a]pyridine-8-carbonyl)amino] acetic acid hydrochloride | | ¹H-NMR (DMSO-D$_6$, 400 MHz) δ: 4.09 (d, 2H, J = 5.5 Hz), 7.36-7.44 (m, 3H), 7.57-7.66 (m, 5H), 7.90 (d, 2H, J = 7.3 Hz), 8.00 (s, 1H), 10.56 (t, 1H, J = 5.3 Hz), 12.61 (s, 1H), 13.95 (s, 1H). | 389 | 387 |

TABLE 22-continued

| Ex. No. | compound name | structural formula | ¹H-NMR, δppm | MS (M + H) | MS (M − H) |
|---|---|---|---|---|---|
| 112 | [(7-hydroxy-3-methyl-6-phenyl[1,2,4]triazolo[4,3-a]pyridine-8-carbonyl)amino]acetic acid hydrochloride | | ¹H-NMR (DMSO-D₆, 400 MHz) δ: 2.62 (s, 3H), 4.05 (d, 2H, J = 5.5 Hz), 7.39-7.46 (m, 3H), 7.63 (d, 2H, J = 6.8 Hz), 8.21 (s, 1H), 10.54 (t, 1H, J = 5.3 Hz), 12.58 (s, 1H), 13.44 (s, 1H). | 327 | 325 |
| 113 | [(7-hydroxy-3-phenyl[1,2,4]triazolo[4,3-a]pyridine-8-carbonyl)amino]acetic acid | | ¹H-NMR (DMSO-D₆, 400 MHz) δ: 4.06-4.24 (m, 2H), 6.47-6.74 (m, 1H), 7.58-7.71 (m, 3H), 7.78-7.89 (m, 2H), 7.99-8.42 (m, 1H), 9.99-10.43 (m, 1H). | 313 | 311 |
| 114 | [(7-hydroxy-3-phenethyl[1,2,4]triazolo[4,3-a]pyridine-8-carbonyl)amino]acetic acid hydrochloride | | ¹H-NMR (DMSO-D₆, 400 MHz) δ: 3.08 (t, 2H, J = 7.7 Hz), 3.28 (t, 2H, J = 7.7 Hz), 4.05 (d, 2H, J = 5.2 Hz), 6.46 (d, 1H, J = 7.3 Hz), 7.16-7.25 (m, 1H), 7.26-7.32 (m, 4H), 8.19 (d, 1H, J = 7.3 Hz), 10.33 (br s, 1H), 13.52 (br s, 1H). | 341 | 339 |
| 115 | {[3-(2-cyclohexylethyl)-7-hydroxy[1,2,4]triazolo[4,3-a]pyridine-8-carbonyl]amino}acetic acid hydrochloride | | ¹H-NMR (DMSO-D₆, 400 MHz) δ: 0.90-0.98 (m, 2H), 1.17-1.22 (m, 3H), 1.28-1.40 (m, 1H), 1.62-1.67 (m, 5H), 1.75-1.78 (m, 2H), 2.96 (t, 2H, J = 7.9 Hz), 4.04 (d, 2H, J = 5.2 Hz), 6.52 (d, 1H, J = 7.7 Hz), 8.21 (d, 1H, J = 7.7 Hz), 10.28 (br s, 1H). | 347 | 345 |

TABLE 23

| Ex. No. | compound name | structural formula | ¹H-NMR, δppm | MS (M + H) | MS (M − H) |
|---|---|---|---|---|---|
| 116 | [(7-hydroxy-5-phenethyl[1,2,4]triazolo[1,5-a]pyridine-8-carbonyl)amino]acetic acid | | ¹H-NMR (DMSO-D₆, 400 MHz) δ: 3.12 (t, 2H, J = 7.9 Hz), 3.40 (t, 3H, J = 7.9 Hz), 4.22 (d, 2H, J = 5.2 Hz), 6.79 (s, 1H), 7.21-7.29 (m, 5H), 8.58 (s, 1H), 9.84 (t, 1H, J = 5.2 Hz), 12.97 (s, 1H), 14.22 (s, 1H). | 341 | 339 |

TABLE 23-continued

| Ex. No. | compound name | structural formula | ¹H-NMR, δppm | MS (M + H) | MS (M − H) |
|---|---|---|---|---|---|
| 117 | [(5-butyl-7-hydroxy[1,2,4]triazolo[1,5-a]pyridine-8-carbonyl)amino]acetic acid | 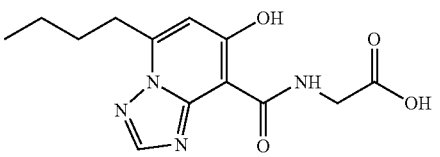 | ¹H-NMR (DMSO-D₆, 400 MHz) δ: 0.93 (t, 3H, J = 7.5 Hz), 1.33-1.44 (m, 2H), 1.71-1.90 (m, 2H), 3.10 (t, 2H, J = 7.5 Hz), 4.20 (d, 2H, J = 5.2 Hz), 6.85 (s, 1H), 8.55 (s, 1H), 9.84 (br s, 1H), 14.26 (br s, 1H). | 293 | 291 |
| 118 | {[5-(3-fluoro-5-trifluoromethyl phenyl)-7-hydroxy[1,2,4]triazolo[1,5-a]pyridine-8-carbonyl]amino} acetic acid | 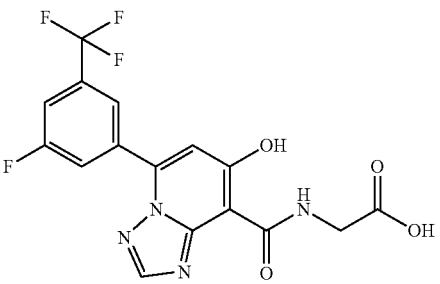 | ¹H-NMR (DMSO-D₆, 400 MHz) δ: 4.25 (d, 2H, J = 5.1 Hz), 7.39 (s, 1H), 7.99 (d, 1H, J = 8.6 Hz), 8.23 (d, 1H, J = 9.5 Hz), 8.31 (s, 1H), 8.62 (s, 1H), 9.98 (s, 1H), 13.01 (s, 1H), 14.41 (s, 1H). | 399 | 397 |
| 119 | [(7-hydroxy-5-pentyl[1,2,4]triazolo[1,5-a]pyridine-8-carbonyl)amino]acetic acid | 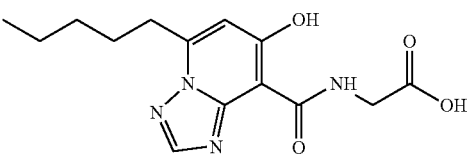 | ¹H-NMR (DMSO-D₆, 400 MHz) δ: 0.88 (t, 3H, J = 7.6 Hz), 1.28-1.40 (m, 4H), 1.73-1.83 (m, 2H), 3.09 (t, 2H, J = 7.6 Hz), 4.21 (d, 2H, J = 5.5 Hz), 6.85 (s, 1H), 8.54 (s, 1H), 9.84 (t, 1H, J = 5.5 Hz), 12.94 (s, 1H), 14.25 (s, 1H). | 307 | 305 |

TABLE 24

| Ex. No. | compound name | structural formula | ¹H-NMR, δppm | MS (M + H) | MS (M − H) |
|---|---|---|---|---|---|
| 120 | {[5-(3-chlorophenyl)-7-hydroxy[1,2,4]triazolo[1,5-a]pyridine-8-carbonyl]amino} acetic acid | 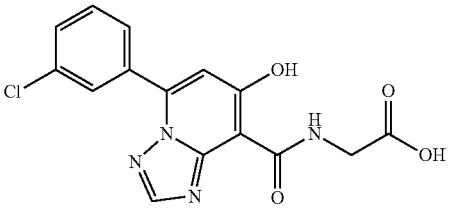 | ¹H-NMR (DMSO-D₆, 400 MHz) δ: 4.24 (d, 2H, J = 5.3 Hz), 7.22 (s, 1H), 7.58-7.70 (m, 2H), 7.96 (d, 1H, J = 7.7 Hz), 8.11 (s, 1H), 8.59 (s, 1H), 9.97 (s, 1H), 14.38 (s, 1H). | 347 | 345 |
| 121 | {[5-(4-fluoro-3-trifluoromethyl phenyl)-7-hydroxy[1,2,4]triazolo[1,5-a]pyridine-8-carbonyl]amino} acetic acid | 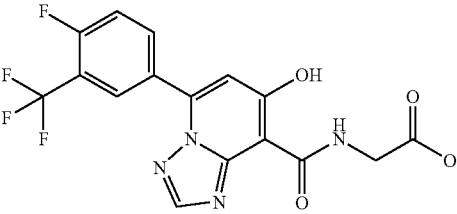 | ¹H-NMR (DMSO-D₆, 400 MHz) δ: 4.24 (2H, d, J = 5.6 Hz), 7.30 (1H, s), 7.77 (1H, dd, J = 10.5, 9.3 Hz), 8.36-8.40 (1H, m), 8.47 (1H, d, J = 6.9 Hz), 8.60 (1H, s), 9.97 (1H, br s), 14.38 (1H, br s). | 399 | 397 |

TABLE 24-continued

| Ex. No. | compound name | structural formula | $^1$H-NMR, δppm | MS (M + H) | MS (M − H) |
|---|---|---|---|---|---|
| 122 | {[5-(3-cyclopropyl-5-fluorophenyl)-7-hydroxy[1,2,4]triazolo[1,5-a]pyridine-8-carbonyl]amino} acetic acid | | $^1$H-NMR (DMSO-D$_6$, 400 MHz) δ: 0.81-0.87 (m, 2H), 1.00-1.07 (m, 2H), 2.03-2.10 (m, 1H), 4.22 (d, 2H, J = 5.6 Hz), 7.13-7.23 (m, 2H), 7.56 (s, 1H), 7.63 (d, 1H, J = 9.3 Hz), 8.58 (s, 1H), 9.99 (s, 1H), 14.36 (s, 1H). | 371 | 369 |

Examples of the Formulation Example of the present invention include the following formulations. However, the present invention is not limited by such Formulation Examples.

Formulation Example 1

Production of Capsule

| 1) compound of Example 1 | 30 mg |
|---|---|
| 2) microcrystalline cellulose | 10 mg |
| 3) lactose | 19 mg |
| 4) magnesium stearate | 1 mg |

1), 2), 3) and 4) are mixed and filled in a gelatin capsule.

Formulation Example 2

Production of Tablet

| 1) compound of Example 1 | 10 g |
|---|---|
| 2) lactose | 50 g |
| 3) cornstarch | 15 g |
| 4) carmellose calcium | 44 g |
| 5) magnesium stearate | 1 g |

The total amount of 1), 2), 3) and 30 g of 4) are kneaded with water, vacuum dried and sieved. The sieved powder is mixed with 14 g of 4) and 1 g of 5), and the mixture is tableted by a tableting machine. In this way, 1000 tablets containing 10 mg of the compound of Example 1 per tablet are obtained.

Next, the evaluation methods of the human PHD inhibitory activity and human EPO production-inducing activity of the compound of the present invention or a pharmaceutically acceptable salt thereof, or a solvate thereof are explained.

Experimental Example 1

Measurement of Human PHD Inhibitory Activity i) Expression and Purification of Human PHD2

Human PHD2 was expressed in insect cell (Sf9 cell). FLAG-tag was inserted into the N-terminal in the translational region of human PHD2-registered sequence (NM__022051), and the sequence was introduced into a pVL1393 vector, and the sequence was confirmed. The vector and baculovirus were cotransfected into Sf9, and human PHD2 expression baculovirus was isolated in Sf9. By using the virus, human PHD2-expressed cell was prepared. After the cell was cultured at 27° C. for 72 hr, cell lysing solution containing various protease inhibitors was added, and the cell was disrupted by sonication. The cell lysate was flowed into a column filled with ANTI-FLAG M2 Affinity Gel Freezer Safe (SIGMA), washed, and the N-terminal FLAG-tag-added human PHD2 was eluted and collected. The purification product was confirmed to be human PHD2 enzyme by Western-Blotting using an anti-FLAG antibody and an anti-PHD2 antibody.

ii) Expression and Purification of VBC Complex

VBC complex (VHL/Elongin B/Elongin C) was expressed in *Escherichia coli* (BL21(DE3)). GST-fusion was inserted into the N-terminal in the translational region of human VHL-registered sequence (NM__000551). FLAG-tag was inserted into the N-terminal in the translational region of human Elongin B-registered sequence (NM__207013), and the sequences were introduced into a pETDuet-1 vector, and the sequences were confirmed. His-tag was inserted into the N-terminal in the translational region of human Elongin C-registered sequence (NM__005648), and the sequence was introduced into a pRSFDuet-1 vector, and the sequence was confirmed. After these expression vectors were transfected into *Escherichia coli* (BL21(DE3)), *Escherichia coli* was cultured at 37° C. in the medium containing IPTG. The collected *Escherichia coli* was disrupted by sonication and flowed into a column filled with Ni-NTA superflow (QIAGEN), washed, and the product was eluted and collected. The eluate was flowed into a column filled with Glutathione Sepharose 4B, washed, and the product was eluted and collected. The purification product was confirmed to be human VHL•human Elongin B and human Elongin C by Western-Blotting using an anti-GST antibody•an anti-FLAG antibody and an anti-His antibody.

iii) Binding Activity of VBC Complex

The binding activity of the VBC complex obtained in the aforementioned ii) to 19 residues of Biotin-labeled partial peptide (HIF-1α-C19) based on the sequence of HIF-1α or Biotin-labeled partial peptide (HIF-1α-C19 (Hyp)) wherein proline residue in said sequence is hydroxylated was measured on streptavidin Coated Plate. For detection, ELISA using an anti-GST antibody was performed, and binding of VBC complex only to hydroxylated HIF-1α partial peptide was confirmed.

iv) Measurement of Human PHD Inhibitory Activity

As for human PHD2 enzyme activity, hydroxylation of proline residue contained in the 19 residues of the partial peptide based on the sequence of HIF-1α as a substrate was measured by TR-FRET (Time-Resolved Fluorescence Resonance Energy Transfer) method.

The enzyme and substrate were each diluted with 50 mM tris-hydrochloride buffer (pH 7.5) containing 50 μM iron sulfate, 120 mM NaCl, 0.1% BSA, 0.1 mM ascorbic acid, 10 μM 2-oxoglutaric acid, 0.2 mM CHAPS, and the test compound was diluted with dimethyl sulfoxide (DMSO).

A test compound and a substrate solution were added to a 96-well plate. The reaction was started by addition of a human PHD2 enzyme solution (final concentration 1 nM) to the reaction system. After incubation at 25° C. for 30 min, a stop solution containing EDTA was added, and a VBC complex solution containing europium (Eu) and Xlent was added, and the amount of hydroxylated proline residue was quantified by time-resolved fluorescence spectroscopy. The time-resolved fluorescence in each well was measured, and the human PHD inhibitory activity (%) of the test compound was calculated based on the values of enzyme non-addition well and test compound non-addition well. The human PHD inhibitory activity of each compound is shown by $IC_{50}$ (μM) or as human PHD inhibitory activity (%) at 30 μM in the following Tables 25 to 29. In these Tables, the values consisting solely of numbers show $IC_{50}$ (4M) and those containing % show human PHD inhibitory activity (%) at 30 μm.

TABLE 25

| Ex. No. | $IC_{50}$ (μM) or inhibitory activity (%) at 30 μM in vitro |
|---|---|
| 1 | 0.42 |
| 2 | 0.22 |
| 3 | 0.45 |
| 4 | 7.15 |
| 5 | 1.17 |
| 6 | 0.87 |
| 7 | 1.59 |
| 8 | 0.49 |
| 9 | 1.57 |
| 10 | 1.33 |
| 11 | 0.29 |
| 12 | 0.82 |
| 13 | 1.31 |
| 14 | 0.23 |
| 15 | 1.80 |
| 16 | 0.32 |
| 17 | 0.29 |
| 18 | 0.48 |
| 19 | 0.26 |
| 20 | 0.59 |
| 21 | 0.25 |
| 22 | 0.21 |
| 23 | 0.19 |
| 24 | 0.57 |
| 25 | 0.25 |
| 26 | 0.33 |
| 27 | 0.74 |
| 28 | 1.38 |
| 29 | 0.92 |

TABLE 26

| Ex. No. | $IC_{50}$ (μM) or inhibitory activity (%) at 30 μM in vitro |
|---|---|
| 30 | 0.98 |
| 31 | 0.80 |
| 32 | 0.38 |
| 33 | 0.46 |
| 34 | 0.43 |
| 35 | 0.88 |
| 36 | 0.72 |
| 37 | 0.20 |

TABLE 26-continued

| Ex. No. | $IC_{50}$ (μM) or inhibitory activity (%) at 30 μM in vitro |
|---|---|
| 38 | 0.59 |
| 39 | 1.25 |
| 40 | 0.87 |
| 41 | 0.26 |
| 42 | 0.24 |
| 43 | 0.93 |
| 44 | 0.20 |
| 45 | 0.92 |
| 46 | 0.29 |
| 47 | 0.56 |
| 48 | 0.59 |
| 49 | 0.24 |
| 50 | 0.18 |
| 51 | 0.26 |
| 52 | 0.89 |
| 53 | 0.50 |
| 54 | 0.44 |
| 55 | 0.23 |
| 56 | 0.19 |
| 57 | 0.20 |
| 58 | 0.55 |

TABLE 27

| Ex. No. | $IC_{50}$ (μM) or inhibitory activity (%) at 30 μM in vitro |
|---|---|
| 59 | 0.26 |
| 60 | 0.74 |
| 61 | 0.22 |
| 62 | 0.28 |
| 63 | 0.36 |
| 64 | 6.88 |
| 65 | 0.72 |
| 66 | 1.50 |
| 67 | 0.90 |
| 68 | 5.94 |
| 69 | 1.62 |
| 70 | 38% |
| 71 | 2.47 |
| 72 | 0.40 |
| 73 | 7.09 |
| 74 | 0.85 |
| 75 | 0.21 |
| 76 | 0.22 |
| 77 | 0.24 |
| 78 | 0.15 |
| 79 | 0.23 |
| 80 | 0.71 |
| 81 | 6.09 |
| 82 | 0.15 |
| 83 | 0.19 |
| 84 | 0.11 |
| 85 | 0.16 |
| 86 | 0.83 |
| 87 | 0.37 |

TABLE 28

| Ex. No. | $IC_{50}$ (μM) or inhibitory activity (%) at 30 μM in vitro |
|---|---|
| 88 | 0.16 |
| 89 | 0.12 |
| 90 | 0.29 |
| 91 | 1.53 |
| 92 | 0.69 |
| 93 | 0.51 |
| 94 | 0.11 |
| 95 | 0.12 |
| 96 | 0.29 |
| 97 | 0.13 |

TABLE 28-continued

| Ex. No. | IC$_{50}$ (µM) or inhibitory activity (%) at 30 µM in vitro |
|---|---|
| 98 | 1.13 |
| 99 | 0.87 |
| 100 | 0.82 |
| 101 | 0.37 |
| 102 | 0.51 |
| 103 | 0.18 |
| 104 | 0.19 |
| 105 | 0.10 |
| 106 | 0.23 |
| 107 | 0.65 |
| 108 | 0.16 |
| 109 | 0.17 |
| 110 | 0.15 |
| 111 | 1.10 |
| 112 | 3.09 |
| 113 | 0.56 |
| 114 | 1.20 |
| 115 | 1.80 |

TABLE 29

| Ex. No. | IC$_{50}$ (µM) or inhibitory activity (%) at 30 µM in vitro |
|---|---|
| 116 | 0.18 |
| 117 | 0.39 |
| 118 | 0.64 |
| 119 | 0.64 |
| 120 | 0.12 |
| 121 | 0.33 |
| 122 | 0.96 |

Experimental Example 2

Human EPO Production Activity

The activity of the test compound on human EPO production was measured using Hep3B (AMC) established from human liver-derived cell line.

Hep3B cells were cultured in Eagle-MEM medium containing 10% fetal bovine serum, and the test compound was diluted with dimethyl sulfoxide (DMSO).

Hep3B cells were cultured in a 96-well plate, and a test compound was added at each concentration 24 hr later. After incubation at 37° C. for 24 hr, the culture supernatant was collected. The concentration of human EPO produced in the culture supernatant was measured using a human EPO-ELISA kit (manufactured by StemCell Technologies, 01630) according to the manufacturer's explanation, and the human EPO production activity (%) of the test compound was calculated based on the maximum value of production under the above conditions and the value without addition of the test compound. The human EPO production activity of each compound is shown by EC$_{50}$ (µM) or as human EPO production activity (%) at 30 µM in the following Tables 30 to 34. In these Tables, the values consisting solely of numbers show EC$_{50}$ (µM) and those containing % show human EPO production activity (%) at 30 µm.

TABLE 30

| Ex. No. | EC$_{50}$ (µM) or production activity (%) at 30 µM in vitro |
|---|---|
| 1 | 9.9 |
| 2 | 10.9 |

TABLE 30-continued

| Ex. No. | EC$_{50}$ (µM) or production activity (%) at 30 µM in vitro |
|---|---|
| 3 | 12.4 |
| 4 | 38% |
| 5 | 11.5 |
| 6 | 20.8 |
| 7 | 18.4 |
| 8 | 13.4 |
| 9 | 1% |
| 10 | 0% |
| 11 | 1% |
| 12 | 5% |
| 13 | 1% |
| 14 | 5.1 |
| 15 | 29.1 |
| 16 | 7.0 |
| 17 | 8.8 |
| 18 | 6.1 |
| 19 | 6.6 |
| 20 | 6.6 |
| 21 | 12.0 |
| 22 | 13.7 |
| 23 | 7.8 |
| 24 | 5.4 |
| 25 | 14.1 |
| 26 | 7.5 |
| 27 | 7.7 |
| 28 | 13.9 |
| 29 | 11.3 |

TABLE 31

| Ex. No. | EC$_{50}$ (µM) or production activity (%) at 30 µM in vitro |
|---|---|
| 30 | 15.4 |
| 31 | 12.1 |
| 32 | 15.6 |
| 33 | 10.1 |
| 34 | 15.0 |
| 35 | 43% |
| 36 | 10.5 |
| 37 | 11% |
| 38 | 8.7 |
| 39 | 22.3 |
| 40 | 17.7 |
| 41 | 9.1 |
| 42 | 14.2 |
| 43 | 23.6 |
| 44 | 10.4 |
| 45 | 9.9 |
| 46 | 4.8 |
| 47 | 12.0 |
| 48 | 4.5 |
| 49 | 11.7 |
| 50 | 5.6 |
| 51 | 9.1 |
| 52 | 10.4 |
| 53 | 8.9 |
| 54 | 4.5 |
| 55 | 8.9 |
| 56 | 8.4 |
| 57 | 4.7 |
| 58 | 4.7 |

TABLE 32

| Ex. No. | EC$_{50}$ (µM) or production activity (%) at 30 µM in vitro |
|---|---|
| 59 | 49% |
| 60 | 8.4 |
| 61 | 28.8 |
| 62 | 10.1 |

TABLE 32-continued

| Ex. No. | EC$_{50}$ (μM) or production activity (%) at 30 μM in vitro |
|---|---|
| 63 | 19.7 |
| 64 | 0% |
| 65 | 49% |
| 66 | 21.1 |
| 67 | 14.3 |
| 68 | 0% |
| 69 | 12.0 |
| 70 | 1% |
| 71 | 15.8 |
| 72 | 4.0 |
| 73 | 34% |
| 74 | 8.3 |
| 75 | 23.7 |
| 76 | 18.0 |
| 77 | 18.7 |
| 78 | 6.6 |
| 79 | 7.8 |
| 80 | 23.3 |
| 81 | 33% |
| 82 | 5.4 |
| 83 | 20.7 |
| 84 | 11.0 |
| 85 | 20.6 |
| 86 | 6% |
| 87 | 18.5 |

TABLE 33

| Ex. No. | EC$_{50}$ (μM) or production activity (%) at 30 μM in vitro |
|---|---|
| 88 | 14% |
| 89 | 4.2 |
| 90 | 16.6 |
| 91 | 43% |
| 92 | 18.5 |
| 93 | 16.0 |
| 94 | 9.7 |
| 95 | 4.3 |
| 96 | 5.9 |
| 97 | 3.5 |
| 98 | 25.6 |
| 99 | 20.2 |
| 100 | 18.0 |
| 101 | 6% |
| 102 | 16.0 |
| 103 | 6.9 |
| 104 | 6.3 |
| 105 | 5.9 |
| 106 | 6.0 |
| 107 | 4% |
| 108 | 8.9 |
| 109 | 13.7 |
| 110 | 6.5 |
| 111 | 0% |
| 112 | 0% |
| 113 | 0% |
| 114 | 0% |
| 115 | 0% |

TABLE 34

| Ex. No. | EC$_{50}$ (μM) or production activity (%) at 30 μM in vitro |
|---|---|
| 116 | 5.6 |
| 117 | 7.7 |

As is clear from the above-mentioned results, the compound of the present invention or a pharmaceutically acceptable salt thereof, or a solvate thereof has a human PHD inhibitory activity and a human EPO production activity.

INDUSTRIAL APPLICABILITY

The compound of the present invention or a pharmaceutically acceptable salt thereof, or a solvate thereof inhibits binding of HIF and PHD based on its PHD inhibitory activity and stabilizes HIF, which enables promotion of EPO production.

Hence, the compound of the present invention or a pharmaceutically acceptable salt thereof, or a solvate thereof can be a medicament effective for the prophylaxis or treatment of various diseases and pathologies (disorders) caused by decreased production of EPO, and can be effectively used for the treatment of anemia.

What is claimed is:

1. A compound represented by the following formula [I], or a pharmaceutically acceptable salt thereof, or a solvate thereof:

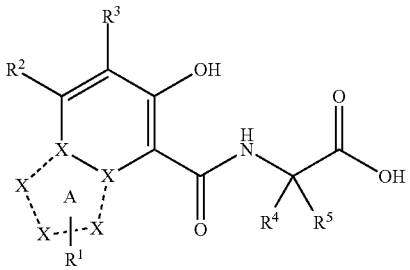

[I]

wherein
the partial structural formula:

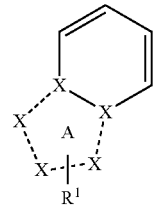

is a group represented by:

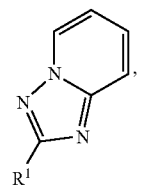

$R^1$ is
(1) a hydrogen atom,
(2) a $C_{1-6}$ alkyl group,
(3) a $C_{6-14}$ aryl group,
(4) a $C_{3-8}$ cycloalkyl group,
(5) a $C_{6-14}$ aryl-$C_{1-6}$ alkyl group, or
(6) a $C_{3-8}$ cycloalkyl-$C_{1-6}$ alkyl group;

$R^2$ is
- (2) a $C_{1-10}$ alkyl group,
- (3) a $C_{6-14}$ aryl group optionally substituted by the same or different 1 to 5 substituents selected from the following group B,
- (4) a $C_{3-8}$ cycloalkyl group optionally substituted by the same or different 1 to 5 substituents selected from the following group B,
- (5) a $C_{3-8}$ cycloalkenyl group optionally substituted by the same or different 1 to 5 substituents selected from the following group B,
- (6) a heteroaryl group optionally substituted by the same or different 1 to 5 substituents selected from the following group B (wherein the heteroaryl has, besides carbon atom, 1 to 6 hetero atoms selected from nitrogen atom, oxygen atom and sulfur atom),
- (7) a $C_{6-14}$ aryl-$C_{1-6}$ alkyl group (wherein $C_{6-14}$ aryl is optionally substituted by the same or different 1 to 5 substituents selected from the following group B), or
- (8) a $C_{3-8}$ cycloalkyl-$C_{1-6}$ alkyl group (wherein $C_{3-8}$ cycloalkyl is optionally substituted by the same or different 1 to 5 substituents selected from the following group B);

$R^3$ is
- (1) a hydrogen atom,
- (2) a halogen atom,
- (3) a $C_{1-6}$ alkyl group,
- (4) a $C_{6-14}$ aryl group,
- (5) a $C_{3-8}$ cycloalkyl group, or
- (6) a $C_{6-14}$ aryl-$C_{1-6}$ alkyl group; and $R^4$ and $R^5$ are each independently
- (1) a hydrogen atom, or
- (2) a $C_{1-6}$ alkyl group, group B:
- (a) a halogen atom,
- (b) a $C_{1-6}$ alkyl group,
- (c) a $C_{3-8}$ cycloalkyl group,
- (d) a cyano group, and
- (e) a halo-$C_{1-6}$ alkyl group.

2. The compound according to claim 1, wherein both $R^4$ and $R^5$ are hydrogen atoms, or a pharmaceutically acceptable salt thereof, or a solvate thereof.

3. The compound according to claim 1, wherein $R^3$ is a hydrogen atom, or a pharmaceutically acceptable salt thereof, or a solvate thereof.

4. The compound according to claim 1, wherein $R^1$ is a hydrogen atom, or a pharmaceutically acceptable salt thereof, or a solvate thereof.

5. The compound according to claim 1, wherein $R^2$ is
- (1) a $C_{1-10}$ alkyl group,
- (2) a $C_{6-14}$ aryl group optionally substituted by the same or different 1 to 5 substituents selected from the above-mentioned group B,
- (3) a $C_{6-14}$ aryl-$C_{1-6}$ alkyl group (wherein $C_{6-14}$ aryl is optionally substituted by the same or different 1 to 5 substituents selected from the above-mentioned group 13), or
- (4) a $C_{3-8}$ cycloalkyl-$C_{1-6}$ alkyl group (wherein $C_{3-8}$ cycloalkyl is optionally substituted by the same or different 1 to 5 substituents selected from the above-mentioned group B), or a pharmaceutically acceptable salt thereof, or a solvate thereof.

6. The compound according to claim 2, wherein $R^3$ is a hydrogen atom, or a pharmaceutically acceptable salt thereof, or a solvate thereof.

7. The compound according to claim 6, wherein $R^1$ is a hydrogen atom, or a pharmaceutically acceptable salt thereof, or a solvate thereof.

8. The compound according to claim 7, wherein $R^2$ is
- (1) a $C_{1-10}$ alkyl group, or
- (2) a $C_{6-14}$ aryl-$C_{1-6}$ alkyl group (wherein $C_{6-14}$ aryl is optionally substituted by the same or different 1 to 5 substituents selected from the above-mentioned group B), or a pharmaceutically acceptable salt thereof, or a solvate thereof.

9. A compound represented by the following formula [I-1] or a pharmaceutically acceptable salt thereof, or a solvate thereof:

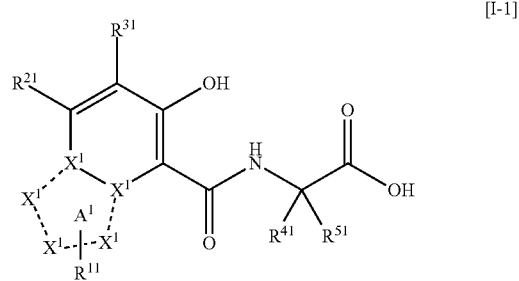

wherein the partial structural formula:

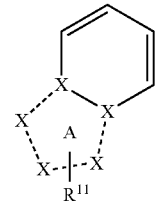

is a group represented by:

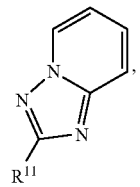

$R^{11}$ is
- (1) a hydrogen atom,
- (2) a $C_{1-6}$ alkyl group,
- (3) a phenyl group,
- (4) a $C_{3-8}$ cycloalkyl group,
- (5) a phenyl-$C_{1-6}$ alkyl group, or
- (6) a $C_{3-8}$ cycloalkyl-$C_{1-6}$ alkyl group;

$R^{21}$ is
- (2) a $C_{1-10}$ alkyl group,
- (3) a phenyl group optionally substituted by the same or different 1 to 5 substituents selected from the following group B,
- (4) a $C_{3-8}$ cycloalkyl group,
- (5) a $C_{3-8}$ cycloalkenyl group, (6) a thienyl group optionally substituted by the same or different 1 to 5 substituents selected from the following group B,
(7) a phenyl-$C_{1-6}$ alkyl group (wherein phenyl is optionally substituted by the same or different 1 to 5 substituents selected from the following group B), or
(8) a $C_{3-8}$ cycloalkyl-$C_{1-6}$ alkyl group;

$R^{31}$ is
(1) a hydrogen atom,
(2) a halogen atom,
(3) a $C_{1-6}$ alkyl group,
(4) a phenyl group,
(5) a $C_{3-8}$ cycloalkyl group, or
(6) a phenyl-$C_{1-6}$ alkyl group; and $R^{41}$ and $R^{51}$ are each independently
(1) a hydrogen atom, or
(2) a $C_{1-6}$ alkyl group group B:
(a) a halogen atom,
(b) a $C_{1-6}$ alkyl group,
(c) a $C_{3-8}$ cycloalkyl group,
(d) a cyano group, and
(e) a halo-$C_{1-6}$ alkyl group.

10. A compound represented by the following formula:

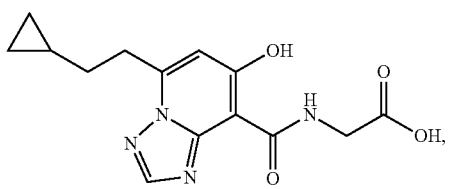

or a pharmaceutically acceptable salt thereof, or a solvate thereof.

11. A compound represented by the following formula:

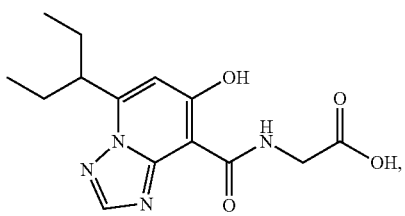

or a pharmaceutically acceptable salt thereof, or a solvate thereof.

12. A compound represented by the following formula:

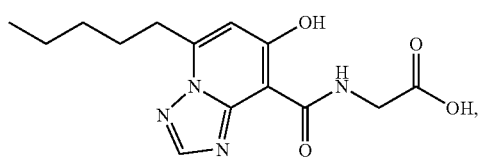

or a pharmaceutically acceptable salt thereof, or a solvate thereof.

13. A compound represented by the following formula:

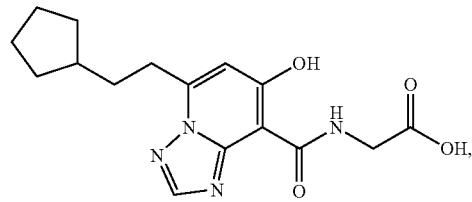

or a pharmaceutically acceptable salt thereof, or a solvate thereof.

14. A compound represented by the following formula:

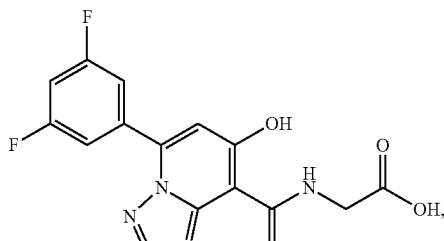

or a pharmaceutically acceptable salt thereof, or a solvate thereof.

15. A compound represented by the following formula:

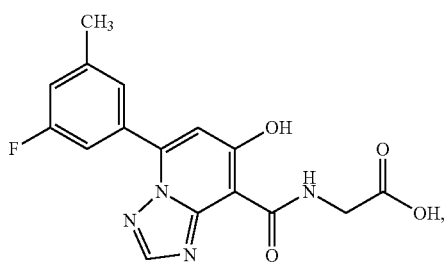

or a pharmaceutically acceptable salt thereof, or a solvate thereof.

16. A compound represented by the following formula:

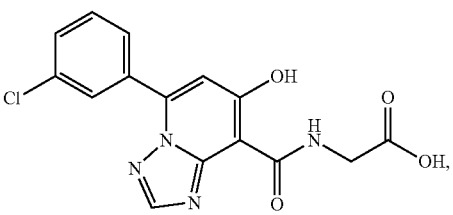

or a pharmaceutically acceptable salt thereof, or a solvate thereof.

17. A compound represented by the following formula:

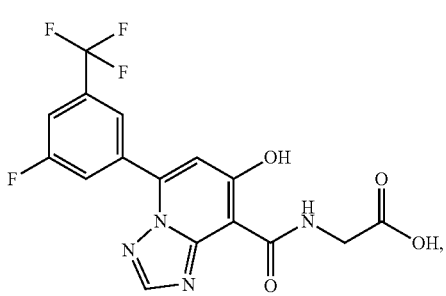

or a pharmaceutically acceptable salt thereof, or a solvate thereof.

18. A compound represented by the following formula:

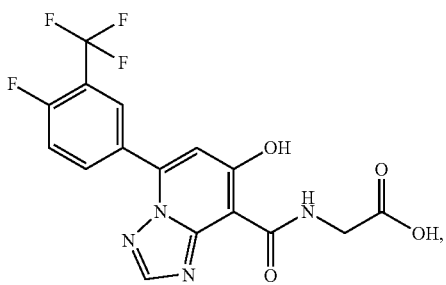

or a pharmaceutically acceptable salt thereof, or a solvate thereof.

19. A compound represented by the following formula:

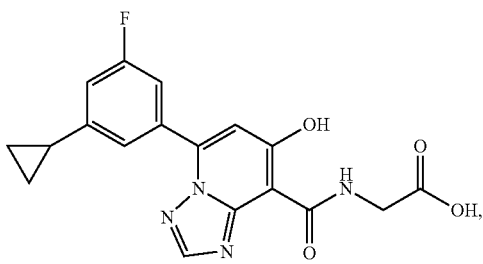

or a pharmaceutically acceptable salt thereof, or a solvate thereof.

20. A compound represented by the following formula:

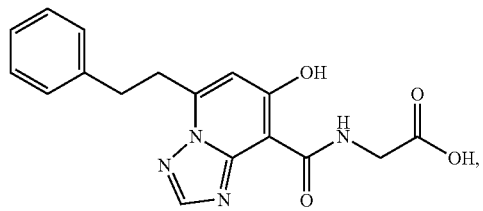

or a pharmaceutically acceptable salt thereof, or a solvate thereof.

21. A pharmaceutical composition comprising the compound according to claim 1, or a pharmaceutically acceptable salt thereof, or a solvate thereof, and a pharmaceutically acceptable carrier.

22. A method of inhibiting prolyl hydroxylase, comprising administering an effective amount of the compound according to claim 1, or a pharmaceutically acceptable salt thereof, or a solvate thereof to a mammal.

23. A method of inducing erythropoietin production, comprising administering an effective amount of the compound according to claim 1, or a pharmaceutically acceptable salt thereof, or a solvate thereof to a mammal.

24. A method of treating anemia, comprising administering an effective amount of the compound according to claim 1, or a pharmaceutically acceptable salt thereof, or a solvate thereof to a mammal.

25. A method of treating renal anemia, comprising administering an effective amount of the compound according to claim 1, or a pharmaceutically acceptable salt thereof, or a solvate thereof to a mammal.

26. A pharmaceutical composition comprising the compound according to any one of claims 10 to 20, or a pharmaceutically acceptable salt thereof, or a solvate thereof, and a pharmaceutically acceptable carrier.

27. A method of inhibiting prolyl hydroxylase, comprising administering an effective amount of the compound according to any one of claims 10 to 20, or a pharmaceutically acceptable salt thereof, or a solvate thereof to a mammal.

28. A method of inducing erythropoietin production, comprising administering an effective amount of the compound according to any one of claims 10 to 20, or a pharmaceutically acceptable salt thereof, or a solvate thereof to a mammal.

29. A method of treating anemia, comprising administering an effective amount of the compound according to any one of claims 10 to 20, or a pharmaceutically acceptable salt thereof, or a solvate thereof to a mammal.

30. A method of treating renal anemia, comprising administering an effective amount of the compound according to any one of claims 10 to 20, or a pharmaceutically acceptable salt thereof, or a solvate thereof to a mammal.

* * * * *

UNITED STATES PATENT AND TRADEMARK OFFICE
CERTIFICATE OF CORRECTION

PATENT NO.        : 8,283,465 B2
APPLICATION NO.   : 12/837679
DATED             : October 9, 2012
INVENTOR(S)       : Ikuo Mitani It is certified that error appears in the above-identified patent and that said Letters Patent is hereby corrected as shown below:

In column 151, line 59, in claim 5, delete "13)," and insert -- B), --, therefor.

In column 152, lines 31-42, in claim 9, delete " 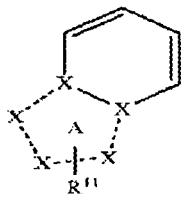 " and insert -- 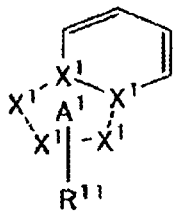 --, therefor.

Signed and Sealed this
Twenty-second Day of January, 2013

David J. Kappos
*Director of the United States Patent and Trademark Office*